(12) United States Patent
Vranic et al.

(10) Patent No.: US 7,862,825 B2
(45) Date of Patent: Jan. 4, 2011

(54) METHOD OF CONTROLLING TIGHT BLOOD GLUCOSE BY SOMATOSTATIN RECEPTOR ANTAGONISTS

(76) Inventors: Mladen Vranic, 307 Bessborough Drive, Toronto, Ontario (CA) M4G 3K9; Jessica Yue, 1 Emerson Hill Drive, Unionville, Ontario (CA) L3P 7C6; Suad Efendic, Stjärnvägen 16 B, Lindingö (SE) SE-181 34

( * ) Notice: Subject to any disclaimer, the term of this patent is extended or adjusted under 35 U.S.C. 154(b) by 21 days.

(21) Appl. No.: 12/035,068

(22) Filed: Feb. 21, 2008

(65) Prior Publication Data

US 2009/0004195 A1    Jan. 1, 2009

Related U.S. Application Data

(60) Provisional application No. 60/890,965, filed on Feb. 21, 2007.

(51) Int. Cl.
*A61K 39/00* (2006.01)
(52) U.S. Cl. .................. 424/198.1; 424/139.1; 530/300
(58) Field of Classification Search ........................ None
See application file for complete search history.

(56) References Cited

U.S. PATENT DOCUMENTS

| | | | |
|---|---|---|---|
| 5,846,934 | A | 12/1998 | Bass et al. |
| 6,495,589 | B2 | 12/2002 | Hay et al. |
| 6,696,418 | B1 | 2/2004 | Hay et al. |
| 6,720,330 | B2 | 4/2004 | Hay et al. |
| 6,867,202 | B1 | 3/2005 | Carpino et al. |

FOREIGN PATENT DOCUMENTS

| WO | WO 94/02163 | 2/1994 |
|---|---|---|
| WO | WO 2006/063465 | 6/2006 |

OTHER PUBLICATIONS

Rizza et al., J. Clin. Invest. 64: 62-71, 1979.*

Tulipano, G., et al., "Characterization of New Selective Somatostatin Receptor Subtype-2 (sst2) Antagonists, BIM-23627 and BIM-23454. Effects of BIM-23627 on GH Release in Anesthetized Male Rats after Short-Term High-Dose Dexamethasone Treatment", Endocrinology, Apr. 2002, pp. 1218-1224, vol. 143, Issue 4.

Tulipano, G., et al., "The somatostatin subtype-2 receptor antagonist, BIM-23627, improves the catabolic effects induced by long-term glucocorticoid treatment in the rat", Regulatory Peptides, 2005, pp. 85-92, vol. 125.

Cejvan, K., et al., "Gliclazide Directly Inhibits Arginine-Induced Glucagon Release", Diabetes, Dec. 2002, pp. S381-S384, vol. 51, Supplement 3.

Cejvan, K., et al., "Intra-Islet Somatostatin Regulates Glucagon Release via Type 2 Somatostatin Receptors in Rats", Diabetes, May 2003, pp. 1176-1181, vol. 52.

Brunicardi, F. et al., "Activation of Somatostatin Receptor Subtype 2 Inhibits Insulin Secretion in the Isolated Perfused Human Pancreas", Pancreas, Nov. 2003, pp. e84-e89, vol. 27, No. 4.

Singh, V., et al., "Characterization of Somatostatin Receptor Subtype-Specific Regulation of Insulin and Glucagon Secretion: An in Vitro Study on Isolated Human Pancreatic Islets", The Journal of Clinical Endocrinology & Metabolism, Feb. 2007 (First published online Nov. 2006), pp. 673-680, vol. 92, Issue 2.

Chan, J.C.N., et al., "Drug-induced disorders of glucose metabolism, Mechanisms and Management", Drug Saf., Aug. 1996, pp. 135-157, vol. 15, Issue 2.

Yue, J., et al., "The impact of antagonizing somatostatin actions on glucagon release during hypoglycemia", CIHR's Funded Research Database, CIHR Doctoral Research Award, 2006. (Abstract).

* cited by examiner

*Primary Examiner*—Robert Landsman
*Assistant Examiner*—Gyan Chandra
(74) *Attorney, Agent, or Firm*—Dann, Dorfman, Herrell & Skillman; Robert C. Netter; Kathleen D. Rigaut

(57) ABSTRACT

The present disclosure provides methods and uses for controlling tight blood glucose levels in a subject comprising administering an effective amount of a somatostatin inhibitor. The present disclosure provides methods and uses for treating or preventing hypoglycemia in a subject comprising administering an effective amount of a somatostatin inhibitor.

19 Claims, 9 Drawing Sheets

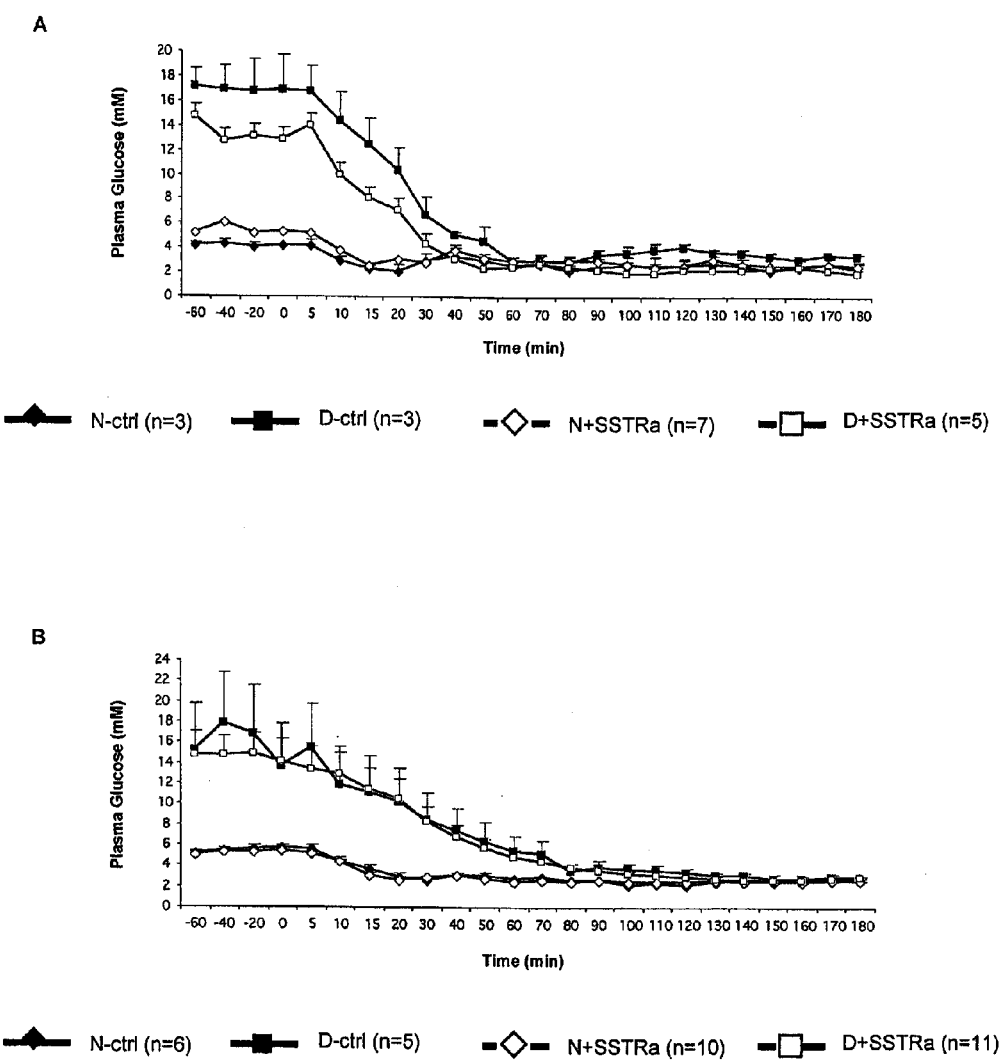
Figure 1. Glycemia during pre-clamp infusion (-60 to 0 min) and hypoglycemia (0 to 180 min; target: 2.5-3.0 mM). Insulin injection s.c. after time 0. SSTRa/saline infused throughout 4 h.
(A) Insulin: 10 U/kg; SSTRa: 1500 nmol/kg/h. (B) Insulin: 5 U/kg; SSTRa: 3000 nmol/kg/h.

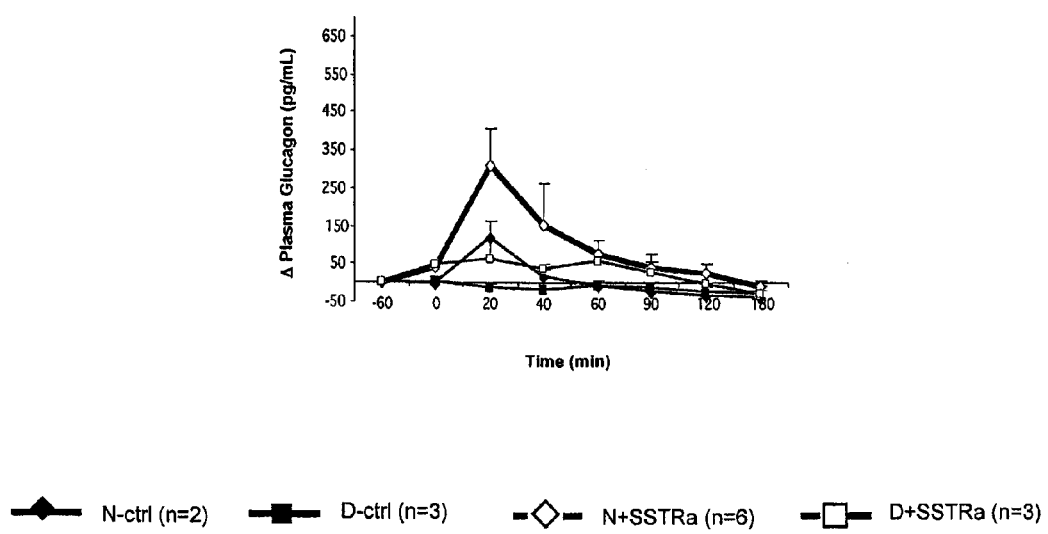
Figure 2. Glucagon responses. Insulin: 10 U/kg; SSTRa: 1500 nmol/kg/h.

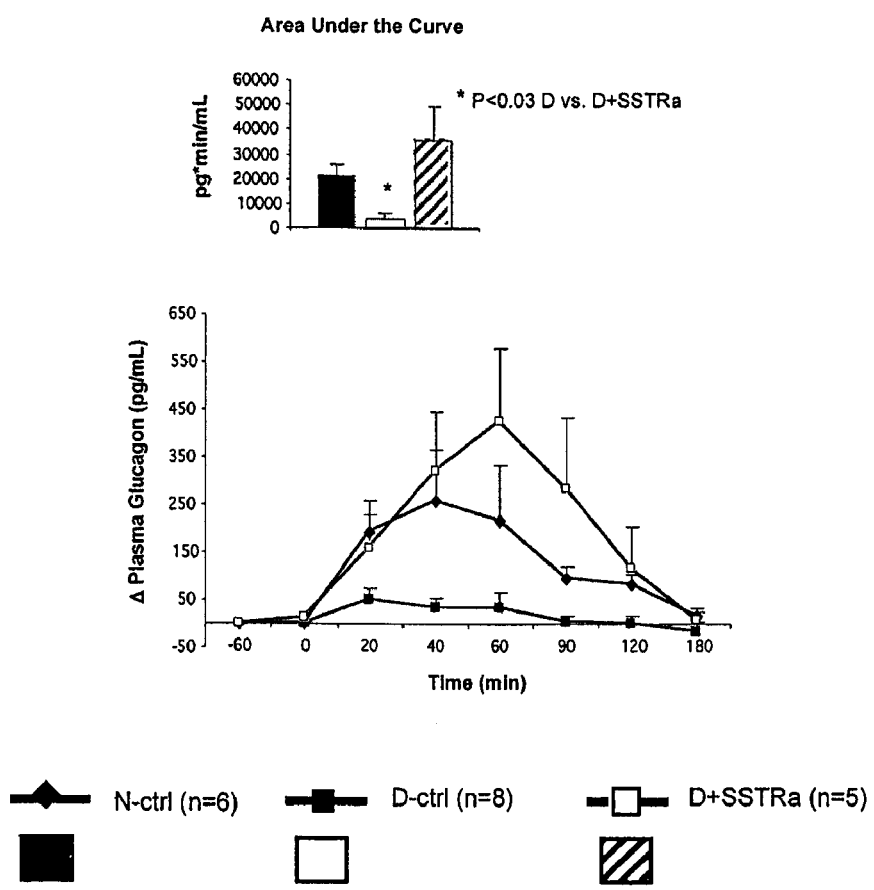
Figure 3. Glucagon responses. Insulin: 5 U/kg; SSTRa: 3000 nmol/kg/h.

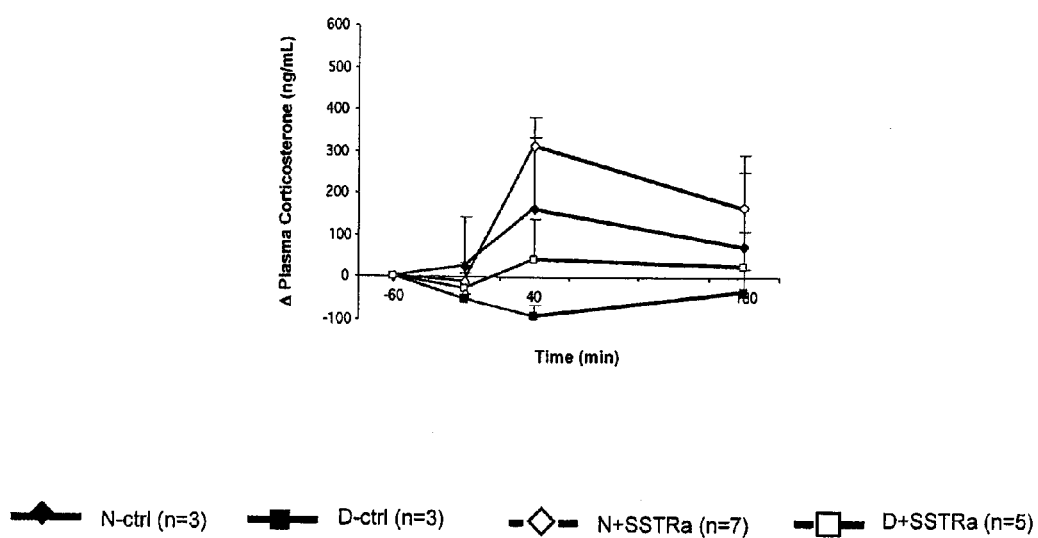
Figure 4. Corticosterone responses. Insulin: 10 U/kg; SSTRa: 1500 nmol/kg/h.

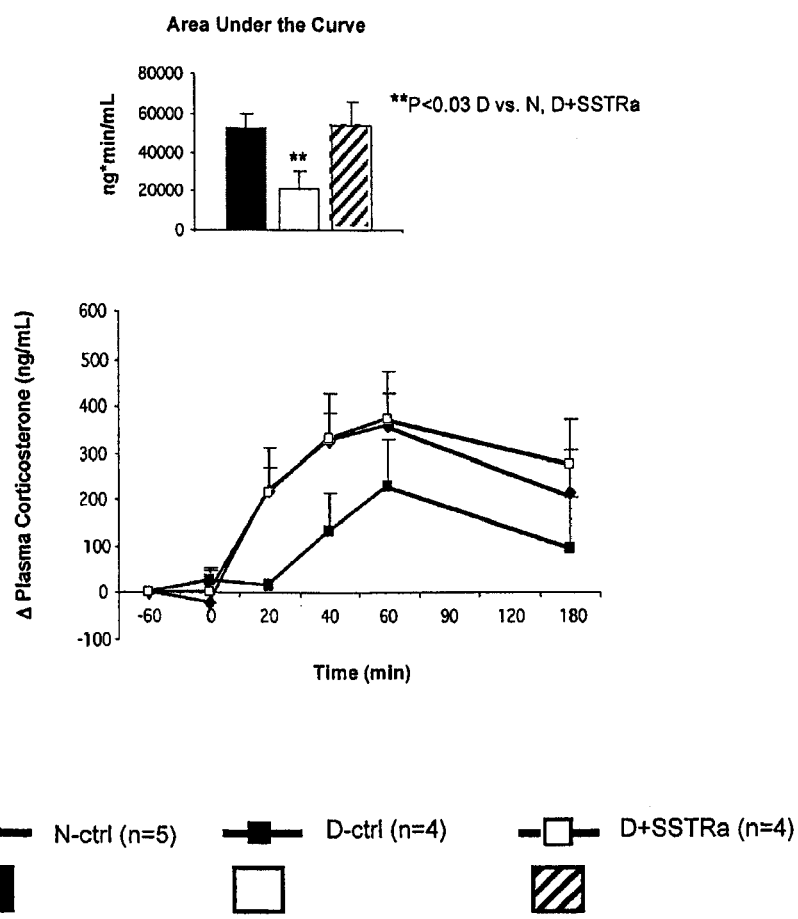
Figure 5. Corticosterone responses. Insulin: 5 U/kg; SSTRa: 3000 nmol/kg/h.

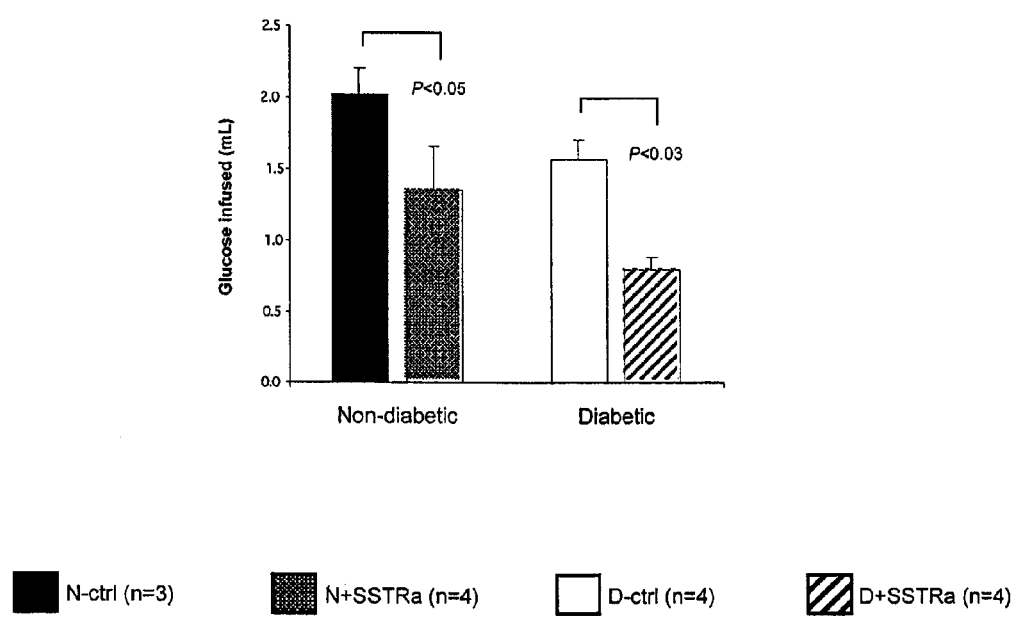
Figure 6. Volume of 50% glucose solution infused during hypoglycemia.
Insulin: 5 U/kg; SSTRa: 3000 nmol/kg/h.

Figure 7. Epinephrine responses. Insulin: 10 U/kg; SSTRa: 1500 nmol/kg/h.
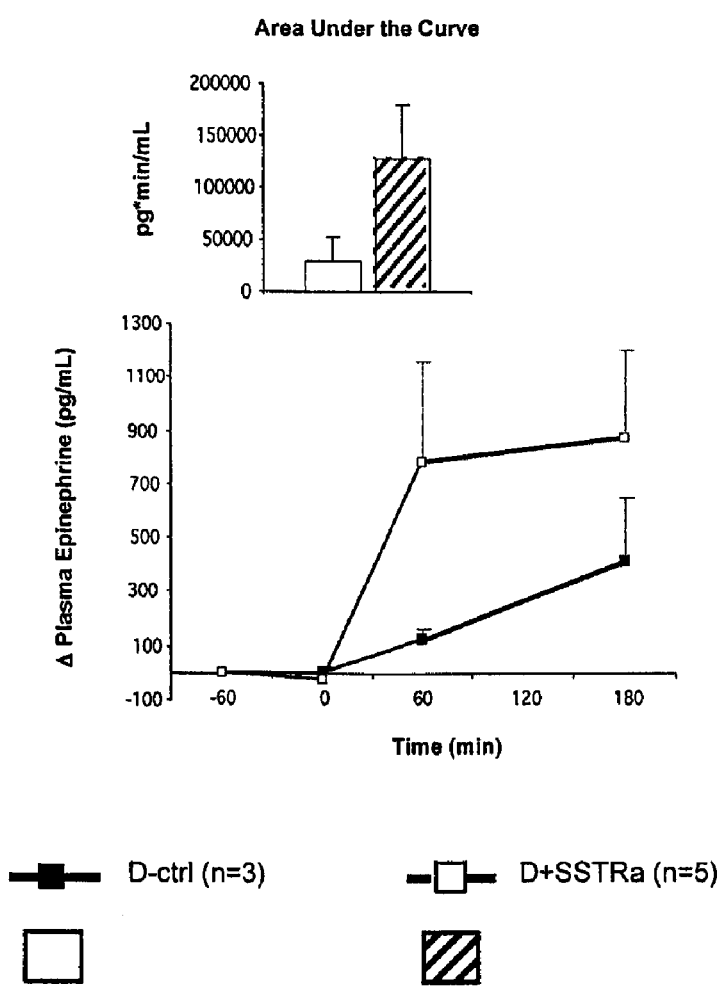

Figure 8. Norepinephrine responses. Insulin: 10 U/kg; SSTRa: 1500 nmol/kg/h.
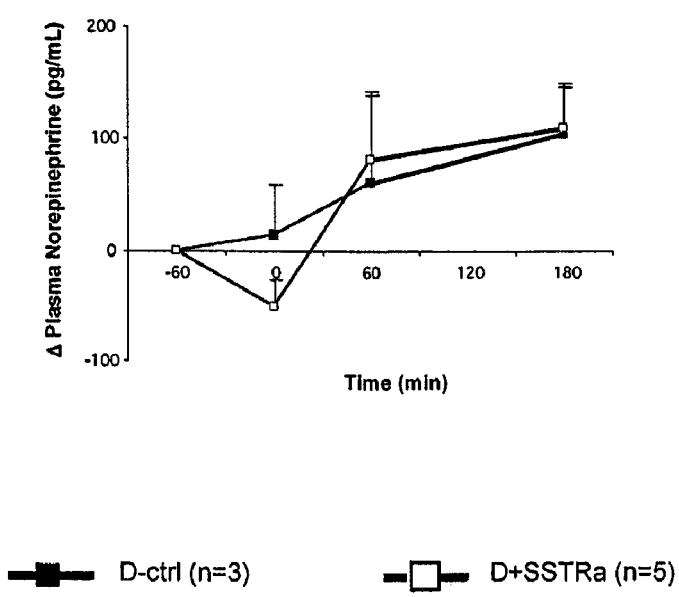

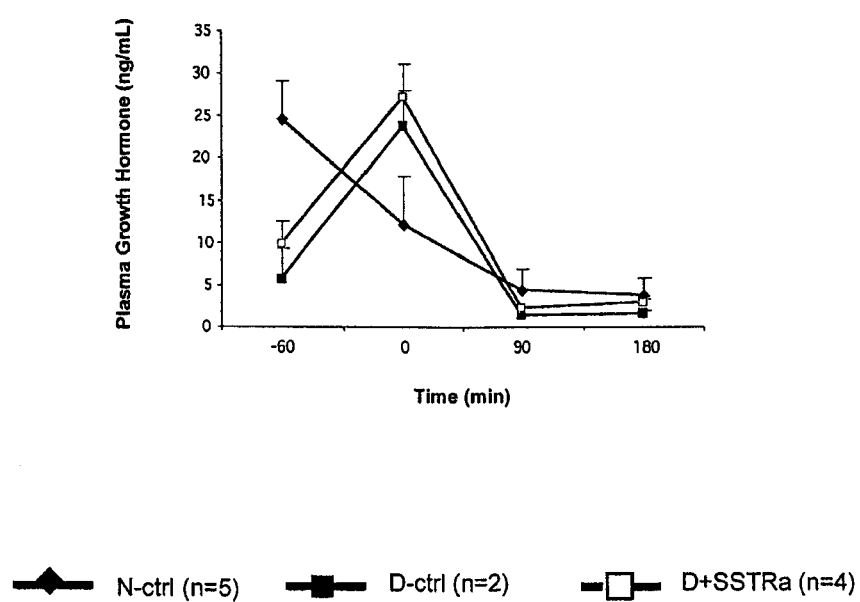
Figure 9. Growth hormone levels. Insulin: 10 U/kg; SSTRa: 1500 nmol/kg/h.

SEQUENCE LISTING

<160> NUMBER OF SEQ ID NOS: 34

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 28
<212> TYPE: PRT
<213> ORGANISM: Homo sapiens

<400> SEQUENCE: 2

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 3
<211> LENGTH: 116
<212> TYPE: PRT
<213> ORGANISM: Homo sapiens

<400> SEQUENCE: 3

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
                20                  25                  30

Gln Phe Leu Gln Lys Ser Leu Ala Ala Ala Ala Gly Lys Gln Glu Leu
            35                  40                  45

Ala Lys Tyr Phe Leu Ala Glu Leu Leu Ser Glu Pro Asn Gln Thr Glu
        50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 4
<211> LENGTH: 116
<212> TYPE: PRT
<213> ORGANISM: Rat

<400> SEQUENCE: 4

Met Leu Ser Cys Arg Leu Gln Cys Ala Leu Ala Ala Leu Cys Ile Val
1               5                   10                  15

Leu Ala Leu Gly Gly Val Thr Gly Ala Pro Ser Asp Pro Arg Leu Arg
                20                  25                  30

Gln Phe Leu Gln Lys Ser Leu Ala Ala Ala Thr Gly Lys Gln Glu Leu
            35                  40                  45

Ala Lys Tyr Phe Leu Ala Glu Leu Leu Ser Glu Pro Asn Gln Thr Glu

```
            50                  55                  60
Asn Asp Ala Leu Glu Pro Glu Asp Leu Pro Gln Ala Ala Glu Gln Asp
 65                  70                  75                  80

Glu Met Arg Leu Glu Leu Gln Arg Ser Ala Asn Ser Asn Pro Ala Met
                 85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 5
<211> LENGTH: 391
<212> TYPE: PRT
<213> ORGANISM: Homo sapiens

<400> SEQUENCE: 5

Met Phe Pro Asn Gly Thr Ala Ser Ser Pro Ser Ser Ser Pro Ser Pro
 1               5                  10                  15

Ser Pro Gly Ser Cys Gly Glu Gly Gly Ser Arg Gly Pro Gly Ala
            20                  25                  30

Gly Ala Ala Asp Gly Met Glu Glu Pro Gly Arg Asn Ala Ser Gln Asn
             35                  40                  45

Gly Thr Leu Ser Glu Gly Gln Gly Ser Ala Ile Leu Ile Ser Phe Ile
         50                  55                  60

Tyr Ser Val Val Cys Leu Val Gly Leu Cys Gly Asn Ser Met Val Ile
 65                  70                  75                  80

Tyr Val Ile Leu Arg Tyr Ala Lys Met Lys Thr Ala Thr Asn Ile Tyr
                 85                  90                  95

Ile Leu Asn Leu Ala Ile Ala Asp Glu Leu Leu Met Leu Ser Val Pro
            100                 105                 110

Phe Leu Val Thr Ser Thr Leu Leu Arg His Trp Pro Phe Gly Ala Leu
        115                 120                 125

Leu Cys Arg Leu Val Leu Ser Val Asp Ala Val Asn Met Phe Thr Ser
    130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
    210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285

Val Val Gln Leu Val Asn Val Phe Ala Glu Gln Asp Asp Ala Thr Val
    290                 295                 300
```

```
Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
                340                 345                 350

Tyr Tyr Ala Thr Ala Leu Lys Ser Arg Ala Tyr Ser Val Glu Asp Phe
            355                 360                 365

Gln Pro Glu Asn Leu Glu Ser Gly Gly Val Phe Arg Asn Gly Thr Cys
        370                 375                 380

Thr Ser Arg Ile Thr Thr Leu
385                 390

<210> SEQ ID NO 6
<211> LENGTH: 391
<212> TYPE: PRT
<213> ORGANISM: Rat

<400> SEQUENCE: 6

Met Phe Pro Asn Gly Thr Ala Pro Ser Pro Thr Ser Ser Pro Ser Ser
1               5                   10                  15

Ser Pro Gly Gly Cys Gly Glu Gly Val Cys Ser Arg Gly Pro Gly Ser
                20                  25                  30

Gly Ala Ala Asp Gly Met Glu Glu Pro Gly Arg Asn Ser Ser Gln Asn
            35                  40                  45

Gly Thr Leu Ser Glu Gly Gln Gly Ser Ala Ile Leu Ile Ser Phe Ile
        50                  55                  60

Tyr Ser Val Val Cys Leu Val Gly Leu Cys Gly Asn Ser Met Val Ile
65                  70                  75                  80

Tyr Val Ile Leu Arg Tyr Ala Lys Met Lys Thr Ala Thr Asn Ile Tyr
                85                  90                  95

Ile Leu Asn Leu Ala Ile Ala Asp Glu Leu Leu Met Leu Ser Val Pro
                100                 105                 110

Phe Leu Val Thr Ser Thr Leu Leu Arg His Trp Pro Phe Gly Ala Leu
            115                 120                 125

Leu Cys Arg Leu Val Leu Ser Val Asp Ala Val Asn Met Phe Thr Ser
130                 135                 140

Ile Tyr Cys Leu Thr Val Leu Ser Val Asp Arg Tyr Val Ala Val Val
145                 150                 155                 160

His Pro Ile Lys Ala Ala Arg Tyr Arg Arg Pro Thr Val Ala Lys Val
                165                 170                 175

Val Asn Leu Gly Val Trp Val Leu Ser Leu Leu Val Ile Leu Pro Ile
            180                 185                 190

Val Val Phe Ser Arg Thr Ala Ala Asn Ser Asp Gly Thr Val Ala Cys
        195                 200                 205

Asn Met Leu Met Pro Glu Pro Ala Gln Arg Trp Leu Val Gly Phe Val
        210                 215                 220

Leu Tyr Thr Phe Leu Met Gly Phe Leu Leu Pro Val Gly Ala Ile Cys
225                 230                 235                 240

Leu Cys Tyr Val Leu Ile Ile Ala Lys Met Arg Met Val Ala Leu Lys
                245                 250                 255

Ala Gly Trp Gln Gln Arg Lys Arg Ser Glu Arg Lys Ile Thr Leu Met
            260                 265                 270

Val Met Met Val Val Met Val Phe Val Ile Cys Trp Met Pro Phe Tyr
        275                 280                 285
```

```
Val Val Gln Leu Val Asn Val Phe Ala Glu Gln Asp Asp Ala Thr Val
    290                 295                 300

Ser Gln Leu Ser Val Ile Leu Gly Tyr Ala Asn Ser Cys Ala Asn Pro
305                 310                 315                 320

Ile Leu Tyr Gly Phe Leu Ser Asp Asn Phe Lys Arg Ser Phe Gln Arg
                325                 330                 335

Ile Leu Cys Leu Ser Trp Met Asp Asn Ala Ala Glu Glu Pro Val Asp
            340                 345                 350

Tyr Tyr Ala Thr Ala Leu Lys Ser Arg Ala Tyr Ser Val Glu Asp Phe
        355                 360                 365

Gln Pro Glu Asn Leu Glu Ser Gly Gly Val Phe Arg Asn Gly Thr Cys
370                 375                 380

Ala Ser Arg Ile Ser Thr Leu
385                 390

<210> SEQ ID NO 7
<211> LENGTH: 369
<212> TYPE: PRT
<213> ORGANISM: Homo sapiens

<400> SEQUENCE: 7

Met Asp Met Ala Asp Glu Pro Leu Asn Gly Ser His Thr Trp Leu Ser
1               5                   10                  15

Ile Pro Phe Asp Leu Asn Gly Ser Val Val Ser Thr Asn Thr Ser Asn
                20                  25                  30

Gln Thr Glu Pro Tyr Tyr Asp Leu Thr Ser Asn Ala Val Leu Thr Phe
            35                  40                  45

Ile Tyr Phe Val Val Cys Ile Ile Gly Leu Cys Gly Asn Thr Leu Val
    50                  55                  60

Ile Tyr Val Ile Leu Arg Tyr Ala Lys Met Lys Thr Ile Thr Asn Ile
65                  70                  75                  80

Tyr Ile Leu Asn Leu Ala Ile Ala Asp Glu Leu Phe Met Leu Gly Leu
                85                  90                  95

Pro Phe Leu Ala Met Gln Val Ala Leu Val His Trp Pro Phe Gly Lys
                100                 105                 110

Ala Ile Cys Arg Val Val Met Thr Val Asp Gly Ile Asn Gln Phe Thr
            115                 120                 125

Ser Ile Phe Cys Leu Thr Val Met Ser Ile Asp Arg Tyr Leu Ala Val
    130                 135                 140

Val His Pro Ile Lys Ser Ala Lys Trp Arg Arg Pro Arg Thr Ala Lys
145                 150                 155                 160

Met Ile Thr Met Ala Val Trp Gly Val Ser Leu Leu Val Ile Leu Pro
                165                 170                 175

Ile Met Ile Tyr Ala Gly Leu Arg Ser Asn Gln Trp Gly Arg Ser Ser
                180                 185                 190

Cys Thr Ile Asn Trp Pro Gly Glu Ser Gly Ala Trp Tyr Thr Gly Phe
            195                 200                 205

Ile Ile Tyr Thr Phe Ile Leu Gly Phe Leu Val Pro Leu Thr Ile Ile
    210                 215                 220

Cys Leu Cys Tyr Leu Phe Ile Ile Ile Lys Val Lys Ser Ser Gly Ile
225                 230                 235                 240

Arg Val Gly Ser Ser Lys Arg Lys Lys Ser Glu Lys Lys Val Thr Arg
                245                 250                 255

Met Val Ser Ile Val Val Ala Val Phe Ile Phe Cys Trp Leu Pro Phe
```

-continued

```
               260                 265                 270
Tyr Ile Phe Asn Val Ser Ser Val Ser Met Ala Ile Ser Pro Thr Pro
            275                 280                 285
Ala Leu Lys Gly Met Phe Asp Phe Val Val Leu Thr Tyr Ala Asn
        290                 295                 300
Ser Cys Ala Asn Pro Ile Leu Tyr Ala Phe Leu Ser Asp Asn Phe Lys
305                 310                 315                 320
Lys Ser Phe Gln Asn Val Leu Cys Leu Val Lys Val Ser Gly Thr Asp
                325                 330                 335
Asp Gly Glu Arg Ser Asp Ser Lys Gln Asp Lys Ser Arg Leu Asn Glu
            340                 345                 350
Thr Thr Glu Thr Gln Arg Thr Leu Leu Asn Gly Asp Leu Gln Thr Ser
        355                 360                 365
Ile
```

<210> SEQ ID NO 8
<211> LENGTH: 369
<212> TYPE: PRT
<213> ORGANISM: Rat

<400> SEQUENCE: 8

```
Met Glu Leu Thr Ser Glu Gln Phe Asn Gly Ser Gln Val Trp Ile Pro
1               5                   10                  15
Ser Pro Phe Asp Leu Asn Gly Ser Leu Gly Pro Ser Asn Gly Ser Asn
            20                  25                  30
Gln Thr Glu Pro Tyr Tyr Asp Met Thr Ser Asn Ala Val Leu Thr Phe
        35                  40                  45
Ile Tyr Phe Val Val Cys Val Val Gly Leu Cys Gly Asn Thr Leu Val
    50                  55                  60
Ile Tyr Val Ile Leu Arg Tyr Ala Lys Met Lys Thr Ile Thr Asn Ile
65                  70                  75                  80
Tyr Ile Leu Asn Leu Ala Ile Ala Asp Glu Leu Phe Met Leu Gly Leu
                85                  90                  95
Pro Phe Leu Ala Met Gln Val Ala Leu Val His Trp Pro Phe Gly Lys
            100                 105                 110
Ala Ile Cys Arg Val Val Met Thr Val Asp Gly Ile Asn Gln Phe Thr
        115                 120                 125
Ser Ile Phe Cys Leu Thr Val Met Ser Ile Asp Arg Tyr Leu Ala Val
    130                 135                 140
Val His Pro Ile Lys Ser Ala Lys Trp Arg Arg Pro Arg Thr Ala Lys
145                 150                 155                 160
Met Ile Asn Val Ala Val Trp Gly Val Ser Leu Leu Val Ile Leu Pro
                165                 170                 175
Ile Met Ile Tyr Ala Gly Leu Arg Ser Asn Gln Trp Gly Arg Ser Ser
            180                 185                 190
Cys Thr Ile Asn Trp Pro Gly Glu Ser Gly Ala Trp Tyr Thr Gly Phe
        195                 200                 205
Ile Ile Tyr Ala Phe Ile Leu Gly Phe Leu Val Pro Leu Thr Ile Ile
    210                 215                 220
Cys Leu Cys Tyr Leu Phe Ile Ile Ile Lys Val Lys Ser Ser Gly Ile
225                 230                 235                 240
Arg Val Gly Ser Ser Lys Arg Lys Lys Ser Glu Lys Lys Val Thr Arg
                245                 250                 255
Met Val Ser Ile Val Val Ala Val Phe Ile Phe Cys Trp Leu Pro Phe
```

```
                     260                 265                 270
Tyr Ile Phe Asn Val Ser Ser Val Ser Val Ala Ile Ser Pro Thr Pro
            275                 280                 285
Ala Leu Lys Gly Met Phe Asp Phe Val Val Ile Leu Thr Tyr Ala Asn
        290                 295                 300
Ser Cys Ala Asn Pro Ile Leu Tyr Ala Phe Leu Ser Asp Asn Phe Lys
305                 310                 315                 320
Lys Ser Phe Gln Asn Val Leu Cys Leu Val Lys Val Ser Gly Ala Glu
            325                 330                 335
Asp Gly Glu Arg Ser Asp Ser Lys Gln Asp Lys Ser Arg Leu Asn Glu
        340                 345                 350
Thr Thr Glu Thr Gln Arg Thr Leu Leu Asn Gly Asp Leu Gln Thr Ser
        355                 360                 365
Ile

<210> SEQ ID NO 9
<211> LENGTH: 418
<212> TYPE: PRT
<213> ORGANISM: Homo sapiens

<400> SEQUENCE: 9

Met Asp Met Leu His Pro Ser Val Ser Thr Thr Ser Glu Pro Glu
1               5                   10                  15

Asn Ala Ser Ser Ala Trp Pro Pro Asp Ala Thr Leu Gly Asn Val Ser
            20                  25                  30

Ala Gly Pro Ser Pro Ala Gly Leu Ala Val Ser Gly Val Leu Ile Pro
        35                  40                  45

Leu Val Tyr Leu Val Val Cys Val Val Gly Leu Leu Gly Asn Ser Leu
    50                  55                  60

Val Ile Tyr Val Val Leu Arg His Thr Ala Ser Pro Ser Val Thr Asn
65                  70                  75                  80

Val Tyr Ile Leu Asn Leu Ala Leu Ala Asp Glu Leu Phe Met Leu Gly
                85                  90                  95

Leu Pro Phe Leu Ala Ala Gln Asn Ala Leu Ser Tyr Trp Pro Phe Gly
            100                 105                 110

Ser Leu Met Cys Arg Leu Val Met Ala Val Asp Gly Ile Asn Gln Phe
        115                 120                 125

Thr Ser Ile Phe Cys Leu Thr Val Met Ser Val Asp Arg Tyr Leu Ala
    130                 135                 140

Val Val His Pro Thr Arg Ser Ala Arg Trp Arg Thr Ala Pro Val Ala
145                 150                 155                 160

Arg Thr Val Ser Ala Ala Val Trp Val Ala Ser Ala Val Val Val Leu
                165                 170                 175

Pro Val Val Val Phe Ser Gly Val Pro Arg Gly Met Ser Thr Cys His
            180                 185                 190

Met Gln Trp Pro Glu Pro Ala Ala Trp Arg Ala Gly Phe Ile Ile
        195                 200                 205

Tyr Thr Ala Ala Leu Gly Phe Phe Gly Pro Leu Leu Val Ile Cys Leu
    210                 215                 220

Cys Tyr Leu Leu Ile Val Val Lys Val Arg Ser Ala Gly Arg Arg Val
225                 230                 235                 240

Trp Ala Pro Ser Cys Gln Arg Arg Arg Ser Glu Arg Arg Val Thr
                245                 250                 255

Arg Met Val Val Ala Val Val Ala Leu Phe Val Leu Cys Trp Met Pro
```

```
                260                 265                 270
Phe Tyr Val Leu Asn Ile Val Asn Val Val Cys Pro Leu Pro Glu Glu
            275                 280                 285
Pro Ala Phe Phe Gly Leu Tyr Phe Leu Val Val Ala Leu Pro Tyr Ala
            290                 295                 300
Asn Ser Cys Ala Asn Pro Ile Leu Tyr Gly Phe Leu Ser Tyr Arg Phe
305                 310                 315                 320
Lys Gln Gly Phe Arg Arg Val Leu Leu Arg Pro Ser Arg Arg Val Arg
                325                 330                 335
Ser Gln Glu Pro Thr Val Gly Pro Pro Glu Lys Thr Glu Glu Glu Asp
            340                 345                 350
Glu Glu Glu Glu Asp Gly Glu Glu Ser Arg Glu Gly Gly Lys Gly Lys
            355                 360                 365
Glu Met Asn Gly Arg Val Ser Gln Ile Thr Gln Pro Gly Thr Ser Gly
            370                 375                 380
Gln Glu Arg Pro Pro Ser Arg Val Ala Ser Lys Glu Gln Gln Leu Leu
385                 390                 395                 400
Pro Gln Glu Ala Ser Thr Gly Glu Lys Ser Ser Thr Met Arg Ile Ser
                405                 410                 415
Tyr Leu

<210> SEQ ID NO 10
<211> LENGTH: 428
<212> TYPE: PRT
<213> ORGANISM: Rat

<400> SEQUENCE: 10

Met Ala Ala Val Thr Tyr Pro Ser Ser Val Pro Thr Thr Leu Asp Pro
1               5                   10                  15
Gly Asn Ala Ser Ser Ala Trp Pro Leu Asp Thr Ser Leu Gly Asn Ala
            20                  25                  30
Ser Ala Gly Thr Ser Leu Ala Gly Leu Ala Val Ser Gly Ile Leu Ile
            35                  40                  45
Ser Leu Val Tyr Leu Val Val Cys Val Val Gly Leu Leu Gly Asn Ser
        50                  55                  60
Leu Val Ile Tyr Val Val Leu Arg His Thr Ser Ser Pro Ser Val Thr
65                  70                  75                  80
Ser Val Tyr Ile Leu Asn Leu Ala Leu Ala Asp Glu Leu Phe Met Leu
                85                  90                  95
Gly Leu Pro Phe Leu Ala Ala Gln Asn Ala Leu Ser Tyr Trp Pro Phe
            100                 105                 110
Gly Ser Leu Met Cys Arg Leu Val Met Ala Val Asp Gly Ile Asn Gln
            115                 120                 125
Phe Thr Ser Ile Phe Cys Leu Thr Val Met Ser Val Asp Arg Tyr Leu
            130                 135                 140
Ala Val Val His Pro Thr Arg Ser Ala Arg Trp Arg Thr Ala Pro Val
145                 150                 155                 160
Ala Arg Met Val Ser Ala Ala Val Trp Val Ala Ser Ala Val Val Val
                165                 170                 175
Leu Pro Val Val Val Phe Ser Gly Val Pro Arg Gly Met Ser Thr Cys
            180                 185                 190
His Met Gln Trp Pro Glu Pro Ala Ala Ala Trp Arg Thr Ala Phe Ile
            195                 200                 205
Ile Tyr Thr Ala Ala Leu Gly Phe Phe Gly Pro Leu Leu Val Ile Cys
```

-continued

```
            210                 215                 220
Leu Cys Tyr Leu Leu Ile Val Val Lys Val Arg Ser Thr Thr Arg Arg
225                 230                 235                 240

Val Arg Ala Pro Ser Cys Gln Trp Val Gln Ala Pro Ala Cys Gln Arg
                245                 250                 255

Arg Arg Arg Ser Glu Arg Arg Val Thr Arg Met Val Ala Val Val
            260                 265                 270

Ala Leu Phe Val Leu Cys Trp Met Pro Phe Tyr Leu Asn Ile Val
            275                 280                 285

Asn Val Val Cys Pro Leu Pro Glu Glu Pro Ala Phe Phe Gly Leu Tyr
290                 295                 300

Phe Leu Val Val Ala Leu Pro Tyr Ala Asn Ser Cys Ala Asn Pro Ile
305                 310                 315                 320

Leu Tyr Gly Phe Leu Ser Tyr Arg Phe Lys Gln Gly Phe Arg Arg Ile
                325                 330                 335

Leu Leu Arg Pro Ser Arg Arg Val Arg Ser Gln Glu Pro Gly Ser Gly
            340                 345                 350

Pro Pro Glu Lys Thr Glu Glu Glu Asp Glu Glu Glu Glu Arg
            355                 360                 365

Arg Glu Glu Glu Arg Arg Met Gln Arg Gly Gln Glu Met Asn Gly
370                 375                 380

Arg Leu Ser Gln Ile Ala Gln Pro Gly Pro Ser Gly Gln Gln Gln Arg
385                 390                 395                 400

Pro Cys Thr Gly Thr Ala Lys Glu Gln Gln Leu Leu Pro Gln Glu Ala
                405                 410                 415

Thr Ala Gly Asp Lys Ala Ser Thr Leu Ser His Leu
                420                 425

<210> SEQ ID NO 11
<211> LENGTH: 388
<212> TYPE: PRT
<213> ORGANISM: Homo sapiens

<400> SEQUENCE: 11

Met Ser Ala Pro Ser Thr Leu Pro Pro Gly Gly Glu Gly Leu Gly
1               5                   10                  15

Thr Ala Trp Pro Ser Ala Ala Asn Ala Ser Ser Ala Pro Ala Glu Ala
                20                  25                  30

Glu Glu Ala Val Ala Gly Pro Gly Asp Ala Arg Ala Ala Gly Met Val
            35                  40                  45

Ala Ile Gln Cys Ile Tyr Ala Leu Val Cys Leu Val Gly Leu Val Gly
50                  55                  60

Asn Ala Leu Val Ile Phe Val Ile Leu Arg Tyr Ala Lys Met Lys Thr
65                  70                  75                  80

Ala Thr Thr Ile Tyr Leu Leu Asn Leu Ala Val Ala Asp Glu Leu Phe
                85                  90                  95

Met Leu Ser Val Pro Phe Val Ala Ser Ser Ala Ala Leu Arg His Trp
            100                 105                 110

Pro Phe Gly Ser Val Leu Cys Arg Ala Val Leu Ser Val Asp Gly Leu
            115                 120                 125

Asn Met Phe Thr Ser Val Phe Cys Leu Thr Val Leu Ser Val Asp Arg
            130                 135                 140

Tyr Val Ala Val Val His Pro Leu Arg Ala Ala Thr Tyr Arg Arg Pro
145                 150                 155                 160
```

```
Ser Val Ala Lys Leu Ile Asn Leu Gly Val Trp Leu Ala Ser Leu Leu
                165                 170                 175

Val Thr Leu Pro Ile Ala Ile Phe Ala Asp Thr Arg Pro Ala Arg Gly
            180                 185                 190

Gly Gln Ala Val Ala Cys Asn Leu Gln Trp Pro His Pro Ala Trp Ser
        195                 200                 205

Ala Val Phe Val Val Tyr Thr Phe Leu Leu Gly Phe Leu Leu Pro Val
    210                 215                 220

Leu Ala Ile Gly Leu Cys Tyr Leu Leu Ile Val Gly Lys Met Arg Ala
225                 230                 235                 240

Val Ala Leu Arg Ala Gly Trp Gln Gln Arg Arg Ser Glu Lys Lys
                245                 250                 255

Ile Thr Arg Leu Val Leu Met Val Val Val Phe Val Leu Cys Trp
            260                 265                 270

Met Pro Phe Tyr Val Val Gln Leu Leu Asn Leu Val Val Thr Ser Leu
        275                 280                 285

Asp Ala Thr Val Asn His Val Ser Leu Ile Leu Ser Tyr Ala Asn Ser
    290                 295                 300

Cys Ala Asn Pro Ile Leu Tyr Gly Phe Leu Ser Asp Asn Phe Arg Arg
305                 310                 315                 320

Ser Phe Gln Arg Val Leu Cys Leu Arg Cys Cys Leu Leu Glu Gly Ala
                325                 330                 335

Gly Gly Ala Glu Glu Pro Leu Asp Tyr Tyr Ala Thr Ala Leu Lys
            340                 345                 350

Ser Lys Gly Gly Ala Gly Cys Met Cys Pro Pro Leu Lys Cys Gln Gln
        355                 360                 365

Glu Ala Leu Gln Pro Gly Pro Gly Arg Lys Arg Ile Pro Leu Thr Arg
    370                 375                 380

Thr Thr Thr Phe
385

<210> SEQ ID NO 12
<211> LENGTH: 384
<212> TYPE: PRT
<213> ORGANISM: Rat

<400> SEQUENCE: 12

Met Asn Thr Pro Ala Thr Leu Pro Leu Gly Gly Glu Asp Thr Thr Trp
1               5                   10                  15

Thr Pro Gly Ile Asn Ala Ser Trp Ala Pro Asp Glu Glu Glu Asp Ala
            20                  25                  30

Val Arg Ser Asp Gly Thr Gly Thr Ala Gly Met Val Thr Ile Gln Cys
        35                  40                  45

Ile Tyr Ala Leu Val Cys Leu Val Gly Leu Val Gly Asn Ala Leu Val
    50                  55                  60

Ile Phe Val Ile Leu Arg Tyr Ala Lys Met Lys Thr Ala Thr Asn Ile
65                  70                  75                  80

Tyr Leu Leu Asn Leu Ala Val Ala Asp Glu Leu Phe Met Leu Ser Val
                85                  90                  95

Pro Phe Val Ala Ser Ala Ala Ala Leu Arg His Trp Pro Phe Gly Ala
            100                 105                 110

Val Leu Cys Arg Ala Val Leu Ser Val Asp Gly Leu Asn Met Phe Thr
        115                 120                 125

Ser Val Phe Cys Leu Thr Val Leu Ser Val Asp Arg Tyr Val Ala Val
    130                 135                 140
```

-continued

```
Val His Pro Leu Arg Ala Ala Thr Tyr Arg Arg Pro Ser Val Ala Lys
145                 150                 155                 160

Leu Ile Asn Leu Gly Val Trp Leu Ala Ser Leu Leu Val Thr Leu Pro
            165                 170                 175

Ile Ala Val Phe Ala Asp Thr Arg Pro Ala Arg Gly Gly Glu Ala Val
            180                 185                 190

Ala Cys Asn Leu His Trp Pro His Pro Ala Trp Ser Ala Val Phe Val
            195                 200                 205

Ile Tyr Thr Phe Leu Leu Gly Phe Leu Leu Pro Val Leu Ala Ile Gly
            210                 215                 220

Leu Cys Tyr Leu Leu Ile Val Gly Lys Met Arg Ala Val Ala Leu Arg
225                 230                 235                 240

Ala Gly Trp Gln Gln Arg Arg Arg Ser Glu Lys Lys Ile Thr Arg Leu
                245                 250                 255

Val Leu Met Val Val Thr Val Phe Val Leu Cys Trp Met Pro Phe Tyr
            260                 265                 270

Val Val Gln Leu Leu Asn Leu Phe Val Thr Ser Leu Asp Ala Thr Val
            275                 280                 285

Asn His Val Ser Leu Ile Leu Ser Tyr Ala Asn Ser Cys Ala Asn Pro
290                 295                 300

Ile Leu Tyr Gly Phe Leu Ser Asp Asn Phe Arg Arg Ser Phe Gln Arg
305                 310                 315                 320

Val Leu Cys Leu Arg Cys Cys Leu Leu Glu Thr Thr Gly Gly Ala Glu
                325                 330                 335

Glu Glu Pro Leu Asp Tyr Tyr Ala Thr Ala Leu Lys Ser Arg Gly Gly
            340                 345                 350

Pro Gly Cys Ile Cys Pro Pro Leu Pro Cys Gln Gln Glu Pro Met Gln
            355                 360                 365

Ala Glu Pro Ala Cys Lys Arg Val Pro Phe Thr Lys Thr Thr Thr Phe
            370                 375                 380
```

<210> SEQ ID NO 13
<211> LENGTH: 364
<212> TYPE: PRT
<213> ORGANISM: Homo sapiens

<400> SEQUENCE: 13

```
Met Glu Pro Leu Phe Pro Ala Ser Thr Pro Ser Trp Asn Ala Ser Ser
1               5                   10                  15

Pro Gly Ala Ala Ser Gly Gly Gly Asp Asn Arg Thr Leu Val Gly Pro
            20                  25                  30

Ala Pro Ser Ala Gly Ala Arg Ala Val Leu Val Pro Val Leu Tyr Leu
            35                  40                  45

Leu Val Cys Ala Ala Gly Leu Gly Gly Asn Thr Leu Val Ile Tyr Val
            50                  55                  60

Val Leu Arg Phe Ala Lys Met Lys Thr Val Thr Asn Ile Tyr Ile Leu
65                  70                  75                  80

Asn Leu Ala Val Ala Asp Val Leu Tyr Met Leu Gly Leu Pro Phe Leu
                85                  90                  95

Ala Thr Gln Asn Ala Ala Ser Phe Trp Pro Phe Gly Pro Val Leu Cys
            100                 105                 110

Arg Leu Val Met Thr Leu Asp Gly Val Asn Gln Phe Thr Ser Val Phe
            115                 120                 125

Cys Leu Thr Val Met Ser Val Asp Arg Tyr Leu Ala Val Val His Pro
```

```
                130                 135                 140
Leu Ser Ser Ala Arg Trp Arg Pro Arg Val Ala Lys Leu Ala Ser
145                 150                 155                 160

Ala Ala Ala Trp Val Leu Ser Leu Cys Met Ser Leu Pro Leu Val
                165                 170                 175

Phe Ala Asp Val Gln Glu Gly Gly Thr Cys Asn Ala Ser Trp Pro Glu
                180                 185                 190

Pro Val Gly Leu Trp Gly Ala Val Phe Ile Ile Tyr Thr Ala Val Leu
                195                 200                 205

Gly Phe Phe Ala Pro Leu Leu Val Ile Cys Leu Cys Tyr Leu Leu Ile
210                 215                 220

Val Val Lys Val Arg Ala Ala Gly Val Arg Val Gly Cys Val Arg Arg
225                 230                 235                 240

Arg Ser Glu Arg Lys Val Thr Arg Met Val Leu Val Val Leu Val
                245                 250                 255

Phe Ala Gly Cys Trp Leu Pro Phe Phe Thr Val Asn Ile Val Asn Leu
                260                 265                 270

Ala Val Ala Leu Pro Gln Glu Pro Ala Ser Ala Gly Leu Tyr Phe Phe
                275                 280                 285

Val Val Ile Leu Ser Tyr Ala Asn Ser Cys Ala Asn Pro Val Leu Tyr
                290                 295                 300

Gly Phe Leu Ser Asp Asn Phe Arg Gln Ser Phe Gln Lys Val Leu Cys
305                 310                 315                 320

Leu Arg Lys Gly Ser Gly Ala Lys Asp Ala Asp Ala Thr Glu Pro Arg
                325                 330                 335

Pro Asp Arg Ile Arg Gln Gln Gln Glu Ala Thr Pro Pro Ala His Arg
                340                 345                 350

Ala Ala Ala Asn Gly Leu Met Gln Thr Ser Lys Leu
                355                 360

<210> SEQ ID NO 14
<211> LENGTH: 363
<212> TYPE: PRT
<213> ORGANISM: Rat

<400> SEQUENCE: 14

Met Glu Pro Leu Ser Leu Ala Ser Thr Pro Ser Trp Asn Ala Ser Ala
1               5                   10                  15

Ala Ser Ser Gly Asn His Asn Trp Ser Leu Val Gly Ser Ala Ser Pro
                20                  25                  30

Met Gly Ala Arg Ala Val Leu Val Pro Val Leu Tyr Leu Leu Val Cys
                35                  40                  45

Thr Val Gly Leu Ser Gly Asn Thr Leu Val Ile Tyr Val Val Leu Arg
                50                  55                  60

His Ala Lys Met Lys Thr Val Thr Asn Val Tyr Ile Leu Asn Leu Ala
65                  70                  75                  80

Val Ala Asp Val Leu Phe Met Leu Gly Leu Pro Phe Leu Ala Thr Gln
                85                  90                  95

Asn Ala Val Val Ser Tyr Trp Pro Phe Gly Ser Phe Leu Cys Arg Leu
                100                 105                 110

Val Met Thr Leu Asp Gly Ile Asn Gln Phe Thr Ser Ile Phe Cys Leu
                115                 120                 125

Met Val Met Ser Val Asp Arg Tyr Leu Ala Val Val His Pro Leu Arg
                130                 135                 140
```

| | | | | | | | | | | | | | | |
|---|---|---|---|---|---|---|---|---|---|---|---|---|---|---|
| Ser | Ala | Arg | Trp | Arg | Pro | Arg | Val | Ala | Lys | Met | Ala | Ser | Ala | Ala |
| 145 | | | | | 150 | | | | | 155 | | | | 160 |
| Val | Trp | Val | Phe | Ser | Leu | Leu | Met | Ser | Leu | Pro | Leu | Leu | Val | Phe | Ala |
| | | | | 165 | | | | | 170 | | | | | 175 | |
| Asp | Val | Gln | Glu | Gly | Trp | Gly | Thr | Cys | Asn | Leu | Ser | Trp | Pro | Glu | Pro |
| | | | 180 | | | | | 185 | | | | | 190 | | |
| Val | Gly | Leu | Trp | Gly | Ala | Ala | Phe | Ile | Thr | Tyr | Thr | Ser | Val | Leu | Gly |
| | | 195 | | | | | 200 | | | | | 205 | | | |
| Phe | Phe | Gly | Pro | Leu | Leu | Val | Ile | Cys | Leu | Cys | Tyr | Leu | Leu | Ile | Val |
| | 210 | | | | | 215 | | | | | 220 | | | | |
| Val | Lys | Val | Lys | Ala | Ala | Gly | Met | Arg | Val | Gly | Ser | Ser | Arg | Arg | Arg |
| 225 | | | | | 230 | | | | | 235 | | | | | 240 |
| Arg | Ser | Glu | Pro | Lys | Val | Thr | Arg | Met | Val | Val | Val | Val | Val | Leu | Val |
| | | | | 245 | | | | | 250 | | | | | 255 | |
| Phe | Val | Gly | Cys | Trp | Leu | Pro | Phe | Phe | Ile | Val | Asn | Ile | Val | Asn | Leu |
| | | | 260 | | | | | 265 | | | | | 270 | | |
| Ala | Phe | Thr | Leu | Pro | Glu | Glu | Pro | Thr | Ser | Ala | Gly | Leu | Tyr | Phe | Phe |
| | | 275 | | | | | 280 | | | | | 285 | | | |
| Val | Val | Val | Leu | Ser | Tyr | Ala | Asn | Ser | Cys | Ala | Asn | Pro | Leu | Leu | Tyr |
| | 290 | | | | | 295 | | | | | 300 | | | | |
| Gly | Phe | Leu | Ser | Asp | Asn | Phe | Arg | Gln | Ser | Phe | Arg | Lys | Val | Leu | Cys |
| 305 | | | | | 310 | | | | | 315 | | | | | 320 |
| Leu | Arg | Arg | Gly | Tyr | Gly | Met | Glu | Asp | Ala | Asp | Ala | Ile | Glu | Pro | Arg |
| | | | | 325 | | | | | 330 | | | | | 335 | |
| Pro | Asp | Lys | Ser | Gly | Arg | Pro | Gln | Ala | Thr | Leu | Pro | Thr | Arg | Ser | Cys |
| | | | 340 | | | | | 345 | | | | | 350 | | |
| Glu | Ala | Asn | Gly | Leu | Met | Gln | Thr | Ser | Arg | Ile | | | | | |
| | | | 355 | | | | | 360 | | | | | | | |

<210> SEQ ID NO 15
<211> LENGTH: 665
<212> TYPE: DNA
<213> ORGANISM: Homo sapiens

<400> SEQUENCE: 15

```
gggagacggt tgagagcaca caagccgctt taggagcgag gttcggagcc atcgctgctg     60
cctgctgatc cgcgcctaga gtttgaccag ccactctcca gctcggcttt cgcggcgccg    120
agatgctgtc ctgccgcctc cagtgcgcgc tggctgcgct gtccatcgtc ctggccctgg    180
gctgtgtcac cggcgctccc tcggacccca gactccgtca gtttctgcag aagtccctgg    240
ctgctgccgc ggggaagcag gaactggcca agtacttctt ggcagagctg ctgtctgaac    300
ccaaccagac ggagaatgat gccctggaac tgaagatct gtcccaggct gctgagcagg    360
atgaaatgag gcttgagctg cagagatctg ctaactcaaa cccggctatg caccccgag    420
aacgcaaagc tggctgcaag aatttcttct ggaagacttt cacatcctgt tagctttctt    480
aactagtatt gtccatatca gacctctgat ccctcgcccc cacacccat ctctcttccc    540
taatcctcca gtcttcagc gagacccttg cattagaaac tgaaaactgt aaatacaaaa    600
taaaattatg gtgaaattat gaaaaatgtg aaaaaaaaaa aaaaaaaaaa aaaaaaaaaa    660
aaaaa                                                               665
```

<210> SEQ ID NO 16
<211> LENGTH: 564
<212> TYPE: DNA
<213> ORGANISM: Rat

```
<400> SEQUENCE: 16
tgcggacctg cgtctagact gacccaccgc gctcaagctc ggctgtctga ggcaggggag      60
atgctgtcct gccgtctcca gtgcgcgctg gccgcgctct gcatcgtcct ggctttgggc     120
ggtgtcaccg gggcgccctc ggaccccaga ctccgtcagt ttctgcagaa gtctctggcg     180
gctgccaccg ggaaacagga actggccaag tacttcttgg cagaactgct gtctgagccc     240
aaccagacag agaacgatgc cctggagcct gaggatttgc cccaggcagc tgagcaggac     300
gagatgaggc tggagctgca gaggtctgcc aactcgaacc cagccatggc accccgggaa     360
cgcaaagctg gctgcaagaa cttcttctgg aagacattca catcctgtta gctttaatat     420
tgttgtctca gccagacctc tgatccctct cctccaaatc ccatatctct tccttaactc     480
ccagcccccc ccccaatgct caactagacc ctgcgttaga aattgaagac tgtaaataca     540
aaataaaatt atggtgaaat tatg                                            564

<210> SEQ ID NO 17
<211> LENGTH: 4343
<212> TYPE: DNA
<213> ORGANISM: Homo sapiens

<400> SEQUENCE: 17
tggtcatcgc acggcggcag ctcctcacct ggatttagaa gagctggcgt ccccgcccgc      60
ccaagccttt aaactctcgt ctgccagaac ccgccaactc tccaggctta gggccagttt     120
ccgcgattct aagagtaatt gcgtgggcac ctgtgctggg gccaggcgca aagaagggag     180
ttggtctgcg cgaagatcgt caacctgcta acagaccgca catgcacttt gcaccgacca     240
tctacgtctc agtctggagg ttgcgcactt tggctgctga cgcgctggtg gtgcctatta     300
atcatttacc agtccagagc cgcgccagtt aatggctgtg ccgtgcggtg ctcccacatc     360
ctggcctctc ctctccacgg tcgcctgtgc ccgggcaccc cggagctgca aactgcagag     420
cccaggcaac cgctgggctg tgcgccccgc cggcgccggt aggagccgcg ctccccgcag     480
cggttgcgct ctaccggag gcgctgggcg gctgtgggct gcaggcaagc ggtcgggtgg      540
ggagggaggg cgcaggcggc gggtgcgcga ggagaaagcc ccagccctgg cagccccact     600 ggccccctc agctgggatg ttccccaatg gcaccgcctc ctctccttcc tcctctccta      660
gccccagccc gggcagctgc ggcgaaggcg gcggcagcag gggccccggg gccggcgctg     720
cggacggcat ggaggagcca gggcgaaatg cgtcccagaa cgggacctg agcgagggcc      780 agggcagcgc catcctgatc tctttcatct actccgtggt gtgcctggtg gggctgtgtg     840
ggaactctat ggtcatctac gtgatcctgc gctatgccaa gatgaagacg gccaccaaca     900
tctacatcct aaatctggcc attgctgatg agctgctcat gctcagcgtg cccttcctag     960
tcacctccac gttgttgcgc cactggccct tcggtgcgct gctctgccgc ctcgtgctca    1020
gcgtggacgc ggtcaacatg ttcaccagca tctactgtct gactgtgctc agcgtggacc    1080
gctacgtggc cgtggtgcat cccatcaagg cggcccgcta ccgccggccc accgtggcca    1140
aggtagtaaa cctgggcgtg tgggtgctat cgctgctcgt catcctgccc atcgtggtct    1200
ctctctcgca cgcggccaac agcgacggca cggtggcttg caacatgctc atgccagagc    1260
ccgctcaacg ctggctggtg ggcttcgtgt tgtacacatt tctcatgggc ttcctgctgc    1320
ccgtggggga tatctgcctg tgctacgtgc tcatcattgc taagatgcgc atggtggccc    1380
tcaaggccgg ctggcagcag cgcaagcgct cggagcgcaa gatcacctta atggtgatga    1440
```

```
tggtggtgat ggtgtttgtc atctgctgga tgccttteta cgtggtgcag ctggtcaacg   1500
tgtttgctga gcaggacgac gccacggtga gtcagctgtc ggtcatcctc ggctatgcca   1560
acagctgcgc caaccccatc ctctatggct ttctctcaga caacttcaag cgctcttttcc  1620 aacgcatcct atgcctcagc tggatggaca acgccgcgga ggagccggtt gactattacg   1680
ccaccgcgct caagagccgt gcctacagtg tggaagactt ccaacctgag aacctggagt   1740
ccggcggcgt cttccgtaat ggcacctgca cgtcccggat cacgacgctc tgagcccggg   1800
ccacgcaggg gctctgagcc cgggccacgc aggggccctg agccaaaaga ggggagaat    1860 gagaagggaa ggccgggtgc gaaagggacg gtatccaggg cgccagggtg ctgtcgggat   1920
aacgtggggc taggacactg acagcctttg atggaggaac ccaagaaagg cgcgcgacaa   1980
tggtagaagt gagagctttg cttataaact gggaaggctt tcaggctacc ttttctggg    2040 tctcccactt tctgttcctt cctccactgc gcttactcct ctgaccctcc ttctattttc   2100
cctaccctgc aacttctatc ctttcttccg caccgtcccg ccagtgcaga tcacgaactc   2160
attaacaact cattctgatc ctcagcccct ccagtcgtta tttctgtttg tttaagctga   2220
gccacggata ccgccacggg tttccctcgg cgttagtccc tagccgcgcg gggccgctgt   2280
ccaggttctg tctggtgccc ctactggagt cccgggaatg accgctctcc ctttgcgcag   2340
ccctacccta aggaaagttg gacttgagaa agatctaagc agctggtctt ttctcctact   2400
cttgggtgaa ggtgcatctt tccctgccct cccctgtccc cctctcgccg cccgcccgcc   2460
accaccactc tcactccacc cagagtagag ccaggtgctt agtaaaatag gtcccgcgct   2520
tcgaactcca ggctttctgg agttcccacc caagccctcc tttggagcaa agaaggagct   2580
gagaacaagc cgaatgagga gttttttataa gattgcgggg tcggagtgtg ggcgcgtaat   2640
aggaatcacc ctcctactgc gcgttttcaa agaccaagcg ctgggcgctc ccgggccgcg   2700
cgtctgcgtt aggcagggca gggtagtgca gggcacacct tccccggggt tcggggttcg   2760
gggttcggtt gcagggctgc agcccgcctt ggctttctcc ctcacccaag tttccggagg   2820
agccgaccta aaagtaacaa tagataaggt ttcctgctcc agtgtatctc aaaagaccgg   2880
gcgccagggg cggggggacct agggcgacgt cttcagagtc cgccagtgtt ggcggtgtcg   2940
ccgcaacctg caggctcccg agtggggcct gcctggtctc tagagggttg ctgccttttca  3000 agcggtgcct aagaagttat tttcttgttt aacatatata tttattaatt tatttgtcgt   3060
gttggaaaat gtgtctctgc tttccttttc tctgcttgcc tagccccagg tcttttcttt   3120
gggaccctgg gggcgggcat ggaagtggaa gtagggcaa gctcttgccc cactccctgg    3180
ccatctcaac gcctctcctc aatgctgggc cctcttatct catcctttcc tctagctttt   3240 ctattttttga ttgtgttgag tgaagtttgg agattttca tacttttctt actatagtct    3300
cttgtttgtc ttattaggat aatacataaa tgataatgtg ggttatcctc ctctccatgc    3360
acagtggaaa gtcctgaact cctggctttc caggagacat atataggga acatcaccct    3420 atatataatt tgagtgtata tatatttata tatatgatgt ggacatatgt atacttatct    3480
tgctccattg tcatgagtcc atgagtctaa gtatagccac tgatggtgac aggtgtgagt   3540
ctggctggaa cactttcagt ttcaggagtg caagcagcac tcaaacctgg agctgaggaa   3600
tctaattcag acagagactt taatcactgc tgaagatgcc cctgctccct ctgggttcca   3660
gcagaggtga ttcttacata tgatccagtt aacatcatca ctttttttga ggacattgaa    3720
agtgaaataa tttgtgtctg tgtttaatat taccaactac attggaagcc tgagcagggc   3780
gaggaccaat aattttaatt atttatattt cctgtattgc tttagtatgc tggcttgtac   3840
```

| | |
|---|---|
| atagtaggca ctaaatacat gtttgttggt tgattgttta agccagagtg tattacaaca | 3900 |
| atctggagat actaaatctg gggttctcag gttcactcat tgacatgata tacaatggtt | 3960 |
| aaaatcacta ttgaaaaata cgttttgtgt atatttgctt caacaacttt gtgctttcct | 4020 |
| gaaagcagta accaagagtt aagatatccc taatgttttg cttaaactaa tgaacaaata | 4080 |
| tgctttgggt cataaatcag aaagtttaga tctgtcccct aataaaaata tatattacta | 4140 |
| ctcctttgga aaatagattt ttaatggtta agaactgtga aatttacaaa tcaaaatctt | 4200 |
| aatcattatc cttctaagag gatacaaatt tagtgctctt aacttgttac cattgtaata | 4260 |
| ttaactaaat aaacagatgt attatgctgt taaaaaaaaa aaaaaaaaaa aaaaaaaaa | 4320 |
| aaaaaaaaaa aaaaaaaaaa aaa | 4343 |

<210> SEQ ID NO 18
<211> LENGTH: 3615
<212> TYPE: DNA
<213> ORGANISM: Rat

<400> SEQUENCE: 18

| | |
|---|---|
| gctcgccaca gctgctgcgc gctgccggga gggccaggcg cggtgagctg tgagcttgga | 60 |
| gccttgagcc tagggagggc gcaggcagca agggcgcaag gtgagcgtcc caaccggcgg | 120 |
| ccacaccggc ccacttcagc tgggatgttc cccaatggca ccgccccctc tcccacctct | 180 |
| tctcccagct ccagcccagg cggctgcggg gaaggagtct gcagcagggg tcccgggtcc | 240 |
| ggcgctgcgg acggcatgga agaacctgga cgaaactctt cccagaacgg gactttaagc | 300 |
| gagggtcagg gtagcgccat tctcatctct ttcatctact ccgtggtatg cttggtggga | 360 |
| ctgtgtggga actccatggt catttacgtg atcctgcgct acgccaagat gaagaccgca | 420 |
| accaacatct acattctaaa cctggccatt gctgatgagc tgctcatgct cagcgtgccc | 480 |
| tttctggtca cttccacgct gttgcgccac tggccctttg gcgcgctact ttgccgcctg | 540 |
| gtgctcagcg tggatgcagt caacatgttc accagcatct actgtctgac tgtgcttagt | 600 |
| gtggaccgct atgtggctgt ggtgcacccg atcaaggcag cgcgctaccg tcggcccact | 660 |
| gtggccaaag tagtgaacct gggcgtgtgg gtgctgtcgc tactggttat cttgcccatc | 720 |
| gtggtcttct cacgcaccgc agccaacagc gatggcacgg tggcctgcaa catgctcatg | 780 |
| cccgagcccg cccagcgctg gttggtgggc ttcgtcttat acacatttct catgggcttc | 840 |
| ctgctgcctg tcggggccat ctgcctgtgt tacgtgctca tcattgccaa gatgcgcatg | 900 |
| gtggccctca aggccggctg gcagcagcgc aagcgctcag agcgcaagat cactctaatg | 960 |
| gtgatgatgg tggtgatggt ttttgtcatc tgctggatgc cttctacgt ggtacagcta | 1020 |
| gtcaacgtgt tcgccgagca agacgacgcc acggtgagcc agttgtctgt catcctcggc | 1080 |
| tatgccaata gctgtgccaa ccccatcctc tacggcttcc tgtcggacaa cttcaagcgc | 1140 |
| tctttccagc gcatcctgtg cctcagctgg atggataacg ctgcggagga gcctgttgac | 1200 |
| tactacgcca ctgccctgaa gagtcgtgcc tacagtgtgg aggacttcca gcctgagaat | 1260 |
| ctggaatctg gaggcgtttt ccgtaatggc acctgcgctt ccaggatcag cacgctttga | 1320 |
| ggccggacgc taaccggagg gggagagtgg tcagaaaggt ggagagggga agcaggtggg | 1380 |
| agggaatgat agccgcacac caggtgctat gggagtagtg cgtgacagcg atgcagcgcc | 1440 |
| cctgtttagc aaagctatgt gactaaggta acgggagag atttgagaat gttttcgggc | 1500 |
| catctggtat tctgaactgt gttctccaaa cccgataatt tccatcctcc ctcccagttc | 1560 |

```
tgctagtaca aactgcaaac ttaacgtcgc caactccgtt tgacccttc cctctcaagc    1620
tgttatttct gcttctttaa actgagccat cttgtgttc ttttgggctg agtccccacc    1680
ttgcgctgaa cccctgcgc aggtcagcgg ccagactct tcagagcggc taccagactg    1740
tccccagtta ccgctcccct tttgcacagc cttactgtca agtaagccca gctccaggat    1800
gaccaggcaa ctggtctttt ctactctcaa agaaggcacc atcttcct gggcccttc     1860
tctgcttcac tgcatccaga gcagagctgg gtgcttaaga aaaagtcctg tgcccagatg    1920
gccagacttg tgtagtccc acccattccc tcctttggag cacaaaaagg agctaagagc    1980
cagcagaagg gcaagtttct aagattcctg ggctgtggtt gtgggtgcca gagaagccac    2040
cctcccatag agctcaggac ctgagcacta gcttggagg tcccagctag gggagctccc    2100
ggcttgtgaa taacttatgc accctggtgt gtgaacctga attgcacagc agttcccctt    2160
ggaggtctcc ctagaataac aaaggattgg gttgcctgct cccttccta gtccagctcc    2220
tgttccagtg acaaaccgca gagccctgc caaagctgga tggctaactt cagcttgtct    2280
ggtccctgac atttttgcc tttcaagcgg tgcctaataa gttatttctt gtttgacata    2340
tttattat tattatggt gttgaaaaaa aagtgtgtt tccactttct ttttctgtat      2400
ttgcctaaca gggctgttct tgagaatcct ctggcaggca cgtggtggtg tggaggtgtg    2460
gagggggagca ggggtggaga aagttctctc accccaagac tccctcagaa gttcccttc    2520
ttttgcactc cattggcctt tcttgatcc ttcttggttt tgcttgtgtc cagtgaagtt     2580
tggagatttt aaaaatatat ttttactgta gttttgtctt gttaaaataa gtacatggca    2640
atttggttta acttttgtca gtgtggagtg gaaggcctga atccctggca tcccagaaaa    2700
cacaggggaa caaatcacat gatccgtgat gtatgtctgt atatgtgctg tcacacacaa    2760
gtcacatata tacgtgtata tatatatcat atatgtacac acacatataa aggtagattt    2820
gtcaatcttg acaactgtca ctagttcatg acaattataa ggacacccac aatgtgtgac    2880
ctgagctgta gcactccagc tgggatctga gaaacgtcag agattggagt cgctgctgaa    2940
gatgctgctg ccttttcta tccctcaga ggtgatctt acccagtaag tctagtcact    3000
tttgttgagg aatggaagcg aaacaattgt gtctgcattt actgactacc gtggaaacct    3060
gaacacggaa ggacccatct cttcacttgt tgcatttgct gtgttcctgt gtatgctcgt    3120
ttgtacatag gggccactga aaggatatct tgcttggttg tttaaggaag ccagtgtata    3180
tcagtggtct tagaacaatg aacctggggt tctcgggtcc acagtgacct gacatctaac    3240
ctgcaatggt cgaatgcact gttgaaaatg tgtttgtg tacatttgct tcaagaacac    3300
atccatgctt ttcctaaaag caggaaccaa gagttaaact gtctcttctg ttttgtttaa    3360
ataaatgaac aaatatgctt ttgatcataa gtgagaaagt ttagatcttt tcctaagaat    3420
agtatatata tatatatata tgtatatata tatatatata tatgtatata tatatacttt    3480
tctgttaatt agatttttta accgataaga agagtgaact ttataaactg aaatctccat    3540
cattatcatc tcgacaggat aaaaatgtag tgctcttacc ctgtaatagt aactgaataa    3600
aaagatgtat tatgc                                                    3615

<210> SEQ ID NO 19
<211> LENGTH: 2996
<212> TYPE: DNA
<213> ORGANISM: Homo sapiens

<400> SEQUENCE: 19
cgcagccacc catgcgcgcg cgctcgcaag accaccagcg cccagagccc cagtctgagg      60
```

-continued

```
cttggcgccg ggggtctgcg ggcgagggga gctctctacg tgcgaggggc tagcgggagc    120
cggcacaaga gggtcgagga gccaggaacc ccaaacgtcc ggcgccaggc gctagccaag    180
ctgctgcgcg ccccggcgcc cagctggctc ggggacagcc gctgggtgtc ggagaccgga    240
gctagcggat tgcagcggaa aagcaaagat gtcacactgg atccttggcc tccagggtcc    300
attaaggtga aataagatc tctgggctgg ctggaactag cctaagactg aaaagcagcc     360
atggacatgg cggatgagcc actcaatgga agccacacat ggctatccat tccatttgac    420
ctcaatggct ctgtggtgtc aaccaacacc tcaaaccaga cagagccgta ctatgacctg    480
acaagcaatg cagtcctcac attcatctat tttgtggtct gcatcattgg gttgtgtggc    540
aacacacttg tcatttatgt catcctccgc tatgccaaga tgaagaccat caccaacatt    600
tacatcctca acctggccat cgcagatgag ctcttcatgc tgggtctgcc tttcttggct    660
atgcaggtgg ctctggtcca ctggcccttt ggcaaggcca tttgccgggt ggtcatgact    720
gtggatggca tcaatcagtt caccagcatc ttctgcctga cagtcatgag catcgaccga    780
tacctggctg tggtccaccc catcaagtcg gccaagtgga ggagaccccg gacgcccaag    840
atgatcacca tggctgtgtg gggagtctct ctgctggtca tcttgcccat catgatatat    900
gctgggctcc ggagcaacca gtgggggaga agcagctgca ccatcaactg gccaggtgaa    960
tctggggctt ggtacacagg gttcatcatc tacactttca ttctggggtt cctggtaccc    1020
ctcaccatca tctgtctttg ctacctgttc attatcatca aggtgaagtc ctctggaatc    1080
cgagtgggct cctctaagag gaagaagtct gagaagaagg tcacccgaat ggtgtccatc    1140
gtggtggctg tcttcatctt ctgctggctt cccttctaca tattcaacgt ttcttccgtc    1200
tccatggcca tcagccccac cccagccctt aaaggcatgt ttgactttgt ggtggtcctc    1260
acctatgcta acagctgtgc caaccctatc ctatatgcct tcttgtctga caacttcaag    1320
aagagcttcc agaatgtcct ctgcttggtc aaggtgagcg gcacagatga tggggagcgg    1380
agtgacagta agcaggacaa atcccggctg aatgagacca cggagaccca gaggaccctc    1440
ctcaatggag acctccaaac cagtatctga actgcttggg gggtgggaaa gaaccaagcc    1500
atgctctgtc tactggcaat gggctcccta cccacactgg cttcctgcct cccacccctc    1560
acacctggct tctagaatag aggattgctc agcatgagtc caattcagag aacggtgttt    1620
gagtcagctt gtctgattga atgataatgt gctaaattga ttacctcccc cttaaagcga    1680
acactgaaat gcaggtagac aattcaaagt ctggagaaga gggatcatgc ctggatatga    1740 tcttttagaaa caacaaaaat agaaaaaaat aagtatctgt gtgtttgtgt attgaaaact    1800
caatatgtaa tcttgtgttt ttatatgtat acttgtatat tcctatttat tctctgtata    1860
ggcattacct acgttcctgt gtttacatac acaagtagca aattcgagta tgcatagtgt    1920
agatggacat ttgccacaac acactgcccg cagaaatgga cttaccgtga agccaataaa    1980
gttcaagctt cagggatctc tcttgcacgg gccttgccaa ggcccaggag ggacttgggc    2040
agtatgttca tgtggtcata tgttttgta aaaaattgtg aaagtaagat atgtttgtat     2100
tgtttttctt aaagaggaac ctcgtataag cttcaagcct cacaaacctt ctagcctctg    2160
cccttgggga tttgcttcat taatttcagg caagtgaggt caatgtaaga agggaaaggg    2220
agaagatatt tgaagaacca gaatgtaaat tcatgtgttt ccacttctca gatatagtca    2280
gagaattatt catttgccca aaaggactta agtggttgtg gtcatccatc attgtattta    2340
tcaagacaaa gccaactttg ttataagatt gcatttttt cttttcaaat tgctttagtt     2400
```

-continued

```
tttcttaggg agctatgagg gggaaaaatc actaacatga aaggcaaaaa atggactatg    2460
attcctgtgg ggaaacaatt tcattctctc catcgtgaaa ataagtgaat aagagtgaag    2520
caaaattaca cctttatgag aaaccataaa attgttttta tttttcaggc cagacatagc    2580
ttcctaatga aagaaaatgg aaatgtaatt cgacgactcc tcaaggggga ctttagagga    2640
cttcatacaa agctgggcat taagaaaacc acaatgcatg ccgggcgtg gtggcttaca     2700 cctgtaatcc cagcactttg ggaggccgag gtgggtggat cacccgaggt caggagttcg    2760
agaccagcct ggccaacatg gtgaaacccc atcactacta aaaatatgta aattagtcgg    2820
gcgtggtgtc acgtgcctgt aatcctagct gctcggagg ctgaggcagg agaatcactt     2880
gaacttggga ggtggaggtt gcagtaagct gagattgtgc cactgcactc tagcctgagc    2940
aacaagagca aaactcagtc tcaaaaaaaa aaaaaaaaa aaaaaaaaaa aaaaaa         2996
```

<210> SEQ ID NO 20
<211> LENGTH: 2116
<212> TYPE: DNA
<213> ORGANISM: Rat

<400> SEQUENCE: 20

```
gccaccggca cgctggcgag gccaccggcc ctggagcacc agtccgccgc tgggcgtcga      60
tgatctacag gccagggtag ctctactggg gcccaggcaa gctctctcag acgccaggag     120
ggccagcacg agccagactg ggaagctgcg agcccgagag ctactgcgga gcgccaaaca    180
ccccctaaac ctgctgcgct cccggccgcc cggctgggta aggacagct tctgggagct      240 agagaacaca gagaagcgag tgctcgtgga aaagcaagat gtcacgatag acccttggcc    300
ccagagtcca ctgaggtgag aggaagatct ctgggctgct tggttctagg cggactgaag    360
agcagccatg gagttgacct ctgagcagtt caatgggagc caagtgtgga taccttctcc    420
ctttgacctc aacggctcac tggggccaag caatggctcc aaccagacag agccatacta    480
cgacatgaca agcaacgcgg tcctcacgtt catctacttc gtggtgtgcg tggtggggct    540
gtgcggcaac acgctcgtca tctacgtcat cctccgctac gccaagatga aaaccatcac    600
caacatttac atcctcaacc tggccatcgc agatgaactc ttcatgctgg ggctgccctt    660
cttggccatg caggtggcgc tggtccactg gcctttggc aaggccatct gccgggtggt     720
catgactgtg gacggtatca accagttcac cagtatcttc tgcttgacgg tcatgagcat    780
cgaccgttac ctggccgtgg tccaccccat taagtcagcc aaatggaggc gaccccggac    840
agccaagatg atcaacgtgg ctgtgtgggg tgtgtccctg cttgtcattt tgcccatcat    900
gatatacgct ggcctccgga gcaaccagtg gggtaggagc agctgcacca tcaactggcc    960
gggcgaatcc ggggcatggt acacgggttt cattatctat gccttcatcc tggggttcct   1020
ggtaccccta accatcatct gtctctgcta cctgttcatc atcatcaagg tgaagtcctc   1080
tgggatccga gtggggtcgt ccaagaggaa aaagtcagag aaaaaggtga cccgaatggt   1140
atccatcgtg gtggctgtct tcatcttctg ctggctcccc ttctatatct tcaatgtctc   1200
gtccgtgtct gtgccatca gccccacccc tgccctgaaa ggcatgtttg actttgtggt    1260
tatcctcacc tacgccaaca gctgcgccaa ccccatcctg tacgccttct tgtccgacaa   1320
cttcaagaag agcttccaga atgttctttg cttggtcaag gtgagtggtg cggaggatgg   1380
ggagcggagc gacagtaagc aggacaaatc ccggctgaat gagaccacgg agacccagag   1440
gaccctcctc aatggagacc tccaaaccag tatctgaaac aacccgggaa cgcaacgtgc   1500
acacgcacta gccaagcccc gcctcctggc agtgcgagcc ccattcaccc gcttcctgcc   1560
```

```
tcccctaccc atcacacccg gcttttctag agcagagcgg atttgagtct ggcttgtccg     1620
aaagtatacc cctctggtca catctacccc taaagtgaac gttttcgtgc aggcagacaa     1680
ttcaaagact ggagaagagg acacgatggc ctgggtgtga cccggtggaa agcagctacc     1740
cggcagaaac cggaaaaacc aaaactaaaa tcaaagttcc gcgcgtgtac gtgtgcttgc     1800
ccgctatgta atctcgtgat ctgatatttc cgtttgtaca tcacctcccc accccaccc     1860 cggtctctgc ggagccagta tacacgtgtc ctgtgtttgt aaacccaagt agctagttca     1920
tgtgcgtcta gtataggtgg acatttacca cagcgctgaa cctgacgaca aggactcacc     1980
atgtcagagt caatctaatc taagcttcca gcatccctct tgcatgggcc tttcccagac     2040
ccaggaggag catgagcagt atgttcatat aataatacat ttttgtaaaa agaaaaaaaa     2100
aaaaaaaaaa aaaaaa                                                     2116

<210> SEQ ID NO 21
<211> LENGTH: 2123
<212> TYPE: DNA
<213> ORGANISM: Homo sapiens

<400> SEQUENCE: 21
cgcatctctc atcactcccc ctcattctgc ctttcctcct actcacggtc tcctctccct       60
ctccctctct ctctctcccc ctccctcttt ctctctctct ctctttctcc acctcctccc      120
gacccccttt cccctctatt tctattggct tctgtgtccc ttgctcccct cttctcttcc      180
tcaccctggg aagcttctcc cccctatcct tgccccctgcc cccccaggat gtgtcctgga      240
gatggggggt gacgtaccag gctctggttg ggaagtcagg gccggagacc agatgggaga      300
ggctctgtgg acagccgtgg ccgagggcct gggagggaac ctgagcccgc aagcggtcta      360
gaagtgggtg ccgtgtgggg accctagtta ggagtgccct gggggcacct ggggactggg      420
cagggagagg ggacagcaga atgataacca gcctggcggc aaggagggaa gccctcaccc      480
catgggcagg caaatagctg actgctgacc accctcccct cagccatgga catgcttcat      540
ccatcatcgt tgtccacgac ctcagaacct gagaatgcct cctcggcctg gcccccagat      600
gccaccctgg gcaacgtgtc ggcgggccca agcccggcag ggctggccgt cagtggcgtt      660
ctgatccccc tggtctacct ggtggtgtgc gtggtgggcc tgctgggtaa ctcgctggtc      720
atctatgtgg tcctgcggca cacggccagc ccttcagtca ccaacgtcta catcctcaac      780
ctggcgctgg ccgacgagct cttcatgctg gggctgccct tcctgccgc ccagaacgcc      840 ctgtcctact ggcccttcgg ctccctcatg tgccgcctgg tcatggcggt ggatggcatc      900
aaccagttca ccagcatatt ctgcctgact gtcatgagcg tggaccgcta cctggccgtg      960
gtacatccca cccgctcggc ccgctggcgc acagctccgg tgcccgcac ggtcagcgcg      1020 gctgtgtggg tggcctcagc cgtggtggtg ctgcccgtgg tggtcttctc gggagtgccc      1080
cgcggcatga gcacctgcca catgcagtgg cccgagccgg cggcggcctg gcgagccggc      1140
ttcatcatct acacggccgc actgggcttc ttcgggccgc tgctggtcat ctgcctctgc      1200
tacctgctca tcgtggtgaa ggtgcgctca gctgggcgcc gggtgtgggc accctcgtgc      1260
cagcggcggc ggcgctccga acgcaggtc acgcgcatgg tggtggccgt ggtggcgctc      1320
ttcgtgctct gctggatgcc cttctacgtg ctcaacatcg tcaacgtggt gtgcccactg      1380
cccgaggagc ctgccttctt tgggctctac ttcctggtgg tggcgctgcc ctatgccaac      1440
agctgtgcca accccatcct ttatggcttc ctctcctacc gcttcaagca gggcttccgc      1500
```

```
agggtcctgc tgcggccctc ccgccgtgtg cgcagccagg agcccactgt ggggcccccg    1560
gagaagactg aggaggagga tgaggaggag gaggatgggg aggagagcag ggagggggggc   1620 aaggggaagg agatgaacgg ccgggtcagc cagatcacgc agcctggcac cagcgggcag    1680
gagcggccgc ccagcagagt ggccagcaag gagcagcagc tcctaccccca agaggcttcc   1740 actggggaga agtccagcac gatgcgcatc agctacctgt agggcctggg gaaagccagg    1800
atggcccgag gaagaggcag aagccgtggg tgtgcctagg gcctacttcc caaggtgcca    1860
caggcccatg atgggatgtt gaggggcctg gactttgatg ctattgctgc caggtcttgc    1920
tgtgtgacct tgggtaggtt gcttctactc tctgggcctt gttttctcct ctgtgactca    1980
gggataggag tcatcagcct ggatgagcta tgtcagatga gaggtttgga gggcactgtt    2040
gctgggctga cctggctgag caggcaaaag gtgggtgcag actggcctcc ccccagggat    2100
ggagtgtctt ggggcatcaa cta                                            2123

<210> SEQ ID NO 22
<211> LENGTH: 3985
<212> TYPE: DNA
<213> ORGANISM: Rat

<400> SEQUENCE: 22
caggcgtctc tccttactcc ccctcattct gcctttccgc ccacacactg tctcctctcc      60
ctctcctctc tctctctcca cctccgaccc tcccctcct ttccttattt tcctcggcct      120
tcttatgtcc cctgctatct cacatttctg tcatctttgg aagtgccttc tgtcaccccc     180
aactgggtgc catctgaaga ccccccatcct gtgtccggca cccgccacgt gtcctggaga    240
tggggggtga cgtatcaggt gcgggtggca agtcaggact gaggaccaga tgggagaggc     300
gacgtgggct gacgtggccc ccgaggacct aggaagggcc caaccaagcc cacaagcact    360
ggaggagtgg gcactgtgtg tcaccccagc tggctgtgct ctggtggtac ctggctgcag    420
aaggttatcc agcctggcga ctgcaaaggg aattcttgcc ctgtgggcag aatcttggaa    480
cctccatgca gcagaatgtc agaactggac caaagagatg caagctaccc atggcttccc    540
aggccttgag cacccccctca tgctggcagt ggtgcatctg aagagtccct tccacctttg     600 cagcaaccccc gtaaggtttg gctagttgg ctgctgactg atcctcatcc ctgccatggc    660
cgctgttacc tatccttcat ccgtgcctac gaccttggac cctgggaatg catcctcagc    720
ctggcccctg acacgtcccc tggggaatgc atctgctggc actagcctgg caggactggc    780
tgtcagtggc atcttgatct ctctggtgta cctggtggtg tgtgtggtgg gtttgctggg    840
caattcactg gtgatctacg tggttctgcg gcacacgtcc agcccatcag tgaccagtgt    900
ctatatcctc aacctggcac tggctgacga actcttcatg ctgggctac ctttcctggc    960 tgctcagaac gccctgtcct actggccttt cggctctctc atgtgtcgtc tggtcatggc    1020
cgtggatggc atcaaccagt tcaccagcat cttctgcctc accgtcatga gtgtggaccg    1080
ctacctggct gtggtgcacc ccacacgctc tgcccgctgg cgcacggcac tgtggctcg    1140 aatggtcagt gcagctgtct gggtggcctc agctgtggtc gtgctgcctg tggttgtgtt   1200
ctcaggagtg cccccgaggga tgagcacgtg ccacatgcag tggccagagc cagcggctgc    1260
ctggcgaaca gccttcatca tctatacggc cgcactgggc ttttttgggc ccctgctggt    1320
catctgctta tgctacctgc ttattgtggt gaaggtgcgg tcgaccacac ggcgggtgcg    1380
ggcgccctcg tgccagtggg tacaggcacc cgcttgccag cggcggcggc gctctgagcg    1440
cagggtgaca cgcatggtgg tggctgtggt ggcactcttc gtcctctgct ggatgccttt    1500
```

```
ctatttactc aacatcgtta atgtggtgtg cccgctgccg gaggagcccg ccttctttgg   1560
cctctacttc ctggtggtcg cgctgcccta cgccaacagc tgcgcaaacc ccatcctcta   1620
cggcttcctc tcctaccgct tcaagcaggg cttccgcagg atcctgctaa gaccttctcg   1680
gcgagtacgg agccaggagc cagggtctgg ccctccagag aagacggagg aggaggagga   1740
tgaagaggaa gaagagagaa gggaagagga gagcggagg atgcagagag ggcaggagat    1800
gaatgggagg ctcagtcaga tcgcacagcc aggccccagt ggacagcagc aacggccttg   1860
cacagggact gccaaggaac agcagcttct accccaggaa gccacagctg ggacaaggc    1920 cagcacgctg agccatctgt aagaaccttc aaagagccag catgatcctg aagagagcag   1980
aagctatgct tgacctaagg cacgagtacc agacacatgg cagtgttcta agcaagcaac   2040
agctagagtg agcttattta catggctgtc ctggccctct ctggaccgtt gtggtactag   2100
ggtccagtga tggaatgtcc ataggcctgg gctctgtccc actgtgccag gcttgctgt    2160 gtatactttg gccagtcact agccctctct gggtcttgtt ttcttctttt gactcaggga   2220
tgggtaaaat gagccctgtc agaagagggg tctggaatcc ttattgggat taatctccta   2280
atcagagccc aagttaagaa tttgcacagt ctgaccaaga aacaagatat cttggggatc   2340
agtctgtatc ttggccctca aggagataca ccagggcttg ggaaatcaga gatgcagatg   2400
acctgggggt gggtgcttgg ctgaaaccta aggaagtgt tagttggtgt ggtgggatgc    2460
cacggcttag gacgcaagtg agcccttttcc atgctgctct gtggcctcag ccactctgtt   2520
catgtgcagg cctcctacct cttctgcagg gcagtccggg tgtcctacag accctcaccc   2580
cagcgtctga gcattgggcc ttctgtgctc ctggacacca ggggaagaac ttcccagaag   2640
gcaggtgaaa ccaagtttca gggggttcttg ctgcttgggc cccctggga cctacgtgtg     2700 actggtcttc taattttgta ttccttctct ggagggaaga ttgcacacca ccaggctcag   2760
gccacccgga gactgactca ccctattcag gtcagctacc tagtccccag ggctatgcag   2820
cagcctgagg gaaggagagg gagaaaggag gagagggagc tgaggcagta agaagaggag   2880
ggggatggga tcgagggag aagagaacag aactttgtgg tgatcttgag tcaaccttct     2940
cccccttgag ctaagctcag tttgcagcac tgatggtttc aggaaggatc tgaaggagac   3000
atgtgaccag atcccctgg agggtgcgtg ggctggtga gaggggcaca ggtcatgatg     3060
gagtcgtggg aatgggcttg gctcctcagg agggatggta agtcctttgt gtgggtcagt   3120
cctcccatcc tctattccca gggctccagc tgatgtagag actaacaggc tgtcatgggg   3180
agtagccact gtcccagctg ggtcaggact tcattcttcc cctcccagag atggtccttc   3240
tggtcccagc agtgatggcc ctggaaaggt tgaggcttct gctcaaaccc ccaccctacc   3300
ctgcagaggc agggttctca gggaacccac aaatccagat gttgagaaag ctggatcttc   3360
tattcacctc aagcctcttg gccataccct ctgtctctgc gcctcagtat cctcatcata   3420
gtgagaatgt gatccccag ttctccagtc tgttagaatc caggagggaa ctgagtcatg     3480
ccaggcaagc tactgctcac cacaatgggg ctgcgtaagg atacaaagcg gccgtgttgt   3540
acctcaggct cagcccacac cttgcccttt aagtgagtgg cttcggtgtc agctactgga   3600
ggtgaaggta ttcatgagaa atggagtgca ggaggtcaga agccaaggac catggagaat   3660
gcaagccacc ccagaaggag gaagtttgca aacataggca tgtatgggc ctgaggccca    3720 gcccaggggt tcctctgaga aggagctggg tcaggaagta agcagtccaa ccttcctgga   3780
tggggtaggt gagccacgtc ttgcaaaggg gtgggtgacc agttgagaag ttctttgctg   3840
```

```
cttctgacct gagctcctgt caataaagat agtgactaag aaaaaaaaaa aaaaaaaaaa    3900
aaaaaaaaaa aaaaaaaaaa aaaaaaaaaa aaaaaaaaaa aaaaaaaaaa aaaaaaaaaa    3960
aaaaaaaaaa aaaaaaaaaa aaaaa                                          3985
```

<210> SEQ ID NO 23
<211> LENGTH: 1167
<212> TYPE: DNA
<213> ORGANISM: Homo sapiens

<400> SEQUENCE: 23

```
atgagcgccc cctcgacgct gccccccggg ggcgaggaag ggctggggac ggcctggccc      60
tctgcagcca atgccagtag cgctccggcg gaggcggagg aggcggtggc ggggcccggg     120
gacgcgcggg cggcgggcat ggtcgctatc cagtgcatct acgcgctggt gtgcctggtg     180
gggctggtgg gcaacgccct ggtcatcttc gtgatccttc gctacgccaa gatgaagacg     240
gctaccacca tctacctgct caacctggcc gtagccgacg agctcttcat gctgagcgtg     300
cccttcgtgg cctcgtcggc cgccctgcgc cactggccct tcggctccgt gctgtgccgc     360
gcggtgctca gcgtcgacgg cctcaacatg ttcaccagcg tcttctgtct caccgtgctc     420
agcgtggacc gctacgtggc cgtggtgcac cctctgcgcg cggcgaccta ccggcggccc     480
agcgtggcca agctcatcaa cctgggcgtg tggctggcat ccctgttggt cactctcccc     540
atcgccatct tcgcagacac cagaccggct cgcggcggcc aggccgtggc ctgcaacctg     600
cagtggccac accggcctg gtcggcagtc ttcgtggtct acacttttcct gctgggcttc     660 ctgctgcccg tgctggccat tggcctgtgc tacctgctca tcgtgggcaa gatgcgcgcc     720
gtggccctgc gcgctggctg gcagcagcgc aggcgctcgg agaagaaaat caccaggctg     780
gtgctgatgg tcgtggtcgt ctttgtgctc tgctggatgc ttttctacgt ggtgcagctg     840
ctgaacctcg tcgtgaccag ccttgatgcc accgtcaacc acgtgtccct tatcctcagc     900
tatgccaaca gctgcgccaa ccctattctc tatggcttcc tctccgacaa cttccgccga     960
tccttccagc gggttctctg cctgcgctgc tgcctcctgg aaggtgctgg aggtgctgag    1020
gaggagcccc tggactacta tgccactgct ctcaagagca aggtggggc agggtgcatg    1080 tgccccccac taaatgcca gcaggaagcc ctgcaaccag aacccggccg caagcgcatc    1140
cccctcacca ggaccaccac cttctga                                        1167
```

<210> SEQ ID NO 24
<211> LENGTH: 1865
<212> TYPE: DNA
<213> ORGANISM: Rat

<400> SEQUENCE: 24

```
gttcagcgtt cggctgctct ccacggcaat ccgctgcccc gggtgggcac cccgaagcat      60
gaacacgcct gcaactctgc ccctgggggg cgaggacacc acctggaccc ctgggatcaa     120
cgccagctgg gctccggatg aggaggagga tgcagtgcgg tccgacggca cggggacagc     180
gggcatggta actatccagt gcatctatgc gctcgtgtgt ctggtgggcc tggtaggaaa     240
cgccctggtc atattcgtga tcctacgcta tgccaaaatg aagacagcca ccaacatcta     300
cctgctcaac ctggccgtcg ctgatgagct cttcatgctc agtgtgccat ttgtggcctc     360 ggcgctgcc ctcgccact ggccgttcgg ggcggtgctg tgccgcgcag tgcttagtgt     420
ggacggcctt aacatgttca cgagtgtctt ctgcctcaca gtgctcagcg tggatcgcta     480
tgtggctgta gtgcaccctc tgcgagctgc cacctaccgg cggcccagcg tggccaagct     540
```

```
aatcaacctg ggagtgtggc tagcatcctt gctggtcacc ctgcccatcg cagtcttcgc    600
tgacactagg ccagctcgtg ggggtgaggc agtagcttgc aacctgcact ggcctcaccc    660
ggcctggtct gcagtctttg tgatctatac ttttttgctg gcttcctac tcccggttct    720 ggctatcgga ttatgttacc tgcttatcgt gggcaagatg cgtgctgtgg ccctgcgggc    780
tggctggcaa caacggaggc gctcagagaa gaagatcact aggctcgtgc taatggtggt    840
gactgtcttt gtgctatgct ggatgccatt ctatgtagtg cagcttctga atctgtttgt    900
caccagcctc gatgccactg tcaaccatgt gtccctcatc ctcagctatg ccaacagctg    960
tgccaacccg attctctatg gtttcctctc agacaacttc cgacgctctt ccagcgggt    1020 tctgtgcctg cgctgctgtc tcctggaaac aactggaggt gctgaggaag agcccctgga    1080
ctactatgct actgctctca aaagcagagg tggcccagga tgcatatgcc tccattgcc     1140 ctgccagcag gagcccatgc aagcagaacc tgcctgcaag cgagtccctt tcaccaagac    1200
cactactttc tgaaaaccat ttcaccctcc ctcagcccac ctgcaagcag gtctgcacca    1260
cactctcaag ccagcaactt caagaaaact cctgttgtca ctaagccagg ccctttcagc    1320
agcctgtgtt ctgtccctag gagcctcagg actcctgcta gcccctgcct ctcctaggac    1380
tgactggctc caaggacaac tccgtggggg taggacttct ctgggttttg gctagagta    1440 ccatccatcc tttcctggac ctctagcaat ttttcaagag gcaggaagca ggtggtggtc    1500
agaaagggat gcctacccct gtgtgacttg tgacagtgac tgcttggaag agcgctggga    1560
gggtgaggta ggcagagcta ggctctctgc tgtgtggtag catagggcat acggtgatac    1620
aggggagaag atatgatacc tccaagtgtt ttccctctgt gtctgtctga gtctcttgtt    1680
gctaaatgag atgtctacgc aacagctgaa agcatttgct ttcccaaggc aaatgttct    1740 ccagttgtca aaggaccagt agcagacttc ctgcgaatgc aaatgtttaa agaaggatgg    1800
tgtggggcgt ttttgaaaa aaaaaataat tctgatttct ggtcaggaat taaaaggcag    1860
aaagg                                                                 1865
```

<210> SEQ ID NO 25
<211> LENGTH: 1095
<212> TYPE: DNA
<213> ORGANISM: Homo sapiens

<400> SEQUENCE: 25

```
atggagcccc tgttcccagc ctccacgccc agctggaacg cctcctcccc gggggctgcc     60
tctggaggcg gtgacaacag gacgctggtg gggccggcgc cctcggcagg ggcccgggcg    120
gtgctggtgc ccgtgctgta cctgctggtg tgtgcgccg gctgggcgg gaacacgctg    180 gtcatctacg tggtgctgcg cttcgccaag atgaagaccg tcaccaacat ctacattctc    240
aacctggcag tggccgacgt cctgtacatg ctggggctgc cttttcctggc cacgcagaac    300 gccgcgtcct tctggccctt cggccccgtc ctgtgccgcc tggtcatgac gctggacggc    360
gtcaaccagt tcaccagtgt cttctgcctg acagtcatga gctgtgaccg ctacctggca    420
gtggtgcacc cgctgagctc ggcccgctgg cgccgcccgc gtgtggccaa gctggcgagc    480
gccgcggcct gggtcctgtc tctgtgcatg tcgctgccgc cctggtgtt cgcggacgtg    540 caggagggcg gtacctgcaa cgccagctgg ccggagcccg tggggctgtg gggcgccgtc    600
ttcatcatct acacggccgt gctgggcttc ttcgcgccgc tgctggtcat ctgcctgtgc    660
tacctgctca tcgtggtgaa ggtgagggcg gcgggcgtgc gcgtgggctg cgtgcggcgg    720
```

-continued

```
cgctcggagc ggaaggtgac gcgcatggtg ttggtggtgg tgctggtgtt tgcgggatgt      780
tggctgccct tcttcaccgt caacatcgtc aacctggccg tggcgctgcc ccaggagccc      840
gcctccgccg gcctctactt cttcgtggtc atcctctcct acgccaacag ctgtgccaac      900
cccgtcctct acggcttcct ctctgacaac ttccgccaga gcttccagaa ggttctgtgc      960
ctccgcaagg gctctggtgc caaggacgct gacgccacgg agccgcgtcc agacaggatc     1020
cggcagcagc aggaggccac gccgcccgcg caccgcgccg cagccaacgg gcttatgcag     1080
accagcaagc tgtga                                                      1095
```

<210> SEQ ID NO 26
<211> LENGTH: 1384
<212> TYPE: DNA
<213> ORGANISM: Rat

<400> SEQUENCE: 26

```
ccgacttcgt acagcaatcg agtgagcaca ctgctctttg agcccgagtg cgctgcctaa       60
ctgcgaagta ccgccgccgt gcccgccccg gcgtgggcac cctgtcctgc acagagacac      120
gcgtggtctg gcacccggcc tgaagctgac agcatggagc ccctctctct ggcctccaca      180
ccaagctgga atgcctcggc tgcttccagt ggtaaccata actggtcact ggtgggctca      240
gcatcgccaa tgggagcccg ggcagtatta gtgcctgtgc tctacctgtt ggtgtgcacc      300
gtgggactga gtggaaatac actggtcatt tatgtggtgc tgcggcacgc caagatgaag      360
acagttacta acgtgtacat cctgaacctg gccgtggctg acgtattatt tatgttggga      420
cttcctttcc tggccacgca gaacgccgtc gtctcctact ggcccttcgg ctccttcttg      480
tgccgcctgg tcatgacact ggatggcatc aaccagttca ccagtatctt ctgcctgatg      540
gtcatgagtg ttgaccgcta cctggccgtg gtccaccctc tccgctcagc ccggtggcgt      600
cgcccacggg tagccaagat ggccagcgcg gccgtctggg tcttttcgct gctcatgtct      660
ctgccgctct tggtcttcgc ggatgtccag gagggctggg gcacctgcaa cctgagctgg      720
ccagagcctg tggggctgtg gggtgcagcc ttcatcacct acgtctctgt gttgggcttc      780
tttgggcccc tgctggtcat ctgcttgtgc tacctgctca ttgtggtcaa ggtgaaggct      840
gcaggcatgc gcgtaggctc ctcaaggcgg aggcgctcgg agccgaaggt gactcgcatg      900
gtggtggtcg tggtgctggt gtttgtgggc tgctggctgc ctttcttcat tgtcaacatc      960
gtcaacctgg ccttcacact gcccgaggaa cccacatctg ccggcctcta tttctttgtg     1020
gtggtcctat cttatgccaa tagctgtgcc aaccccctgc tctacggctt tctctcggac     1080
aacttccgcc agagcttccg gaaggttctg tgcctacgta gaggatacgg tatggaggat     1140
gcggacgcca tagagccacg gccagacaag agtgggcggc tcaggccac actgcccaca     1200 cgcagctgcg aggccaatgg gctcatgcag accagcagga tttgaatgcc cctgtaacac     1260
cctgggggtc ctccaggcct ccacggtgtt gtcttctggg atctgagagt ttgctgagat     1320
gcattcaccc ccaggcctac aagttggact cctctcggtg gcagtgtgaa gacaggacct     1380
gcag                                                                 1384
```

<210> SEQ ID NO 27
<211> LENGTH: 6
<212> TYPE: PRT
<213> ORGANISM: Artificial Sequence
<220> FEATURE:
<223> OTHER INFORMATION: Synthetic - AC-178,335

<400> SEQUENCE: 27

```
His Phe Ile Arg Trp Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic - BIM 23,458
<220> FEATURE:
<221> NAME/KEY: MISC_FEATURE
<222> LOCATION: (1)..(1)
<223> OTHER INFORMATION: Xaa = Fpa (4-fluorophenylalanine)
<220> FEATURE:
<221> NAME/KEY: MISC_FEATURE
<222> LOCATION: (3)..(3)
<223> OTHER INFORMATION: Xaa = Pal (3-pyridylalanine or
      B-[3-pyridyl]-alanine)
<220> FEATURE:
<221> NAME/KEY: MISC_FEATURE
<222> LOCATION: (6)..(6)
<223> OTHER INFORMATION: Xaa = Tle (tert-leucine or a-[t-butyl]-glycine)
<220> FEATURE:
<221> NAME/KEY: MISC_FEATURE
<222> LOCATION: (8)..(8)
<223> OTHER INFORMATION: Xaa = Nal (3-(2-naphthyl)alanine)

<400> SEQUENCE: 28

Xaa Cys Xaa Trp Lys Xaa Cys Xaa
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic - BIM 23,627
<220> FEATURE:
<221> NAME/KEY: MISC_FEATURE
<222> LOCATION: (3)..(3)
<223> OTHER INFORMATION: Xaa = Pal (3-pyridylalanine or
      B-[3-pyridyl]-alanine)
<220> FEATURE:
<221> NAME/KEY: MISC_FEATURE
<222> LOCATION: (8)..(8)
<223> OTHER INFORMATION: Xaa = Nal (3-(2-naphthyl)alanine)

<400> SEQUENCE: 29

Phe Cys Xaa Trp Lys Val Cys Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic - BIM 23,454
<220> FEATURE:
<221> NAME/KEY: MISC_FEATURE
<222> LOCATION: (1)..(1)
<223> OTHER INFORMATION: Xaa = Cpa (3-(4-chlorophenyl)alanine)
<220> FEATURE:
<221> NAME/KEY: MISC_FEATURE
<222> LOCATION: (3)..(3)
<223> OTHER INFORMATION: Xaa = Pal (3-pyridylalanine or
      B-[3-pyridyl]-alanine)
```

```
<220> FEATURE:
<221> NAME/KEY: MISC_FEATURE
<222> LOCATION: (8)..(8)
<223> OTHER INFORMATION: Xaa = Nal (3-(2-naphthyl)alanine)

<400> SEQUENCE: 30

Xaa Cys Xaa Trp Lys Val Cys Xaa
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic - D-Tyr8-CYN 154806

<400> SEQUENCE: 31

Phe Cys Tyr Trp Lys Thr Cys Tyr
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic - L-Tyr8-CYN 15806

<400> SEQUENCE: 32

Phe Cys Tyr Trp Lys Thr Cys Tyr
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic - PRL-2915
<220> FEATURE:
<221> NAME/KEY: MISC_FEATURE
<222> LOCATION: (1)..(1)
<223> OTHER INFORMATION: Xaa = Cpa (3-(4-chlorophenyl)alanine)
<220> FEATURE:
<221> NAME/KEY: MISC_FEATURE
<222> LOCATION: (3)..(3)
<223> OTHER INFORMATION: Xaa = Pal (3-pyridylalanine or
      B-[3-pyridyl]-alanine)
<220> FEATURE:
<221> NAME/KEY: MISC_FEATURE
<222> LOCATION: (6)..(6)
<223> OTHER INFORMATION: Xaa = Tle (tert-leucine or a-[t-butyl]-glycine)
<220> FEATURE:
<221> NAME/KEY: MISC_FEATURE
<222> LOCATION: (8)..(8)
<223> OTHER INFORMATION: Xaa = Nal (3-(2-naphthyl)alanine)

<400> SEQUENCE: 33

Xaa Cys Xaa Trp Lys Xaa Cys Xaa
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic - PRL-2970
<220> FEATURE:
```

```
<221> NAME/KEY: MISC_FEATURE
<222> LOCATION: (1)..(1)
<223> OTHER INFORMATION: Xaa = Cpa (3-(4-chlorophenyl)alanine)
<220> FEATURE:
<221> NAME/KEY: MISC_FEATURE
<222> LOCATION: (8)..(8)
<223> OTHER INFORMATION: Xaa = Nal (3-(2-naphthyl)alanine)

<400> SEQUENCE: 34

Xaa Cys Tyr Trp Lys Thr Cys Xaa
1               5
```

METHOD OF CONTROLLING TIGHT BLOOD GLUCOSE BY SOMATOSTATIN RECEPTOR ANTAGONISTS

This application claims the benefit under 35 USC §119(e) of U.S. provisional application No. 60/890,965 filed Feb. 21, 2007.

FIELD OF THE INVENTION

The present disclosure relates to controlling tight blood glucose levels in an insulin-dependent diabetic subject. In particular, the disclosure relates to the treatment or prevention of insulin-induced hypoglycemia in diabetic subjects. The disclosure also relates to the treatment and prevention of idiopathic hypoglycemia or hypoglycemia resulting from an insulinoma in a subject in need thereof. In particular, the disclosure relates to methods and uses of somatostatin inhibitors to increase the glucagon and cortisol response, but may also apply to other hormones in patients that suffer from defective counterregulation.

BACKGROUND OF THE INVENTION

The main characteristic of diabetes is hyperglycemia. Chronic hyperglycemia induces severe complications of diabetes: retinopathy, cataracts, peripheral neuropathy, nephropathy, and vascular angiopathy. It is also a major health problem such that the rate of morbidity and mortality of diabetes is third greatest after cancer and cardiovascular disease. It is important to note that diabetic patients have a much higher incidence of cardiovascular disease than non-diabetics. It was proven that the better the control of blood glucose, the lesser the complications of diabetes. The main acute complication in type 1 diabetes is hypoglycemia. This problem has been greatly enhanced by introduction of tight glucose control. Because of the threat of hypoglycemia, many patients will relax their glucose control in order to minimize the problem of hypoglycemia, which then increases the threat of chronic complications. Thus, hypoglycemia is the limiting factor in the treatment of type 1 diabetes. In addition, many non-diabetic subjects suffer from episodes of hypoglycemia of unknown etiology. One of the main problems in diabetic subjects is defective counterregulation (mainly glucagon, epinephrine, norepinephrine, and cortisol responses) to hypoglycemia.

The initial abnormal counterregulatory response in diabetes (1) is diminished glucagon responsiveness. This is paradoxical because the glucagon response to neurogenic stress (2;3) and exercise (4-7) is normal. One explanation for the discrepancy between hypoglycemia and other stress responses is that the α-cell becomes more sensitive to the inhibitory effect of insulin in diabetes because in type 1 diabetes, most β-cells are destroyed. The sensitivity of α-cells during hypoglycemia improves when normoglycemia is achieved by chronic phloridzin, but not by insulin treatment in diabetic rats (1). This is not surprising because it is well known that insulin inhibits glucagon synthesis and release (8). It is suggested that insulin released from β-cells acts directly on α-cells. It is known that α-cells have insulin receptors. When insulin binds to those receptors, a cytosolic receptor ($GABA_AR$) is translocated to the cell membrane. This induces membrane depolarization and consequently, glucagon secretion is suppressed (9;10). When hypoglycemia is induced with insulin in clinical investigations in non-diabetic subjects, glucagon secretion promptly increases and consequently, normal blood glucose is restored. This occurs because low blood glucose by itself increases glucagon release, and this effect is stronger than the inhibitory action of insulin on α-cells. In contrast, in type 1 diabetic subjects, there are very few or no β-cells in the pancreas, and therefore α-cells become sensitized to insulin. Under those conditions, the effect of an increased amount of insulin in the blood is much stronger than the effect of low blood glucose. Therefore, in diabetic patients which are insulin treated, insulin's effect on the α-cell is much stronger than the effect of blood glucose, and consequently, during hypoglycemia, the glucagon response is either greatly decreased or absent.

One additional possibility for the increased α-cell sensitivity to insulin is the augmented amount of somatostatin in the pancreas in diabetic animals (11;12) as well as in diabetic humans (13). In streptozotocin (STZ)-diabetic rats, there is: (1) hyperplasia and hypertrophy of somatostatin-containing δ-cells in the pancreas (13), (2) increased expression of pancreatic prosomatostatin mRNA (14;15), (3) increased pancreatic somatostatin (1), (4) distribution of somatostatin-secreting δ-cells in the central portions of islets cells (16).

The present inventors were the first to suggest 17 years ago that excessive somatostatin may inhibit glucagon release during hypoglycemia (11). It is well documented that somatostatin inhibits stimulated secretion of pancreatic glucagon.

In STZ-diabetic rats, the expression of the gene for proglucagon and pro-somatostatin are both markedly increased (15). This increased concentration of somatostatin is observed in diabetic rats, both during euglycemia (i.e. normal blood glucose concentrations) and hypoglycemia (1). Concentration of somatostatin in plasma is also increased during euglycemia and hypoglycemia in diabetic rats (1). However, despite increased gene expression of proglucagon, plasma concentrations of glucagon are not increased during hypoglycemia in diabetic rats, presumably in part due to the marked elevation of somatostatin levels.

Somatostatin receptors are ubiquitously expressed in most tissues of the body. So far, 5 different subtypes of somatostatin receptors have been discovered. It is not desirable to inhibit all somatostatin receptors, which may cause unfavourable side effects. The localization of particular receptor subtypes on different tissues allows for specific receptor antagonists to exert specific inhibitory effects. For protection against hypoglycemia, the most important is inhibition of somatostatin receptors related to counterregulatory hormone release which are found in the pancreas, adrenal gland, and hypothalamus of the brain. Somatostatin receptor type 2 (SSTR2) are found in these tissues. Within the pancreas, SSTR2 are found nearly exclusively on glucagon-secreting α-cells in rodents (16,17). In humans as well, somatostatin exerts its inhibitory effect on glucagon secretion via SSTR2 found on α-cells (18,19). In the adrenal gland, SSTR2 have been widely identified in the adrenal medulla of animals and humans (20,21). It has been shown that somatostatin inhibits acetylcholine-stimulated release of epinephrine from the adrenal medulla (22,23), and this is the mechanism whereby epinephrine is released during hypoglycemia (24). SSTR2 are also found in the hypothalamus of the brain (25,26) where somatostatin also has an inhibitory effect on hormones involved in hypoglycemic counterregulation.

In isolated islets and in perifused isolated islets, the somatostatin receptor type 2 (SSTR2)-selective antagonist, DC-41-33, also known as PRL2903 dose-dependently increases glucagon secretion to an arginine stimulus, and subsequently adding somatostatin dose-dependently reverses the actions of the SSTR2 antagonist (27;28). In isolated, perfused pancreas of non-diabetic rats, this antagonist enhances glucagon secretion without affecting insulin secretion (28). It is also able to reverse the inhibitory effect of glucose-dependent insulinotropic polypeptides, GIP and GIP-(1-30)$NH_2$, and glucagon-like polypeptide, GLP-1(7-36)$NH_2$, on pentagastrin-stimulated gastric acid secretion in non-diabetic rats (29).

Previous experiments (28) showed the effect of the SSTR antagonist in isolated islets and pancreas (in vitro and ex vivo) but not in vivo. The effect of any SSTR antagonist has never been tested in diabetic animals. Since the glucagon response to a variety of stresses is normal in diabetic animals, including humans, and the defect is only noted during insulin-induced hypoglycemia in animals, including humans, it is essential to test the effect of any somatostatin, or somatostatin receptor, antagonist in animal models of type 1 diabetes and in diabetic humans.

Somatostatin receptor antagonists are described in U.S. Pat. No. 4,508,711 (April 1985, Coy et al.) and in U.S. Pat. No. 5,846,934 (December 1998, Bass et al.). They showed that these antagonists can increase the release of growth hormone, insulin, and glucagon. These antagonists were never tested in diabetic animals and humans, and it was not known whether these antagonists are effective during hypoglycemia when glucagon release is markedly decreased because of the enhanced sensitivity to β-cells to insulin.

Somatostatin also inhibits the secretions of corticotrophin-releasing hormone (CRH) and adrenocorticotrophic hormone (ACTH), and cortisol (i.e. hypothalamo-pituitary-adrenal (HPA) function) (30). Thus, it is of clinical interest to investigate the effect of SSTR antagonists on counterregulatory HPA hormone responses during hypoglycemia. The question of whether SSTR antagonists can improve or normalize the response of glucocorticoids to hypoglycemia or other stresses has never been investigated before. The present inventors have previously shown that carbachol, an analog of acetylcholine, injected into the third ventricle (icv) of dogs (a model of stress) increases the release of cortisol (2). However, when somatostatin was infused icv concurrently with carbachol, the cortisol responses were abolished in both non-diabetic and diabetic dogs (2;31). Therefore, a SSTR antagonist could enhance the release of cortisol also through a central mechanism and provide a mechanism whereby an SSTR2 antagonist also markedly increased the corticosterone response to hypoglycemia in diabetic rats. An additional possibility is an enhancement of corticosterone through SSTRs in the adrenal cortex, although literature has yet to report SSTR in the corticosterone synthesizing fasciculata and reticularis zonae of the adrenal cortex (32-35).

Since the α-cell is excessively sensitive to insulin in diabetic animals and humans, the key question is whether in an animal model of type 1 diabetes a somatostatin or SSTR antagonist can increase glucagon release. Hypoglycemia is the main limiting factor of intensive insulin treatment. A pharmaceutical approach which could decrease the danger of hypoglycemia would improve glycemic control in diabetic patients and could thus diminish the risk of other complications of diabetes.

Most type 1 diabetic patients suffer from frequent episodes of low blood glucose. This problem is exaggerated with tight control of blood glucose induced by frequent insulin administration. Tight control of blood glucose is necessary to minimize the danger of life-threatening diabetic complications. The danger of hypoglycemia, however, limits the possibility of desired tight control.

SUMMARY OF THE INVENTION

The present inventors have demonstrated that the response of counterregulatory hormones can be normalized in diabetic subjects by inhibiting the action of somatostatin, thereby reducing the threat of hypoglycemia. In particular, the present inventors have shown that somatostatin receptor (SSTR) antagonists may be used to improve or normalize the glucagon response to hypoglycemia in diabetic rats. The present disclosure is directed at improving glucagon release when plasma glucose levels are low due to excessive amounts of exogenous insulin. The present inventors have shown that with euglycemia, the inhibition of somatostatin does not alter plasma glucose levels, which is desirable. This is desirable because the original purpose of exogenous insulin treatment in type 1 diabetic patients is to maintain stringent control of plasma glucose levels. Therefore, having an antagonist that would increase plasma glucose levels during euglycemia would be undesirable.

Accordingly, the present disclosure provides the use of a somatostatin inhibitor for controlling tight blood glucose levels in a subject in need thereof. The present disclosure also provides the use of a somatostatin inhibitor for preparing a medicament for controlling tight blood glucose levels in a subject in need thereof. The present disclosure further provides a method for controlling tight blood glucose levels comprising administering a somatostatin inhibitor to a subject in need thereof.

In another embodiment, the present disclosure provides the use of a somatostatin inhibitor for treating or preventing hypoglycemia in a subject in need thereof. The present disclosure also provides the use of a somatostatin inhibitor for preparing a medicament for treating or preventing hypoglycemia in a subject in need thereof. Further, the present disclosure provides a method for treating or preventing hypoglycemia comprising administering a somatostatin inhibitor to a subject in need thereof.

In one embodiment, the subject is an insulin-dependent diabetic subject. In another embodiment, the subject suffers from idiopathic hypoglycemia. In a further embodiment, the subject has an insulinoma tumor.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 indicates levels of plasma glucose levels in four groups of rats during the 1-h SSTR antagonist (DC-41-33)/saline pretreatment and 3-h hypoglycemic clamp experiment. FIG. 1A shows plasma glucose concentrations during the hypoglycemic clamp experiment using an insulin dose of 10 U/kg and SSTR antagonist (DC-41-33) dose of 1500 nmol/kg/h. A similar glycemic profile is observed in FIG. 1B when another dose of insulin and SSTR antagonist (DC-41-33) were tested (5 U/kg and 3000 nmol/kg/h, respectively).

FIG. 2 shows the effect of hypoglycemia induced with 10 U/kg insulin injection on plasma glucagon levels. SSTR antagonist (DC-41-33) dose was 1500 nmol/kg/h.

FIG. 3 shows infusion of a smaller dose of insulin (5 U/kg). A larger dose of SSTR antagonist (DC-41-33) (3000 nmol/kg/h) was also used to see if the response in diabetic rats could be augmented.

FIG. 4 indicates the responses of corticosterone during hypoglycemia when insulin dose was 10 U/kg and SSTR antagonist (DC-41-33) was 1500 nmol/kg/h. Non-diabetic rats (N-ctrl) responded to hypoglycemia, but there was no response in diabetic rats (D-ctrl). With SSTR antagonist (DC-41-33) treatment, corticosterone response was augmented to the same extent in both non-diabetic (N+SSTRa) and diabetic (D+SSTRa) rats.

FIG. 5 shows the corticosterone response to hypoglycemia when insulin dose was 5 U/kg and SSTR antagonist (DC-41-33) was 3000 nmol/kg/h. Corticosterone response was again lower in diabetic (D-ctrl) than in non-diabetic (N-ctrl) rats, but with SSTR antagonist (DC-41-33), the corticosterone response was fully normalized in diabetic rats (D+SSTRa).

FIG. 6 demonstrates the effect of somatostatin receptor type 2 antagonism on glucose infusion requirement during 3 h of hypoglycemia when 5 U/kg insulin and 3000 nmol/kh/h SSTR antagonist (DC-41-33) were used.

FIG. 7 demonstrates that SSTR antagonist (DC-41-33) (1500 nmol/kg/h) given to diabetic rats dramatically increased (4-fold, AUC) plasma epinephrine levels in response to hypoglycemia (insulin: 10 U/kg).

FIG. 8 indicates that there was no effect of the SSTR antagonist (DC-41-33) (1500 nmol/kg/h) on plasma norepinephrine, neither during basal infusion of SSTR antagonist (DC-41-33) nor during insulin-induced hypoglycemia (insulin: 10 U/kg).

FIG. 9 shows that a growth hormone response to hypoglycemia (insulin: 5 U/kg) was not observed in diabetic or non-diabetic rats.

DETAILED DESCRIPTION OF THE INVENTION

The inventors were the first to demonstrate that in diabetic rats, a somatostatin receptor type (SSTR) 2 antagonist can normalize responses of glucagon and corticosterone in insulin-induced hypoglycemia. An effective glucagon response to hypoglycemia can rapidly increase glucose production by the liver, and thus normoglycemia can be quickly restored. During prolonged episodes of hypoglycemia, glucocorticoids increase glucose production by the liver and decrease glucose utilization in many tissues. Normalization of increases of both hormones is ideal for control of blood glucose levels in diabetic patients. Thus, this novel pharmacological approach could have an effect on a number of counterregulatory hormones during hypoglycemia. The most important counterregulatory hormones are glucagon, epinephrine, cortisol (in humans) or corticosterone (in rodents), norepinephrine, and, under some conditions, growth hormone. The primary purpose of this approach therefore is to increase the response of these counterregulatory hormones during insulin-induced hypoglycemia in diabetic patients as these hormones will act to restore normal glucose levels. It is also important for safety reasons that the administration of an SSTR antagonist does not affect the basal levels of these counterregulatory hormones in individuals (either diabetic or non-diabetic populations) not experiencing hypoglycemia. This is because increased basal levels of counterregulatory hormones would increase the amount of insulin needed to achieve optimal glucose control in insulin-treated diabetics. The data indicate that the antagonist does not substantially increase basal concentration of these hormones.

Accordingly, the present disclosure provides the use of a somatostatin inhibitor for controlling tight blood glucose levels in a subject in need thereof. The present disclosure also provides the use of a somatostatin inhibitor for preparing a medicament for controlling tight blood glucose levels in a subject in need thereof. The present disclosure further provides a method for controlling tight blood glucose levels comprising administering an effective amount of a somatostatin inhibitor to a subject in need thereof.

The present disclosure also provides a method of treating or preventing hypoglycemia comprising administering an effective amount of a somatostatin inhibitor to a subject in need thereof. The present disclosure also provides the use of a somatostatin inhibitor for treating or preventing hypoglycemia in a subject in need thereof. The present disclosure also provides the use of a somatostatin inhibitor for preparing a medicament for treating or preventing hypoglycemia in a subject in need thereof.

Hypoglycemia is a term understood in the art to mean a blood glucose level below normal. Normal fasting blood glucose levels fall within the range of 4.0 to 6.0 mM, and fed levels in non-diabetic individuals are $\leq 7.0$ mM. In one embodiment, a hypoglycemic blood glucose level is considered to be <4.0 mM. Hypoglycemic coma can occur below 2.0 mM. In the present experiments, the target range of hypoglycemia was 2.75±0.25 mM.

The term "controlling tight blood glucose levels" means minimizing the time that the blood glucose level is above or below the normal blood glucose level of 4.0 to 6.0 mM in a subject.

The term "treating hypoglycemia" as used herein means improving or increasing the glucagon response or improving or increasing the corticosterone response. In one embodiment, treating hypoglycemia means raising the blood glucose level back to normal glucose levels (i.e. 4.0 to 6.0 mM). The term "preventing hypoglycemia" as used herein means maintaining a normal blood glucose level (i.e. 4.0 to 6.0 mM) when insulin is administered.

Hypoglycemia can be insulin-induced in a diabetic subject. Accordingly, in one embodiment, the subject is an insulin-dependent diabetic subject. In another embodiment, the diabetic subject suffers from type I diabetes. In yet another embodiment, the diabetic subject suffers from type II diabetes.

Some non-diabetic individuals suffer from low blood glucose (hypoglycemia) of unknown origin. This is called idiopathic hypoglycemia. These patients suffer from occasional hypoglycemia which may be prevented by use of chronic treatment with a somatostatin inhibitor. The inhibitor increases the release of counterregulatory hormones, which consequently increases glucose production by the liver and inhibits glucose uptake by peripheral tissues, thereby minimizing or preventing such hypoglycemic episodes. Accordingly, in another embodiment, the subject suffers from idiopathic hypoglycemia.

Insulinoma is a malignant tumour of the pancreas that produces excessive amounts of insulin. Therefore, blood glucose is low for most of the time. Chronic treatment using a somatostatin inhibitor prevents hypoglycemia in patients suffering from insulinoma. The patients do not require the inhibitor after the tumour has been removed. If the tumour cannot be removed, or if there are metastases, the inhibitor is used as an adjunct to other treatment modalities of the metastatic cancer. Accordingly, in a further embodiment, the subject has an insulinoma.

In one embodiment, the subject is an animal. The term "animal" includes all members of the animal kingdom, preferably a mammal, and more preferably, a human.

A person skilled in the art would readily be able to determine if an individual suffers from type 1 or type 2 diabetes. For example, an individual's blood glucose levels can be measured in order to determine if they are diabetic. Diabetes is diagnosed if fasting plasma glucose is >7.0 mM on 2 separate occasions. Normal fasting glucose is considered between 4.0 and 6.0 mM, and impaired fasting glucose ("pre-diabetes") is between 6.0 and 7.0 mM. Diabetes is also diagnosed if the 2 hour plasma glucose is >11.1 mM after a 75 g oral glucose tolerance test. A random glucose of >11.1 mM with symptoms of hyperglycemia on one occasion is also considered diagnostic of diabetes. Type 1 diabetes can be distinguished from type 2 diabetes using available criteria, such as those of the American Diabetes Association (36). An insulin-dependent diabetic as used herein means a diabetic subject whose blood glucose is controlled by insulin.

The predominant form of somatostatin released from pancreas, brain, and stomach is designated SST-14. SST-14 is a peptide having the amino acid sequence Ala-Gly-Cys-Lys-Asn-Phe-Phe-Trp-Lys-Thr-Phe-Thr-Ser-Cys (SEQ ID NO:1) and is cyclized by a disulfide bond between the cysteine residues. The predominant form of somatostatin in the intestines is designated SST-28 and has an amino acid sequence Ser-Ala-Asn-Ser-Asn-Pro-Ala-Met-Ala-Pro-Arg-Glu-Arg-Lys-Ala-Gly-Cys-Lys-Asn-Phe-Phe-Trp-Lys-Thr-Phe-Thr-Ser-Cys (SEQ ID NO:2) and is cyclized by a disulfide bond between the cysteine residues. The full human and rat pre-protein sequences are shown in Table 1, and the nucleic acid sequences are shown in Table 4.

There are 5 somatostatin receptors having a chromosomal localization and tissue distribution as shown in Table 2. The amino acid sequences of the human and rat somatostatin receptors are shown in Table 3 and the nucleic acid sequences are shown in Table 5.

A "somatostatin inhibitor" as used herein includes any substance that is capable of inhibiting the expression or activity of somatostatin and thus, includes substances that inhibit somatostatin or the interaction of somatostatin with the somatostatin receptor. Such inhibitors optionally include antisense nucleic acid molecules, proteins, antibodies (and fragments thereof), small molecule inhibitors and other substances. In a preferred embodiment, the somatostatin inhibitor is targeted to the pancreas.

Accordingly, in one embodiment, the somatostatin inhibitor is an antisense nucleic acid of the somatostatin nucleic acid sequence shown in SEQ ID NO:15 or SEQ ID NO:16. In another embodiment, the somatostatin inhibitor is an antisense nucleic acid of the somatostatin receptor nucleic acid sequence shown in any one of SEQ ID NOs:17-26. In a particular embodiment, the somatostatin inhibitor is an antisense nucleic acid of the somatostatin receptor 2 nucleic acid sequence as shown SEQ ID NO:19 or SEQ ID NO:20.

The term "antisense nucleic acid" as used herein means a nucleic acid that is produced from a sequence that is inverted relative to its normal presentation for transcription. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

In one embodiment, the somatostatin inhibitor is an antibody that binds to the somatostatin protein having the amino acid sequence as shown in any one of SEQ ID NOs:1-4. In another embodiment, the somatostatin inhibitor is an antibody that binds to the somatostatin receptor having the amino acid sequence as shown in any one of SEQ ID NOs: 5-14. In a particular embodiment, the antibody is specific to the somatostatin receptor 2 having the amino acid sequence as shown in SEQ ID NO:7 or SEQ ID NO:8.

The term "antibody" as used herein is intended to include fragments thereof which also specifically react with a somatostatin or a somatostatin receptor. Antibodies can be fragmented using conventional techniques and the fragments screened for utility in the same manner as described below. For example, $F(ab')_2$ fragments can be generated by treating antibody with pepsin. The resulting $F(ab')_2$ fragment can be treated to reduce disulfide bridges to produce Fab' fragments.

Conventional methods can be used to prepare antibodies. For example, by using a somatostatin or peptide from a somatostatin receptor, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (37) as well as other techniques such as the human B-cell hybridoma technique (38), the EBV-hybridoma technique to produce human monoclonal antibodies (39) and screening of combinatorial antibody libraries (40). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for a somatostatin or somatostatin receptor.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a somatostatin or somatostatin receptor protein (See, for example, Morrison et al. (41), and Takeda et al. (42), and the patents of Cabilly et al., U.S. Pat.

No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a somatostatin or somatostatin receptor as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al. (43), Kozbor et al. (38); Olsson et al. (44) and PCT Publication WO92/06193 or EP 0239400). Humanized antibodies can also be commercially produced (Scotgen Limited, 2 Holly Road, Twickenham, Middlesex, Great Britain).

Specific antibodies, or antibody fragments, reactive against a somatostatin or somatostatin receptor may also be generated by screening expression libraries encoding immunoglobulin genes, or portions thereof, expressed in bacteria with peptides produced from the nucleic acid molecules encoding a somatostatin or somatostatin receptor. For example, complete Fab fragments, VH regions and FV regions can be expressed in bacteria using phage expression libraries (See for example Ward et al. (45), Huse et al. (40) and McCafferty et al (46)).

Antibodies may also be prepared using DNA immunization. For example, an expression vector containing a nucleic acid encoding a somatostatin or somatostatin receptor may be injected into a suitable animal such as mouse. The protein will therefore be expressed in vivo and antibodies will be induced. The antibodies can be isolated and prepared as described above for protein immunization.

The somatostatin inhibitors include SSTR antagonists. The term "antagonist" as used herein means any molecule that is capable of blocking or decreasing the amount of ligand binding to the receptor, or a molecule that binds to the ligand such that signaling through the receptor is diminished or abolished. "SSTR antagonist" as used herein means an antagonist of a somatostatin receptor, including SSTR2. "SSTR2 antagonist" as used herein is an SSTR antagonist that has a higher affinity or selectivity for SSTR2 compared to other types of SSTRs.

Accordingly, in an embodiment, the somatostatin inhibitor is an SSTR antagonist. In one embodiment, the somatostatin inhibitor is a SSTR2 antagonist. In another embodiment, the SSTR2 antagonist is a peptide. Peptide antagonists of SSTR2 are known in the art and have been described widely in the literature (47-49) (all of which are herein incorporated in their entirety by reference) and in a number of patents and patent applications that claim binding with one or more somatostatin subtype receptors including SSTR2. These include but are not limited to the novel cyclic peptide antagonists disclosed in U.S. Pat. No. 4,508,711; U.S. Pat. No. 4,505,897; PCT application WO02072602; US Application No. 24181032A1; US Application No. 28020970A1; and PCT application WO02072602 by Coy et al. (all of which are herein incorporated in their entirety by reference). In addition, Morgan, Murphy and Coy also disclose other somatostatin receptor antagonists based on a variable octapeptide structures in PCT Application WO09824807 (incorporated in its entirety by reference). Similarly, Bass et al have disclosed other novel cyclic peptides that are SSTR2 antagonists in U.S. Pat. No. 5,846,934 and Baumbach et al have also disclosed a number of different structures that include cyclic peptides in U.S. Pat. No. 5,925,618 (both of which are incorporated herein in their entirety by reference). A listing of some disclosed SSTR antagonists is given in Table 6 and a subset of these antagonists is provided in Table 7.

Accordingly, in one embodiment, the somatostatin inhibitor is an SSTR antagonist having a peptide as listed in peptide nos.: 27-436 of Table 6. In another embodiment, the somatostatin inhibitor is an SSTR antagonist having a peptide as listed in peptide nos.: 27-120 of Table 6. In another embodiment, the somatostatin inhibitor is an SSTR antagonist having a peptide sequence as shown in SEQ ID NOs. 27-34 (Table 7). In yet a further embodiment, the SSTR antagonist is a cyclic-octapeptide as shown in SEQ ID NO:28: H-Fpa-cyclo[DCys-Pal-DTrp-Lys-Tle-Cys]-Nal-NH2 also known as DC-14-33. Each embodiment includes an equivalent pharmaceutical salt thereof.

In another embodiment, the somatostatin inhibitor is a SSTR2 antagonist based on small molecule organic structures. In particular, Hay et al have disclosed a number of different somatostatin antagonists and agonists that act at the SST subtype 2 receptor in the following patents: U.S. Pat. No. 6,495,589; U.S. Pat. No. 6,696,418; U.S. Pat. No. 6,720,330 and related applications: US21047030A1, US22016289A1, US22091090A1, US22091125A1, US22128206A1, US24157834A1 and US25054581A1 (all of which are herein incorporated in their entirety by reference). Similarly, Carpino et al disclose a number of chemical structures that also target the SST subtype 2 receptor in U.S. Pat. No. 6,867,202 and US23100561A1 (both of which are herein incorporated in their entirety by reference). As well, Thurieau et al disclose a number of imidazolyl derivatives in US20040176379A1 and Troxler also discloses a number of novel non-peptide samatostatin antagonists in U.S. Pat. No. 6,635,647 and U.S. Pat. No. 6,861,430 (all of which are herein incorporated in their entirety by reference).

The somatostatin inhibitors may also contain or be used to obtain or design "peptide mimetics". For example, a peptide mimetic may be made to mimic the function of an SSTR antagonist. "Peptide mimetics" are structures which serve as substitutes for peptides in interactions between molecules (See Morgan et al (1989), *Ann. Reports Med. Chem.* 24:243-252 for a review). Peptide mimetics include synthetic structures which may or may not contain amino acids and/or peptide bonds but retain the structural and functional features protein of the invention, including biological activity and a reduced propensity to activate human T cells. Peptide mimetics also include peptoids, oligopeptoids (Simon et al (50)).

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of the secondary structures of the proteins of the invention. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

The methods described include giving the antagonist to a subject at any blood glucose level. Accordingly in one embodiment, the subject has any blood glucose level. In another embodiment, the subject has a blood glucose level of less than 4.0 mM.

The purpose of using a somatostatin inhibitor is to prevent the patient from becoming hypoglycemic. When the subject is already hypoglycemic, glucose or glucagon could be given as well. The goal of treatment with a somatostatin inhibitor in an insulin-dependent diabetic subject before insulin injection is to prevent a hypoglycemic episode. Accordingly, in a further embodiment, the invention provides a treatment regimen for controlling blood glucose comprising:

(a) monitoring the blood glucose level in a diabetic subject;
(b) administering a somatostatin inhibitor to the diabetic subject before insulin injection when blood glucose levels are normal or below normal, i.e. when the blood glucose level in (a) is in the range of 4.0 to 6.0 mM or less than 4.0 mM, and
(c) administering insulin to the diabetic subject when the blood glucose level in (a) is in the range of 5.0 to 15.0 mM;
(d) repeating steps (a) and (b) to control the blood glucose level wherein controlling the blood glucose level means that the blood glucose level is in the range of 4.0 to 6.0 mM.

The disclosure also provides a pharmaceutical composition for controlling tight blood glucose levels in a subject in need thereof comprising a somatostatin inhibitor and a pharmaceutically acceptable carrier, diluent or excipient.

The disclosure further provides a pharmaceutical composition for treating or preventing hypoglycemia in a subject comprising a somatostatin inhibitor and a pharmaceutically acceptable carrier, diluent or excipient.

In one embodiment, the subject is an insulin-dependent diabetic subject. In another embodiment, the subject suffers from idiopathic hypoglycemia. In a further embodiment, the subject has an insulinoma.

The somatostatin inhibitors may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active or effective amount of the pharmaceutical compositions of the present invention is defined as an amount effective, at dosages and for periods of time necessary to achieve the desired result. For example, a therapeutically active or effective amount of a substance may vary according to factors such as the disease state, age, sex, and weight of the individual, and the ability of protein to elicit a desired response in the individual. Dosage regime may be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound. The active substance may be formulated into delayed release formulations such that blood glucose levels can be controlled or hypoglycemia prevented for longer periods of time than a conventional formulation.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences (2000—20th edition) Mack Publishing Company). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Results

Non-diabetic and STZ-diabetic rats were injected with insulin (10 U/kg and 5 U/kg). These doses yielded reproducible responses of plasma glucose (FIG. 1). In diabetic rats, plasma glucose is elevated approximately 3- to 4-fold before hypoglycemia is induced. A subcutaneous injection of insulin was given immediately after the sample was taken at time 0 in all groups of rats to induce hypoglycemia. Plasma glucose levels dropped to the same target hypoglycemia (2.75±0.25 mM) in both non-diabetic and diabetic rats. The plasma glucose levels are comparable in all 4 groups because whenever necessary, a small amount of glucose would be infused intravenously to maintain plasma glucose levels in the target range. This technique of glucose clamping is a well-established method in diabetes research which allows precise comparison between different groups at a specific glycemic level.

It can be seen that while non-diabetic rats (N-ctrl) have a robust glucagon response to low plasma glucose levels, diabetic control rats (D-ctrl) did not respond at all. When SSTR antagonist was infused before and after insulin injection, the glucagon response was markedly augmented in non-diabetic rats (N+SSTRa). With the high insulin dose in non-diabetic rats, insulin induced a 3-fold greater increase in plasma glucagon when the SSTR2 antagonist was given (1500 nmol/kg/h) (FIG. 2). In diabetic rats (D+SSTRa), glucagon was increased during SSTR2 antagonist infusion before insulin was given, and this increase in plasma glucagon was maintained throughout hypoglycemia (FIG. 2), and yielded a more modest increase in plasma glucagon.

Subsequently, a lower dose of insulin (5 U/kg) was used, which is more similar to the clinical situation, and a higher dose of the antagonist (3000 nmol/kg/h) to find out whether under those conditions, the antagonist would be more efficient in increasing the glucagon response to hypoglycemia. In non-diabetic rats (N-ctrl), a robust glucagon hypoglycemia is seen. In contrast, the response of diabetic rats (D-ctrl) was greatly decreased as compared to their non-diabetic counterparts (FIG. 3). With the SSTR2 antagonist, the peak glucagon response of diabetic rats (D+SSTRa) was almost 7-fold increased in diabetic rats (FIG. 3) and there was a tendency to even exceed that of non-diabetic controls. This is also shown by calculating the area under the curve (AUC) in the same figure. The enhancement of the glucagon response in diabetic rats infused with SSTR2 antagonist is highly significant (P<0.03).

The SSTR2 antagonist infusion fully normalized the defective corticosterone response to hypoglycemia in diabetic rats (FIG. 5). This restoration of the corticosterone response was highly significant (P<0.03). There were also increases in the corticosterone response to hypoglycemia in both SSTR2 antagonist-treated non-diabetic and diabetic rats even at the higher insulin dose and lower SSTR2 antagonist dose (FIG. 4).

To achieve comparable hypoglycemia in non-diabetic and diabetic rats after insulin is administered, it is necessary to clamp plasma glucose concentrations at a desired target level. This technique is referred to as the "glucose clamp" and is achieved by intravenously infusing glucose whenever necessary.

A normal response to hypoglycemia is an increase of glucose production by the liver due to the action of counterregulatory hormones (primarily glucagon and epinephrine; corticosterone during prolonged hypoglycemia). Because of faulty counterregulatory hormone responses, diabetic rats can respond to hypoglycemia with only attenuated glucose production. Therefore, it is anticipated that if the somatostatin SSTR2 antagonist can improve counterregulatory hormone responses to hypoglycemia, endogenous glucose production in those animals should be increased markedly. Consequently, less glucose infusion should be required during hypoglycemia in animals which receive SSTR2 antagonist.

FIG. 6 clearly demonstrates that SSTR antagonist treatment results in a lesser requirement of exogenous glucose administration in diabetic rats (D+SSTRa) compared with their untreated counterrparts (D-ctrl), i.e. less glucose infusion was necessary in both non-diabetic and diabetic rats receiving the SSTR2 antagonist than in controls that did not receive the SSTR2 antagonist during the hypoglycemic clamp. This suggests that SSTR antagonist treatment may also increase production of glucose during hypoglycemia in diabetic rats (D+SSTRa). The same pattern of improvement is also observed in non-diabetic rats treated with the antagonist (N+SSTRa) compared to controls (N-ctrl). Requirements of glucose infusion cannot be compared between non-diabetic and diabetic rats since the latter are insulin resistant. This marked variability in insulin sensitivity is also observed in poorly controlled type 1 diabetic patients. Because of faulty counterregulatory hormone responses, diabetic rats respond to hypoglycemia with attenuated glucose production.

If the SSTR antagonist improves hormone counterregulation to hypoglycemia, endogenous glucose production is markedly increased. Consequently, less glucose infusion is required during hypoglycemia in animals receiving SSTR antagonist.

SSTR antagonist (1500 nmol/kg/h) given to diabetic rats dramatically increased (4-fold, AUC) plasma epinephrine levels in response to hypoglycemia (insulin: 10 U/kg) (FIG. 7). This marked activation of epinephrine counterregulation was specific to hypoglycemia since basal infusion of the SSTR antagonist did not affect plasma epinephrine levels.

There was no effect of the SSTR antagonist (1500 nmol/kg/h) on plasma norepinephrine, neither during basal infusion of SSTR antagonist nor during insulin-induced hypoglycemia (insulin: 10 U/kg) (FIG. 8). Taken together, FIGS. 7 and 8 show that infusion of SSTR antagonist itself does not stimulate an increase in circulating catecholamine levels, which indicates that SSTR antagonist administration, per se, does not elicit a stress hormone response.

A growth hormone response to hypoglycemia (insulin: 5 U/kg) was not observed in diabetic or non-diabetic rats (FIG. 9). This may be because the peak growth hormone response was missed or because the hypoglycemia was not prolonged sufficiently. SSTR antagonist (3000 nmol/kg/h) did not affect GH levels in diabetic rats, regardless of hypoglycemia.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

```
Human Somatostatin Pre-Proprotein (NCBI: NP_001039 (SEQ ID NO:3))
  1 mlscrlqcal aalsivlalg cvtgapsdpr lrqflqksla aaagkqelak yflaellsep
 61 nqtendalep edlsqaaeqd emrlelqrsa nsnpamapre rkagcknffw ktftsc Rat Somatostatin Pre-Proprotein (NCBI: NP_036791 (SEQ ID NO: 4))
  1 mlscrlqcal aalcivlalg gvtgapsdpr lrqflqksla aatgkqelak yflaellsep
 61 nqtendalep edlpqaaeqd emrlelqrsa nsnpamapre rkagcknffw ktftsc
```

TABLE 2

| | SST receptor type: | | | | |
|---|---|---|---|---|---|
| | SSTR1 | SSTR2 | SSTR3 | SSTR4 | SSTR5 |
| Chromosomal localization: | 14q13 | 17q24 | 22q13.1 | 20p11.2 | 16p13.3 |
| Tissue distribution: | brain pituitary islet stomach kidney liver | brain pituitary islet (α-cell) stomach kidney | brain pituitary islet stomach | brain islet stomach lung placenta | brain pituitary islet (β-cell) stomach |

Table adapted from Patel, Y C. "Somatostatin and its receptor family." Frontiers in Neuroendocrinology, 20: 157-198, 1999.

TABLE 3

```
Human Somatostatin Receptor Type 1 ((NCBI: NP_001040 (SEQ ID NO:5))
    1 mfpngtassp ssspspspgs cgegggsrgp gagaadgmee pgrnasqngt lseqqgsail
   61 isfiysvvcl vglcgnsmvi yvilryakmk tatniyilnl aiadellmls vpflvtstll
  121 rhwpfgallc rlvlavdavn mftsiycltv lsvdryvavv hpikaaryrr ptvakvvnlg
  181 vwvlsllvil pivvfsrtaa nsdgtvacnm lmpepaqrwl vgfvlytflm gfllpvgaic
  241 lcyvlliakm rmvalkagwq qrkrserkit lmvmmvvmvf vicwmpfyvv qlnvfaeqd
  301 datvsqlsvi lgyanscanp ilygflsdnf krsfqrilcl swmdnaaeep vdyyatalks
  361 raysvedfqp enlesggvfr ngtctsritt l Rat Somatostatin Receptor Type 1 (NCBI: NP_036851 (SEQ ID NO:6))
    1 mfpngtapsp tsspssspgg cgegvcsrgp gagaadgmee pgrnaaqngt lseqqgsail
   61 isfiysvvcl vglcgnsmvi yvilryakmk tatniyilnl aiadellmls vpflvtstll
  121 rhwpfgallc rlvlsvdavn mftsiycltv lsvdryvavv hpikaaryrr ptvakvvnlg
  181 vwvlsllvil pivvfsrtaa nsdgtvacnm lmpepaqrwl vgfvlytflm gfllpvgaic
  241 lcyvlliakm rmvalkagwq qrkrserkit lmvmmvvmvf vicwmpfyvv qlnvfaeqd
  301 datvsqlsvi lgyanscanp ilygflsdnf krsfqrilcl swmdnaaeep vdyyatalks
  361 raysvedfqp enlesggvfr ngtcasrist l Human Somatostatin Receptor Type 2 (NCBI: NP_001041 (SEQ ID NO:7))
On chromosome 17q24
    1 mdmadeplng shtwlsipfd lngsvvstnt snqtepyydl tsnavltfiy fvvciiglcg
   61 ntlviyvilr yakmktitni yilnlaiade lfmlglpfla mqvalvhwpf qkaicrvvmt
  121 vdginqftsi fcltvmsidr ylavvhpiks akwrrprtak mitmavwgvs llvilpimiy
  181 aglrsnqwgr ssctinwpge sgawytgfii ytfilgflvp ltiiclcylf iiikvkssgi
  241 rvgsskrkks ekkvtrmvsi vvavfifcwl pfyifnvssv smaisptpal kgmfdfvvvl
  301 tyanscanpi lyaflsdnfk ksfqnvlclv kvsgtddger sdskqdksrl nettetqrtl
  361 lngdlqtsi Rat Somatostatin Receptor Type 2 (NCBI: NP_062221 (SEQ ID NO:8))
    1 meltseqfng sqvwipspfd lngslgpsng snqtepyydm tsnavltfiy fvvcvvglcg
   61 ntlviyvilr yakmktitni yilnlaiade lfmlglpfla mqvalvhwpf gkaicrvvmt
  121 vdginqftsi fcltvmsidr ylavvhpiks akwrrprtak minvavwgvs llvilpimiy
  181 aglrsnqwgr ssctinwpge sgawytgfii yafilgflvp ltiiclcylf iiikvkssgi
  241 rvgsskrkks ekkvtrmvsi vvavfifcwl pfyifnvssv svaisptpal kgmfdfvvil
  301 tyanscanpi lyaflsdnfk ksfqnvlclv kvsgaedger sdskqdksrl nettetqrtl
  361 lngdlqtsi Human Somatostatin Receptor Type 3 (NCBI: NP_001042 (SEQ ID NO:9))
    1 mdmlhpssvs ttsepenass awppdatlgn vsagpspagl avsgvliplv ylvvcvvgll
   61 gnslviyvvl rhtaspsvtn vyilnlalad elfmlglpfl aaqnalsywp fgslmcrlvm
  121 avdginqfts ifcltvmsvd rylavvhptr sarwrtapva rtvsaavwva savvvlpvvv
  181 fsgvprgmst chmqwpepaa awragfiiyt aalgffgpll viclcylliv vkvrsagrrv
  241 wapscqrrrr serrvtrmvv avvalfvlcw mpfyvlnivn vvcplpeepa ffglyflvva
  301 lpyanscanp ilygflsyrf kqgfrrvllr parrvrsqep tvgppektee edeeeedgee
  361 sreggkgkem ngrvsqitqp gtsgqerpps rvaskeqqll pqeastgeks stmrisyl Rat Somatostatin Receptor Type 3 (NCBI: NP_598206 (SEQ ID NO:10))
    1 maavtypssv pttldpgnas sawpldtslg nasagtslag lavagilisl vylvvcvvgl
   61 lgnslviyvv lrhtsspsvt svyilnlala dalfmlglpf laaqnalsyw pfgslmcrlv
  121 mavdginqft sifcltvmsv drylavvhpt rsarwrtapv armvsaavwv asavvvlpvv
  181 vfsgvprgms tchmqwpepa aawrtafiiy taalgffgpl lviclcylli vvkvrsttrr
  241 vrapscqwvq apacqrrrrs errvtrmvva vvalfvlcwm pfyllnivnv vcplpeepaf
  301 fglyflvval pyanscanpi lygflsyrfk qgfrrillrp srrvrsqepg sgppekteee
  361 edeeeeerre eeerrmqrgq emngrlsqia qpgpsgqqqr pctgtakeqq llpqeatagd
  421 kastlshl Human Somatostatin Receptor Type 4 (NCBI: NP_001043 (SEQ ID NO:11))
    1 msapstlppg geeglgtawp saanassapa eaeeavagpg daraagmvai qciyalvclv
   61 glvgnalvif vilryakmkt attiyllnla vadelfmlsv pfvassaalr hwpfgsvlcr
  121 avlsvdglnm ftsvfcltvl svdryvavvh plraatyrrp svaklinlgv wlasllvtlp
  181 iaifadtrpa rggqavacnl qwphpawsav fvvytfllgf llpvlaiglc yllivgkmra
  241 valragwqqr rrsekkitrl vlmvvvvfvl cwmpfyvvql lnlvvtslda tvnhvslils
  301 yanscanpil ygflsdnfrr sfqrvlclrc cllegaggae eepldyyata lkskggagcm
  361 cpplkcqqea lqpepgrkri pltrttf Rat Somatostatin Receptor Type 4 (NCBI: NP_037168 (SEQ ID NO:12))
    1 mntpatlplg gedttwtpgi naswapdeee davrsdgtgt agmvtiqciy alvclvglvg
   61 nalvifvilr yakmktatni yllnlavade lfmlsvpfva saaalrhwpf gavlcravls
  121 vdglnmftsv fcltvlsvdr yvavvhplra atyrrpsvak linlgvwlas llvtlpiavf
  181 adtrpargge avacnlhwph pawsavfviy tfllgfllpv laigicylli vgkmravalr
  241 agwqqrrrse kkitrlvlmv vtvfvlcwmp fyvvqllnlh vtsldatvnh vslilsyans
  301 canpilygfl sdnfrrsfqr vlclrcclle ttggaeeepl dyyatalksr ggpgcicppl
  361 pcqqepmqae packrvpftk tttf Human Somatostatin Receptor Type 5 (NCBI: NP_001044 (SEQ ID NO:13))
    1 meplfpastp swnasspgaa sgggdnrtlv gpapsagara vlvpvlyllv caaglggntl
   61 viyvvlrfak mktvtniyil nlavadvlym lglpflatqn aasfwpfgpv lcrlvmtldg
  121 vnqftsvfcl tvmsvdryla vvhplsaarw rrprvaklas aaawvlslcm slpllvfadv
  181 qeggtcnasw pepvglwgav fiiytavlgf fapllviclc yllivvkvra agvrvgcvrr
```

TABLE 3-continued

```
241 rserkvtrmv lvvvlvfagc wlpfftvniv nlavalpqep asaglyffvv ilsyanscan
301 pvlygflsdn frqsfqkvlc lrkgsgakda dateprpdri rqqqeatppa hraaanglmq
361 tskl Rat Somatostatin Receptor Type 5 (NCBI: NP_037014 (SEQ ID NO:14))
  1 meplslastp swnasaassg nhnwslvgsa spmgaravlv pvlyllvctv glsgntlviy
 61 vvlrhakmkt vtnvyilnla vadvlfmlgl pflatqnavv sywpfgsflc rlvmtldgin
121 qftsifclmv msvdrylavv hplrsarwrr prvakmasaa vwvfsllmsl pllvfadvqe
181 gwgtcnlswp epvglwgaaf itytsvlgff gpllviclcy llivvkvkaa gmrvgssrrr
241 rsepkvtrmv vvvvlvfvgc wlpffivniv nlaftlpeep tsaglyffvv vlsyanscan
301 pllygflsdn frqsfrkvlc lrrgygmeda daieprpdks grpqatlptr sceanglmqt
361 sri
```

TABLE 4

```
Human Somatostatin Pre-Proprotein mRNA (NCBI: NM_001048 (SEQ ID NO:15))
  1 gggagacggt tgagagcaca caagccgctt taggagcagg gttcggagcc atcgctgctg
 61 cctgctgatc cgcgcctaga gtttgaccag ccactctcca gctcggcttt cgcggcgccg
121 agatgctgtc ctgccgcctc cagtgcgcgc tggctgcgct gtccatcgtc ctggccctgg
181 gctgtgtcac cggcgctcac tcggacccca gactccgtaa gtttctgcag aagtccctgg
241 ctgctgccgc ggggaagcag gaactggcca agtacttctt ggcagagctg ctgtctgaac
301 ccaaccagac ggagaatgat gccctggaac atgaagatct gtcccaggct gctgagcagg
361 atgaaatgag gcttgagctg cagagatctg ctaactcaaa accggctatg cacccagag
421 aacgcaaagc tggctgcaag aatttcttct ggaagacttt aacatcctgt tagctttctt
481 aactagtatt gtccatatca gacctctgat ccctcgcccc caaaccccat ctctcttccc
541 taatcctcca agtcttcagc gagacccttg cattagaaac tgaaaactgt aaatacaaaa
601 taaaattatg gtgaaattat gaaaaatgtg aaaaaaaaaa aaaaaaaaaa aaaaaaaaaa
661 aaaaa Rat Somatostatin Pre-Proprotein mRNA (NCBI: NM_012659 (SEQ ID NO:16))
  1 tgcggacctg cgtctagact gacccacagc gctcaagctc ggctgtctga ggcaggggag
 61 atgctgtcct gccgtctcca gtgcgcgctg gccgcgctct gcatcgtcct ggctttgggc
121 ggtgtcaccg gggcgccctc ggaccccaga ctccgtcagt ttctgaagaa gtctctggcg
181 gctgccaccg ggaaacagga actggccaag tacttcttgg cagaactgct gtctgagccc
241 aaccagacag agaacgatgc cctggagcct gaggatttgc cccaggcagc tgagcaggac
301 gagatgaggc tggagctgca gaggtctgca aactcgaacc cagccatggc accccgggaa
361 cgcaaagctg gctgcaagaa cttcttctgg aagacattca atcctgtta gctttaatat
421 tgttgtctca gccagacctc tgatccctct cctccaaatc ccatatctat tccttaactc
481 ccagcccccc cccaatgct caactagacc ctgcgttaga aattgaagac tgtaaataca
541 aaataaaatt atggtgaaat tatg
```

TABLE 5

```
Human Somatostatin Receptor Type 1 mRNA (NCBI: NM_001049 (SEQ ID NO:17))
   1 tggtcatcga acggaggcag ctcctcacat ggatttagaa gagctggcgt ccccgcccgc
  61 ccaagccttt aaactctcgt ctgccagaac ccgccaactc tccaggctta gggccagttt
 121 cagagattat aagagtaatt gcgtgggcac ctgtgctggg gccaggcgca aagaagggag
 181 ttggtctgcg cgaagatcgt caacctgata acagaccgca catgcacttt gcaccgacca
 241 tctacgtctc agtatggagg ttgcgcactt tggctgctga cgcgctggtg gtgctcatta
 301 atcatttacc agtccagagc cgcgccagtt aatggctgtg ccgtgcggtg ctaccacatc
 361 ctggcctctc ctctccacgg tcgcctgtgc ccgggcaccc cggagctgca aactgcagag
 421 cccaggcaac cgctgggctg tgcgccccgc cggcgccggt aggagccgag atccccgcag
 481 cggttgcgct atacccggag gcgctgggcg gctgtgggct gcaggcaagc ggtcgggtgg
 541 ggagggaggg cgcaggcggc gggtgcgcga ggagaaagcc ccagccctgg cagccccact
 601 ggccccctc agctgggatg ttccccaatg gcaccgcctc ctctccttcc tcctctccta
 661 gccccagccc gggcagctgc ggcgaaggcg gcggcagcag gggccccggg gccggcgctg
 721 cggacggcat ggaggagcca gggcgaaatg ctcccagaa cggaccttg agcgaggcc
 781 agggcagcgc catcctgatc tctttcatct actccgtggt gtgcctggtg gggctgtgtg
 841 ggaactctat ggtcatctac gtgatcctgc gctatgccaa gatgaagacg gccaccaaca
 901 tctacatcct aaatctggcc attgctgatg agctgctcat gctcagcgtg ccctttccta g
 961 tcacctccac gttgttgcgc cactggccct tcggtcgcgt gtctctgcgc ctcgtctca
1021 gcgtggacgc ggtcaacatg ttcaccagca tctactgtct gactgtgctc agcgtggacc
1081 gctacgtggc cgtggtgcat cccatcaagg cggcccgcta ccgccggccc accgtggcca
1141 aggtagtaaa cctgggcgtg tgggtgctat cgctgctcgt catcctgccc atcgtggtct
1201 tctctcgcac cgcggccaac agcgacggca cggtggcttg caacatgctc atgccagagc
1261 ccgctcaacg ctggctggtg ggcttcgtgt tgtacacatt tctcatgggc ttcctgctgc
1321 ccgtgggggc tatctgcctg tgctacgtgc tcatcattgc taagatgcgc atggtggccc
1381 tcaaggccgg ctggcagcag cgcaagcgct ggagcgcaa gatcaccta atggtggatga
1441 tggtggtgat ggtgtttgtc atctgctgga tgccttctca cgtggtgcag ctggtcaacg
1501 tgtttgctga gcaggacgac gccacggtga gcctcaggct ggtcatcctg ggctatgcca
1561 acagctgcgc caacccatc ctctatgcc ttctctcaga caattccaag cgctctttcc
1621 aacgcatcct atgcctcagc tggatggaca acgccgcgga ggagcggttt gactattacg
1681 ccaccgcgct caagagccgt gcctacagtg tggaagactt ccaacctgag aacctggagt
1741 ccggcggcgt cttccgtaat ggcacctgca cgtcccggat cacgacgctc tgagcccggg
```

TABLE 5-continued

```
1801 ccacgcaggg gctctgagcc cgggccacgc aggggccctg agccaaaaga gggggagaat
1861 gagaagggaa ggccgggtgc gaaagggacg gtatccaggg cgccaggggtg ctgtcgggat
1921 aacgtggggc taggacactg acagcctttg atggaggaac caagaaagg cgcgcgacaa
1981 tggtagaagt gagagctttg cttataaact gggaaggctt tcaggctacc tttttctggg
2041 tctcccactt tctgttcctt cctccactgc gcttactcct ctgaccctcc ttctattttc
2101 cctaccctgc aacttctatc ctttcttccg caccgtcccg ccagtgcaga tcacgaaatc
2161 attaacaact cattctgatc ctcagcccct ccagtcgtta tttctgtttg tttaagctga
2221 gccacggata ccgccacggg tttccctcgg cgttagtccc tagccgcgcg gggccgctgt
2281 ccaggttctg tctggtgccc ctactggagt cccgggaatg accgctctcc ctttgcgcag
2341 ccctaccttta aggaaagttg gacttgagaa agatctaagc agctggtctt ttctcctact
2401 cttgggtgaa ggtgcatctt tccctgccct cccctgtccc cctctcgccg cccgccgcc
2461 accaccactc tcactccacc cagagtagag ccaggtgctt agtaaaatag gtcccgcgct
2521 tcgaactcca ggctttctgg agttcccacc caagccctcc tttggagcaa agaaggagct
2581 gagaacaagc cgaatgagga gttttttataa gattgcgggg tcggagtgtg ggcgcgtaat
2641 aggaatcacc ctcctactgc gcgttttcaa agaccaagcg ctgggcgctc ccgggccgcg
2701 cgtctgcgtt aggcagggca gggtagtgca gggcacacct tccccggggt tcgggggttcg
2761 gggttcggtt gcagggctgc agcccgcctt ggctttctcc ctcacccaag tttccggagg
2821 agccgaccta aaagtaacaa tagataaggt ttcctgctcc agtgtatctc aaaagaccgg
2881 gcgccagggg cggggaccct agggcgacgt cttcagagtc cgccagtgtt ggcggtgtcg
2941 ccgcaacctg caggctcccg agtggggcct gcctggtctc tagaggggtg ctgcctttca
3001 agcggtgcct aagaagttat tttcctgttt aacatatata tttattaatt tatttgtcgt
3061 gttggaaaat gtgtctctgc tttccttttc tctgcttgcc tagccccagg tcttttcttt
3121 gggaccctgg gggcgggcat ggaagtggaa gtagggcaa gctcttgccc cactccctgg
3181 ccatctcaac gcctctcctc aatgctgggc cctcttatct catcctttcc tctagctttt
3241 ctattttttga ttgtgttgag tgaagtttgg agattttca tacttttctt actatagtct
3301 cttgttttgtc ttattaggat aatacataaa tgataatgtg ggtatcctc ctctccatgc
3361 acagtggaaa gtcctgaact cctggctttc caggagacat atataggga acatcaccct
3421 atatataatt tgagtgtata tatatttata tatatgatgt ggacatatgt atacttatct
3481 tgctccattg tcatgagtcc atgagtctaa gtatagccac tgatggtgac aggtgtgagt
3541 ctggctggaa cactttcagt ttcaggagtg caagcagcaa tcaaacctgg agctgaggaa
3601 tctaattcag acagagactt taatcactgc tgaagatgcc cctgctccct ctgggttcca
3661 gcagaggtga ttcttacata tgatccagtt aacatcatca ctttttttga ggacattgaa
3721 agtgaaataa tttgtgtctg tgtttaatat taccaactac attggaagcc tgagcagggc
3781 gaggaccaat aattttaatt atttatattt cctgtattgc tttagtatgc tggcttgtac
3841 atagtaggca ctaaatacat gttttgttggt tgattgttta agccagagtg tattacaaca
3901 atctggagat actaaatctg gggttctaag gttcactcat tgacatgata tacaatggtt
3961 aaaatcacta ttgaaaaata cgttttgtgt atatttgctt caacaacttt gtgcttttcct
4021 gaaagaagta accaagagtt aagatatccc taatgttttg cttaaactaa tgaacaaata
4081 tgctttgggt cataaatcag aaagtttaga tctgtccctt aataaaaata tatattacta
4141 ctccttttgga aaatagattt ttaatggtta agaactgtga aatttacaaa tcaaaatctt
4201 aatcattatc cttctaagag gatacaaatt tagtgctctt aacttgttaa aattgtaata
4261 ttaactaaat aaacagatgt attatgctgt taaaaaaaaa aaaaaaaaa aaaaaaaaa
4321 aaaaaaaaaa aaaaaaaaaa aaa
```

Rat Somatostatin Receptor Type 1 mRNA (NCBI: NM_012719 (SEQ ID NO:18))

```
   1 gctcgccaca gctgctgcgc gctgccggga gggccaggcg cggtgagctg tgagcttgga
  61 gccttgagcc tagggagggc gcaggcagca aggggcgcaag gtgagcgtcc caaccggcgg
 121 ccacaccggc ccacttcagc tgggatgttc ccaaatggca ccgccccatc tcccacatct
 181 tctcccagct ccagcccagg cggctgcggg aaggagtct gcagcagggg tcccgggtcc
 241 ggcgctgcgg acggcatgga agaacctgga cgaaactctt cccagaacgg gacttttaagc
 301 gagggtcagg gtagcgccat tctcatctct ttcatctact ccgtggtatg cttggtggga
 361 ctgtgtggga actccatggt catttacgtg atcctgcgct acgccaagat gaagaccgca
 421 accaacatat acattctaaa cctggccatt gctgatgagc tgctcatgct cagcgtgcca
 481 tttctggtca cttacacgct gttgagccac tggcccttcg gcgcgctact ttgccgccctg
 541 gtgctcagcg tggatgcagt caacatgttc accagcatct actgtctgac tgtgcttagt
 601 gtggaccgct atgtggctgt ggtgcacccg atcaaggcag cgcgctaccg tcggaccact
 661 gtggccaaag tagtgaacct gggcgtgtgg gtgctgtcgc tactggttat cttgcccatc
 721 gtggtcttct cacgcaccgc agccaacagc gatggccctg tgcctgcaa catgctcatg
 781 cccgagcccg cccagcgctg gttggtgggc ttcgtcttat acacatttct catgggcttc
 841 ctgctgcctg tcggggccat ctgcctgtgt tacgtgctca tcattgccaa gatgcgcatg
 901 gtggccctca aggccggctg gcagcagcgc aagcgctcag agcgcaagat cactctaatg
 961 gtgatgatgg tggtgatggt tttttgtcatc tgctggatgc ctttctacgt ggtacagcta
1021 gtcaacgtgt tcgccgagca agacgacgcc acggtgagcc agttgtctgt catactcggc
1081 tatgccaata gctgtgccaa ccccatcctc tacggcttcc tgtcggacaa cttcaagcgc
1141 tcttttccagc gcatcctgtg cctcagctgg atggataacg ctgcggagga gcctgttgac
1201 tactacgcca ctgccctgaa gagtcgtgcc tacagtgtgg aggacttcca gcctgagaat
1261 ctggaatctg gaggcgtttt ccgtaatggc acctgcgctt ccaggatcag cacgctttga
1321 ggccggacgc taaccggagg gggagagtgg tcagaaaggt ggagagggga agcaggtggg
1381 agggaatgat agccgcacac caggtgctat gggagtagtg cgtgacagcg atgcagcgcc
1441 cctgtttagc aaagctatgt gactaaggta aacgggagag atttgagaat gttttcgggc
1501 catctggtat tctgaactgt gttctccaaa cccgataatt tccatcctcc ctcccagttc
1561 tgctagtaca aactgcaaac ttaacgtcgc caactccgtt tgacccttttc cctctcaagc
1621 tgttatttct gcttctttaa actgagccat cttgtgtttc ttttgggctg agtccccacc
1681 ttgcgctgaa ccccctgcgc aggtcagcgg gccagactct tcagagcggc taccagactg
1741 tccccagtta ccgctccct tttgcacagc cttactgtca agtaagccca cctccaggat
1801 gaccaggcaa ctggtctttt ctactctcaa agaaggcacc atcttccctt gggccctttc
1861 tctgcttcac tgcatccaga gcagagctgg gtgcttaaga aaaagtcctg tgcccagatg
1921 gccagacttg gtgtagtccc acccattccc tcctttggag cacaaaaagg agctaagagc
1981 cagcagaagg gcaagtttct aagattcctg ggctgtggtt gtgggtgcca gagaagccac
```

TABLE 5-continued

```
2041 cctcccatag agctcaggac ctgagcacta ggcttggagg tcccagctag gggagctccc
2101 ggcttgtgaa taacttatgc accctggtgt gtgaacctga attgcacagc agttcccctt
2161 ggaggtctcc ctagaataac aaaggattgg gttgcctgct ccctttccta gtccagctcc
2221 tgttcaagtg acaaaccgca gagccctttgc caaagctgga tggctaactt cagcttgtct
2281 ggtccctgac atttttttgcc tttcaagcgg tgcctaataa gttatttctt gtttgacata
2341 tttatttatt tatttatggt gttgaaaaaa aaagtgtgtt tccactttct ttttctgtat
2401 ttgcctaaca gggctgttct tgagaatcct ctggcaggca cgtggtggtg tggaggtgtg
2461 gaggggagca ggggtggaga aagttctctc accccaagac tccctcagaa gtttcccttc
2521 ttttgcactc cattggcctt ttcttgatcc ttccttggttt tgcttgtgtc cagtgaagtt
2581 tggagatttt aaaaatatat ttttactgta gttttgtctt gttaaaataa gtacatggca
2641 atttggttta acttttgtca gtgtggagtg gaaggcctga atccctggca tcccagaaaa
2701 cacaggggaa caaatcacat gatccgtgat gtatgtctgt atatgtgctg tcacacacaa
2761 gtcacatata tacgtgtata tatatatcat atatgtacac acacatataa aggtagattt
2821 gtcaatcttg acaactgtca ctagttcatg acaattataa ggacacccac aatgtgtgac
2881 ctgagctgta gcactccagc tgggatctga gaaacgtcag agattggagt cgctgctgaa
2941 gatgctgctg ccctttttcta tcccctcaga ggtgattctt acccagtaag tctagtcact
3001 tttgttgagg aatggaagcg aaacaattgt gtctgcattt actgactacc gtggaaacct
3061 gaacacggaa ggaccccatct cttcacttgt tgcatttgct gtgttcctgt gtatgctcgt
3121 ttgtacatag gggccactga aaggatatct tgcttggttg tttaaggaag caagtgtata
3181 tcagtggtct tagaacaatg aacctggggt tctcgggtcc acagtgacct gacatctaac
3241 ctgcaatggt cgaatgcact gttgaaaatg gtgttttgtg tacatttgct tcaagaacac
3301 atccatgctt ttcctaaaag caggaaccaa gagttaaact gtctcttctg ttttgtttaa
3361 ataaatgaac aaatatgctt ttgatcataa gtgagaaagt ttagatcttt tcctaagaat
3421 agtatatata tatatatata tgtatatata tatatatata tatgtatata tatatacttt
3481 tctgttaatt agattttta accgataaga agagtgaact ttataaactg aaatctccat
3541 cattatcata tagacaggat aaaaatgtag tgctcttacc ctgtaatagt aactgaataa
3601 aaagatgtat tatgc
```

Human Somatostatin Receptor Type 2 mRNA (NCBI: NM_001050 (SEQ ID NO:19))
On chromosome 17q24

```
   1 cgcagccacc catgcgcgcg cgctcgcaag accaccagcg cccagagccc cagtctgagg
  61 cttggcgccg gggtctgcg ggcgagggga gctctctacg tgcgagggc tagcgggagc
 121 cggcacaaga gggtcgagga gccaggaacc ccaaacgtcc ggcgccaggc gctagccaag
 181 ctgctgcgcg ccccggcgcc cagctggctc ggggacagcc gctgggtgtc ggagaccgga
 241 gctagcggat tgcagcggaa aagcaaagat gtcacactgg atccttggcc tccagggtcc
 301 attaaggtga gaataagatc tctgggctgg ctggaactag cctaagactg aaaagcagcc
 361 atggacatgg cggatgagcc actcaatgga agccacacat ggctatccat tccatttgac
 421 ctcaatggct ctgtggtgtc aaccaacacc tcaaaccaga cagagccgta ctatgacctg
 481 acaagcaatg cagtcctcac attcatctat tttgtggtct gcatcattgg gttgtgtggc
 541 aacacacttg tcatttatgt catcctccgc tatgccaaga tgaagaccat caccaacatt
 601 tacatcctca acctggccat cgcagatgag tcttcatgc tgggtctgcc tttcttggct
 661 atgcaggtgg ctctggtcca ctggcccttt ggcaaggcca tttgccgggt ggtcatgact
 721 gtggatggca tcaatcagtt caccagcatc ttctgcctga cagtcatgag catcgaccga
 781 tacctggctg tggtccaccc catcaagtcg gccaagtgga gagaccccg gacggccaag
 841 atgatcacca tggctgtgtg gggagtgtct ctgctggtca tcttgccca tatgatatat
 901 gctgggggctcc ggagcaacca gtgggggaga agcagctgca ccatcaactg gccaggtgaa
 961 tctgggggctt ggtacacagg gttcatcatc tacactttca ttctggggtt cctggtaccc
1021 ctcaccatca tctgtctttg ctacctgttc attatcatca aggtgaagtc ctctggaatc
1081 cgagtgggct cctctaagag gaagaagtct gagaagaagg tcacccgaat ggtgtccatc
1141 gtggtggctg tcttcatctt ctgctggttc ccttctacaa tattcaacgt ttcttccgtc
1201 tccatggcca tcagccccac cccagccctt aaaggcatgt ttgactttgt ggtggtcctc
1261 acctatgcta cagctgtgc caaccctatc ctatatgcct tcttgtctga caacttcaag
1321 aagagcttcc agaatgtcct ctgcttggtc aaggtgagcg gcacagatga tgggagcgg
1381 agtgacagta agcaggacaa atcccggctg aatgagacca ccgagacca gagacctc
1441 ctcaatggag acctccaaac cagtatctga actgcttggg ggtgggaaa gaaccaagcc
1501 atgctctgtc tactggcaat gggctcccta cccacactgg cttcctgcct cccacccctc
1561 acacctggct tctagaatag aggattgctc agcatgagtc caattcagag aacggtgttt
1621 gagtcagctt gtctgattga atgataatgt gctaaattga ttacctcccc cttaaagcga
1681 acactgaaat gcaggtagac aattcaaagt ctggagaaga gggatcatgc ctggatatga
1741 tctttagaaa caacaaaaat agaaaaaaat aagtatctgt gtgtttgtgt attgaaaact
1801 caatatgtaa tcttgtgttt ttatatgtat acttgtatat tccatttat tctctgtata
1861 ggcattacct acgttcctgt gtttacatac acaagtagca aattcgagta tgcatagtgt
1921 agatggacat ttgccacaac acactgcccg cagaaatgga cttaccgtga agccaataaa
1981 gttcaagctt cagggatctc tcttgcacgg gccttgccaa ggcccaggag ggacttgggc
2041 agtatgttca tgtggtcata tgttttttgta aaaaattgtg aaagtaagat atgtttgtat
2101 tgttttttctt aaagaggaac ctcgtataag cttcaagcct cacaaacctt ctagcctctg
2161 cccctggggga tttgcttcat taatttcagg caagtgaggt caatgtaaga agggaaaggg
2221 agaagatatt tgaagaacca gaatgtaaat tcatgtgtttt ccacttctca gatatagtca
2281 gagaattatt catttgccca aaaggactta agtggttgtg gtcatccatc attgtattta
2341 tcaagacaaa gccaactttg ttataagatt gcatttttt cttttcaaat tgctttagtt
2401 tttcttaggg agctcatgag gggaaaaatc actaacatga aaggcaaaaa atggactact
2461 attcctgtgg ggaaacaatt tcattctctc catcgtgaaa ataagtgaat aagagtgaag
2521 caaaattaca cctttatgag aaaccataaa attgttttta ttttttcaggc cagacatagc
2581 ttcctaatga aagaaaatgg aaatgtaatt cgacgactcc tcaagggga ctttagagga
2641 cttcatacaa agctgggcat taagaaaacc acaatgcatg aaggcaaaaa gccggcttaca
2701 cctgtaatcc cagcactttg ggaggccgag gtgggtggat cacccgaggt caggagttcg
2761 agaccagcct ggccaacatg gtgaaacccc atcactacta aaaatatgta aattagtcgg
2821 gcgtggtgtc acgtgcctgt aatcctagct gctcggggagg ctgaggcagg agaatcactt
2881 gaacttggga ggtggaggtt gcagtaagct gagattgtgc cactgcactc tagcctgagc
```

TABLE 5-continued

```
2941 aacaagagca aaactcagtc tcaaaaaaaa aaaaaaaaaa aaaaaaaaaa aaaaaa

Rat Somatostatin Receptor Type 2 mRNA (NCBI: NM_019348 (SEQ ID NO:20))
   1 gacaccggca cgctggcgag gccaccggcc ctggagcacc agtccgccgc tgggcgtcga
  61 tgatctacag gccagggtag ctctactggg gcccaggcaa gctctctcag acgccaggag
 121 ggacagcacg agccagactg ggaagctgcg agccagagag ctactgcgga gcgccaaaca
 181 cccccctaaac ctgctgcgct cccgggcgcc cggctgggta aaggacagct tctgggagct
 241 agagaacaca gagaagagag tgctcgtgga aaagcaagat gtcacgatag acccttggcc
 301 ccagagtcca ctgaggtgag aggaagatct ctgggctgct tggttctagg cggactgaag
 361 agcagccatg gagttgacct ctgagcagtt caatgggagc caagtgtgga taccttctcc
 421 ctttgacctc aacggctcac tggggccaag caatggctcc aaccagacag agccatacta
 481 cgacatgaca agcaacgcgg tcctcacgtt catctacttc gtggtgtgcg tggtggggct
 541 gtgcggcaac acgctcgtca tctacgtcat cctccgctac gccaagatga aaaccatcac
 601 caacatttac atcctcaacc tggccatcgc agatgaactc ttcatgctgg gatgcccctt
 661 cttggccatg caggtggcgc tggtccactg gccttttggc aaggccatct gccgggtggt
 721 catgactgtg gacggtatca accagttcac cagtatcttc tgcttgacgg tcatgagcat
 781 cgaccgttac ctggccgtgg tccaccccat taagtcagcc aaatggaggc gaccccggac
 841 agccaagatg atcaacgtgg ctgtgtgggg tgtgtccctg cttgtcattt tgcccatcat
 901 gatatacgct ggcctccgga gcaaccagtg gggtaggagc agctgcacca tcaactggcc
 961 gggcgaatcc ggggcatggt acacgggttt cattatctat gccttcatcc tggggttcct
1021 ggtaccccta accatcatct gtctctgcta cctgttcatc atcatcaagg tgaagtcctc
1081 tgggatccga gtggggtcgt ccaagaggaa aaagtcagag aaaaaggtga cccgaatggt
1141 atccatcgtg gtgctgtct tcatcttctg ctggctcccc ttctatatct caatgtctc
1201 gtccgtgtct gtggcaatca gccccaccac tgccctgaaa ggcatgtttg actttgtggt
1261 tatcctcacc tacgccaaca gctgcgccaa ccccatcctg tacgccttct tgtccgacaa
1321 cttcaagaag agcttccaga atgttctttg cttggtcaag gtgagtggtg cggaggatgg
1381 ggagcggagc gacagtaagc aggacaaatc ccggatgaat gagaccacgg agacccagag
1441 gacccctcctc aatggagacc tccaaaccag tatctgaaac aacccgggaa cgcaacgtgc
1501 acacgcacta gccaagcccc gcctcctggc agtgcgagcc ccattcaccc gcttcctgcc
1561 tccctaccc atcacacccg cttttctag agcagagcgg atttgagtct ggcttgtccg
1621 aaagtatacc cctctggtca catctacccc taaagtgaac gttttcgtgc aggcagacaa
1681 ttcaaagact ggagaagagg acacgatggc ctgggtgtga cccggtggaa agcagatacc
1741 cggcagaaac cggaaaaacc aaaactaaaa tcaaagttcc gcgcgtgtac gtgtgcttgc
1801 ccgctatgta atctcgtgat ctgatatttc cgtttgtaca tcacctcccc acccacaccc
1861 cggtctctgc ggagccagta tacacgtgtc ctgtgtttgt aaaaccaagt agctagttca
1921 tgtgcgtcta gtataggtgg acatttacca cagcgctgaa cctgacgaca aggactcacc
1981 atgtcagagt caatctaatc taagcttcca gcatccctct tgcatgggcc tttcccagac
2041 ccaggaggag catgagcagt atgttcatat aataatacat ttttgtaaaa agaaaaaaaa
2101 aaaaaaaaaa aaaaaa Human Somatostatin Receptor Type 3 mRNA (NCBI: NM_001051 (SEQ ID NO:21))
   1 cgcatctctc atcactcccc ctcattctgc ctttcctctc actcacggtc tcctctccct
  61 ctccctctct ctctctcccc ctctctcttt ctctctctct ctctttctcc acctcctccc
 121 gacccccttt cccctctatt tctattggct tctgtgtccc ttgctcccct cttctcttcc
 181 tcaccctggg aagcttctcc cccctatcct tgccctgcc ccccaggat gtgtcctgga
 241 gatgggggt gacgtaccag gctctggttg ggaagtcagg gccggagacc agatgggaga
 301 ggctctgtgg acagccgtgg ccgagggcct gggagggaac ctgagccgc aagcggtcta
 361 gaagtggggtg ccgtgtgggg accctagtta ggagtgccct gggggcacct ggggactggg
 421 cagggagagg ggacagcaga atgataacca gcctggcgg aaggagggaa gccctcaccc
 481 catgggcagg caaatagctg actgctgacc accctccct cagccatgga catgcttcat
 541 ccatcatcgg tgtccacgac ctcagaacct gagaatgcct cctcggcctg gcccccagat
 601 gccaccctgg gcaacgtgtc ggcggggccca agcccggcag ggctggccgt cagtggcgtt
 661 ctgatccccc tggtctacct ggtggtgtgc gtggtgggcc tgctgggtaa ctcgctggtc
 721 atctatgtgg tcctgcggca cacggccagc cctttcagtc ccaacgtcta catcctcaac
 781 ctggcgctgg ccgacgagct cttcatgctg ggctgccct tcctggccgc ccagaacgcc
 841 ctgtcctact ggccccttcgg ctccctcatg tgccgcctgg tcatggcggt ggatggcatc
 901 aaccagttca ccagcatatt ctgcctgact gtcatgagcg tggaccgcta cctggccgtg
 961 gtacatccca cccgctcggc ccgctggcgc acagctcctg ggcccgcac ggtcagcgcg
1021 gctgtgtggg tggcctcagc cgtggtggtg ctgccccgtgg tggtcttctc gggagtgccc
1081 cgcggcatga gcacctgcca catgcagtgg cccgagccgg cggcggcctg gcgagccggc
1141 ttcatcatct acacggccgc actgggcttc ttcgggccgc tgctggtcat ctgcctctgc
1201 tacctgctca tcgtggtgaa ggtgcgctca gctgggccgc gggtgtgggc accctcgtgc
1261 cagcggcggc ggcgctccga acgcagggtc acgcggcatg tggtgccgt ggtggcgctc
1321 ttcgtgctct gctggatgcc cttctacgtg ctcaacatcg tcaacgtggt gtgcccactg
1381 cccgaggagc ctgccttctt tgggctctac ttcctggtgg tggcgctgcc ctatgccaac
1441 agctgtgcca ccccatcct ttatggcttc ctctcctacc gcttcaagca gggcttccgc
1501 agggtcctgc tgcggccctc ccgccgtgtg cgcagccagg agcccactgt ggggcccccg
1561 gagaagactg aggaggagga tgaggaggag gaggatgggg aggagagcag gaggggggac
1621 aaggggaagg agatgaacgg ccgggtcagc cagatcacgc agcctggcac cagcgggcag
1681 gagcggcgc ccagcagagt ggccagcaag agcagcagc tcctacccca agaggcttcc
1741 actgggggaga agtccagcac gatgcgcatc agctacctgt agggcctggg gaaagccagg
1801 atgcccgag gaagaggcag aagccgtggg tgtgcctagg gcctacttcc caaggtgcca
1861 caggcccatg atgggatgtt gaggggcctg gactttgatg ctattgctgc caggtcttgc
1921 tgtgtgacct tgggtaggtt gcttctactc tctgggcctt gttttctcct ctgtgactca
1981 gggataggag tcatcagcct ggatgagcta tgtcagatga gaggtttgga gggcactgtt
2041 gctgggctga cctggctgag caggcaaaag gtgggtgcag actggcctcc ccccagggat
2101 ggagtgtctt ggggcatcaa cta
```

TABLE 5-continued

Rat Somatostatin Receptor Type 3 mRNA (NCBI: NM_133522 (SEQ ID NO:22))
```
   1 caggcgtctc tccttactcc ccctcattct gcctttccgc ccacacactg tctcctctcc
  61 ctctcctctc tctctctcca cctccgaccc tccccctcct ttccttattt tcctcggcct
 121 tcttatgtcc cctgctatct cacatttctg tcatctttcg aagtgccttc tgtcacccc
 181 aactgggtgc catctgaaga cccccatcct gtgtccggca cccgccacgt gtcctggaga
 241 tgggggtga cgtatcaggt gcgggtggca agtcaggact gaggaccaga tgggagaggc
 301 gacgtgggct gacgtggccc ccgaggacct aggaagggcc caaccaagcc cacaagcact
 361 ggaggagtgg gcactgtgtg tcaccccagc tggctgtgct ctggtggtac ctggctgcag
 421 aaggttatcc agcctggcga ctgcaaaggg aattcttgcc ctgtgggcag aatcttggaa
 481 cctccatgca gcagaatgtc agaactggac caaagagatg caagctaccc atggcttccc
 541 aggccttgag caccccctca tgctggcagt ggtgcatctg aagagtccct tccacctttg
 601 cagcaacccc gtaaggtttg gctagttgg ctgctgactg atcctcatcc ctgccatggc
 661 cgctgttacc tatccttcat ccgtgcctac gaccttggac cctgggaatg catcctcagc
 721 ctggcccctg gacacgtccc tggggaatgc atctgctggc actagcctgg caggactggc
 781 tgtcagtggc atcttgatct ctctggtgta cctggtggtg tgtgtggtgg gtttgctggg
 841 caattcactg gtgatctacg tggttctgcg gcacacgtcc agccatcag tgaccagtgt
 901 ctatatcctc aacctggcac tggctgacga actcttcatg ctggggctac ctttcctgg
 961 tgctcagaac gccctgtcct actggccttt cggctctctc atgtgtcgt tggtcatggc
1021 cgtggatggc atcaaccagt tcaccagcat cttctgcctc accgtcatga gtgtggaccg
1081 ctacctggct gtggtgcacc ccacacgctc tgcccgctgg cgcacggcac ctgtggctcg
1141 aatggtcagt gcagctgtct gggtggcctc agctgtgtc gtgctgcctg tggttgtgtt
1201 ctcaggagtg ccccgaggga tgagcacgtg ccacatgcag tggccagagc cagcggctgc
1261 ctggcgaaca gccttcatca tctatacggc cgcactgggc tttttttggc ccctgctggt
1321 catctgctta tgctacctgc ttattgtggt aaggtgcgg tcgaccacac ggcgggtgcg
1381 ggcgccctcg tgcagtgga tacaggcacc cgcttgccag cggcggcggc gctctgagcg
1441 caggggtgaca cgcatggtgg tggctgtggt ggcactcttc gtcctctgct ggatgccttt
1501 ctatttactc aacatcgtta atgtggtgtg cccgctgccg gaggagcccg ccttctttgg
1561 cctctacttc tgtggtggtcg cgctgcccta cgccaacagc tgcgcaaacc ccatcctcta
1621 cggcttcctc tcctaccgct tcaagcaggg cttccgcagg atcctgctaa gacctttctcg
1681 gcgagtacgc agccaggagc cagggtctgg ccctccagag aagacggagg aggaggagga
1741 tgaagaggaa gaagagagaa gggaagagga agagcggagg atgcagagag ggcaggagat
1801 gaatggggagg ctcagtcaga tcgcacagcc aggcccagt ggacagcagc aacgccttg
1861 cacagggact gccaaggaac agcagcttct acccccaggaa gccacagctg gggacaaggc
1921 cagcacgctg agccatctgt aagaaccttc aaagagccag catgatcctg aagagagcag
1981 aagctatgct tgacctaagg cacgagtacc agacacatgg cagtgttcta agcaagcaac
2041 agctagagtg agcttattta catggctgtc ctggccctct ctggaccgtt gtggtactag
2101 ggtccagtga tggaatgtcc ataggcctgg gctctgtccc actgtgccag ggcttgctgt
2161 gtatactttg gccagtcact agccctctct gggtcttgtt ttcttctttt gactcaggga
2221 tgggtaaaat gagccctgtc agaagagggg tctggaatcc ttattgggat taatctccta
2281 atcagagccc aagttaagaa tttgcacagt ctgaccaaga aacaagatat cttggggatc
2341 agtctgtatc ttggccctca aggagataca ccagggcttg ggaaatgaca gatgcagatg
2401 acctggggt gggtgcttgg ctgaaaccta aaggaagtgt tagttggtgt ggtggggatgc
2461 cacggcttag gacgcaagtg agcccttcc atgctgctct gtggcctcag ccactctgtt
2521 catgtgcagg cctcctacct cttctgcagg gcagtccggg tgtcctacag accctcaccc
2581 cagcgtctga gcattgggcc ttctgtgctc ctggacacca ggggaagaac ttcccagaag
2641 gcaggtgaaa ccaagtttca gggttcttg ctgcttgggc cccctggga cctacgtgtg
2701 actggtcttc taattttgta ttccttctct ggagggaaga ttgcacacca ccaggctcag
2761 gccaccgga gactgactca ccctattcag gtcagctacc tagtcccag ggctatgcag
2821 cagcctgagg gaaggagagg gagaaaggag gagagggagc tgaggcagta agaagaggag
2881 ggggatggga tcggagggga aagagaacag aacttttgtg tgatcttgag tcaacctttct
2941 cccccttgag ctaagctcag tttgcagcac tgatgtttc aggaaggatc tgaaggagac
3001 atgtgaccag atcccctgg agggtgcgtg gggtggtga gaggggcaca ggtcatgatg
3061 gagtcgtggg aatgggcttg gctcctcagg agggatggta agtcctttgt gtgggtcagt
3121 cctcccatcc tctattccca gggctccagc tgatgtagag actaacaggc tgtcatgggg
3181 agtagccact gtcccagctg ggtcaggact tcattcttcc cctcccagag atggtccta
3241 tggtcccagc agtgatggcc ctggaaaggt tgaggcttct gctcaaaccc ccacctacc
3301 ctgcagaggc agggttctca gggaacccac aaatccagat gttgagaaag ctggatcttc
3361 tattcaccctc aagcctcttg gccatacct ctgtctctgc gcctcagtat cctcatcata
3421 gtgagaatgt gatccccag ttctccagtc tgttagaata caggagggaa ctgagtcatg
3481 ccaggcaagc tactgctcac cacaatgggg ctgcgtaagg atacaaagcg gccgtgttgt
3541 acctcaggct cagcccacac cttgcccttt aagtgagtgg cttcggtgtc agctactgga
3601 ggtgaaggta ttcatgagaa atggagtgca ggaggtcaga agccaaggac catgagaat
3661 gcaagccacc ccagaaggag gaagtttgca aacataggaa tgtatgggggc ctgaggccca
3721 gcccagggggt tcctctgaga aggagctggg tcaggaagta agcagtccaa ccttcctgga
3781 tggggtaggt gagccacgtc ttgcaaaggg gtgggtgacc agttgagaag ttctttgctg
3841 cttctgaccct gagctcctgt caataaagat agtgactaag aaaaaaaaaa aaaaaaaaa
3901 aaaaaaaaaa aaaaaaaaa aaaaaaaaaa aaaaaaaaa aaaaaaaaaa aaaaaaaaaa
3961 aaaaaaaaaa aaaaaaaaaa aaaaa
```

Human Somatostatin Receptor Type 4 mRNA (NCBI: NM_001052 (SEQ ID NO:23))
```
   1 atgagcgccc cctcgacgct gccccccggg ggcgaggaag ggcggggac ggcctggccc
  61 tctgcagcca atgccagtag cgctccggcg gaggcggagg aggcggtggc ggggcccggg
 121 gacgcgcggg cggcgggcat ggtcgctatc cagtgcatct acgcgctggt gtgcctggtg
 181 gggctggtgg gcaacgccct ggtcatcttc gtgatccttc gctacgccaa gatgaagacg
 241 gctaccacca tctacctgct caacctggcc gtagccgacg agtcttcat gctgagcgtg
 301 cccttcgtgg cctcgtcggc cgccctgcgc cactggccct tcggctccgt gctgtgccgc
 361 gcggtgctca gcgtcgacgg cctcaacatg ttcaccagcg tcttctgtct caccgtgctc
 421 agcgtggacc gctacgtggc cgtggtgcac cctctgcgcg cggcgaccta ccggcggccc
 481 agcgtggcca agctcatcaa cctgggcgtg tggctggcat ccctgttggt cactctcccc
```

TABLE 5-continued

```
 541 atcgccatct tcgcagacac cagaccggct cgcggcggcc aggccgtggc ctgcaacctg
 601 cagtggccac acccggcctg gtcggcagtc ttcgtggtct acactttcct gctgggcttc
 661 ctgctgcccg tgctggccat tggcctgtgc tacctgctca tcgtgggcaa gatgcgcgcc
 721 gtggccctgc gcgctggctg gcagcagcgc aggcgctggc agaagaaaat caccaggctg
 781 gtgctgatgg tcgtggtcgt ctttgtgctc tgctggatgc cttctacgt ggtgcagctg
 841 ctgaacctcg tcgtgaccag ccttgatgcc accgtcaacc acgtgtccct tatcctcagc
 901 tatgccaaca gctgcgccaa ccctattctc tatggcttcc tctccgacaa cttccgccga
 961 tccttccagc gggttctctg cctgcgctgc tgcctcctgg aaggtgctgg aggtgctgag
1021 gaggagcccc tggactacta tgccactgct ctcaagagca aggtggggc agggtgcatg
1081 tgccccccac taaaatgcca gcaggaagcc ctgcaaccag aacccggccg caagcgcatc
1141 cccctcacca ggaccaccac cttctga
```

Rat Somatostatin Receptor Type 4 mRNA (NCBI: NM_013036 (SEQ ID NO:24))
```
   1 gttcagcgtt cggctgctct ccacggcaat ccgctgcccc gggtgggcac cccgaagcat
  61 gaacacgcct gcaactctgc ccctgggggg cgaggacacc acctggaccc ctgggatcaa
 121 cgccagctgg gctccggatg aggaggagga tgcagtgcgg tccgacggca cggggacagc
 181 gggcatggta actatccagt gcatcctatg gctcgtgtgt ctggtgggcc tggtaggaaa
 241 cgccctggtc atattcgtga tcctacgcta tgccaaaatg aagacagcca ccaacatcta
 301 cctgctcaac ctggccgtcg ctgatgagct cttcatgctc agtgtgccat tgtggcctc
 361 gcggctgcc ctgcgccact ggccgttcgg ggcggtgctg tgccgcgcag tgcttagtgt
 421 gacggccctt aacatgttca cgagtgtctt ctgcctcaca gtgctcagcg tggatcgcta
 481 tgtggctgta gtgcacctc tgcgagctgc cacctaccgg cggcccagcg tggccaagct
 541 aatcaacctg gagtgtggc tagcatcctt gctggtcacc ctgcccatcg cagtcttcgc
 601 tgacactagg ccagctcgtg ggggtgaggc agtagcttgc aacctgcact ggcctcaccc
 661 ggcctggtct gcagtcttg tgatctatac tttttgctg ggcttcctac tcccggttct
 721 ggctatcgga ttatgttacc tgcttatcgt gggcaagatg cgtgctgtgg ccctgcgggc
 781 tggctggcaa caacggaggc gctcagagaa gaagatcact aggctcgtgc taatggtggt
 841 gactgtcttt gtgctatgct ggatgccatt ctatgtagtg cagcttctga atctgtttgt
 901 caccagcctc gatgccactg tcaaccatgt gtccctcatc ctcagctatg ccaacagctg
 961 tgccaacccg attctctatg gtttcctctc agacaacttc cgacgctctt tccagcgggt
1021 tctgtgcctg cgctgctgtc tcctggaaac aactggaggt gctgaggaag agcccctgga
1081 ctactatgct actgctctca aaagcagagg tgggccagga tgcatatgcc ctccattgcc
1141 ctgccagcag gagcccatgc aagcagaacc tgcctgcaag cgagtccctt tcaccaagac
1201 cactactttc tgaaaaccat ttcaccctcc ctcagcccac ctgcaagcag gtctgcacca
1261 cactctcaag ccagcaactt caagaaaact cctgttgtca ctaagccagg cccttttcagc
1321 agcctgtgtt ctgtccctag gagcctcagg actcctgcta gccctgcct ctcctaggac
1381 tgactggatc caaggacaac tccgtggggg taggacttct ctgggttttg ggctagagta
1441 ccatccatcc tttcatggac ctctagcaat tttttcaagag gcaggaagca ggtggtggtc
1501 agaaagggat gcctaccctt gtgtgacttt gacagtgac tgcttggaag agcgctggga
1561 gggtgaggta ggcagagcta ggctctctgc tgtgtggtag catagggcat acggtgatac
1621 aggggagaag atatgatacc tccaagtgtt ttccctctgt gtctgtctga gtctcttgtt
1681 gctaaatgag atgtctaagc aacagctgaa agcatttgct ttcccaaggc aaatgttttt
1741 ccagttgtca aaggaccagt agcagacttc ctgagaatgc aaatgtttaa agaaggatgg
1801 tgtggggcgt tttttgaaaa aaaaaataat tctgatttct ggtcaggaat taaaaggcag
1861 aaagg
```

Human Somatostatin Receptor Type 5 mRNA (NCBI: NM_001053 (SEQ ID NO:25))
```
   1 atggagcccc tgttcccagc ctccacgcca agctggaacg cctcctcccc ggggctgcc
  61 tctggaggcg gtgacaacag gacgctggtg gggccggcgc cctcggcagg ggcccggggcg
 121 gtgctggtgc ccgtgctgta cctgctggtg tgtgcggccg ggctgggcgg gaacacgctg
 181 gtcatctacg tggtgctgcg cttcgccaag atgaagaccg tcaccaacat ctacattctc
 241 aacctgcag tggccgacgt cctgtacatg ctggggctgc ctttcctggc cacgcagaac
 301 gccgcgtcct tctggccctt cggccccgtc ctgtgccgc tggtcatgac gctggacggc
 361 gtcaaccagt tcaacagtgc cttctgcctg acagtcatga gcgtggaccg ctacctggca
 421 gtggtgcacc cgctgagctc ggcccgctgg cgccgcccgc gtgtggccaa gctggcgagc
 481 gccgcggcct gggtcctgtc tctgtgcatg tcgctgccgc tcctggtgtt cgcggacgtg
 541 caggagggcg gtacctgcaa cgccagctgg ccggagcccg tgggctgtg gggcgccgtc
 601 ttcatcatct acacgcccgt gctgggcttc ttcgcgccgc tgctggtcat ctgcctgtgc
 661 tacctgctca tcgtggtgaa ggtgaggcgc gcgggcgtgc gcgtgggctg cgtgcgcgg
 721 cgctcggagc ggaaggtgac gcgcatggtg ttggtggtgg tgctggtgtt tgcgggatgt
 781 tggctgcct tcttcaccgt caacatcgtc aacctggccg tggcgctgcc ccaggagccc
 841 gcctccgccg gcctctactt cttcgtggtc atcctctcct acgccaacag ctgtgccaac
 901 cccgtcctct acggcttcct ctctgacaac ttccgccaga gcttccagaa ggttctgtgc
 961 ctccgcaagg gctctggtgc caaggacgct gacgccacgg agccgcgtcc agacaggatc
1021 cggcagcagc aggaggccac gccgccgcg caccgcgccg cagccaacgg gcttatgcag
1081 accagcaagc tgtga
```

Rat Somatostatin Receptor Type 5 mRNA (NCBI: NM_012882 (SEQ ID NO:26))
```
   1 ccgacttcgt acagcaatcg agtgagcaca ctgatctttg agcccgagtg cgctgcctaa
  61 ctgcgaagta ccgccgccgt gcccgccccg cgtgggcac cctgtcctgc acagagacac
 121 gcgtggtctg gcaccggcc tgaagctgac agcatggaga ccctctctat ggcctccaca
 181 ccaagctgga tgcctcggc tgcttccagt ggtaaccata actggtcact ggtgggctca
 241 gcatcgccaa tgggagcccg gcagtatta tgcctgtgc ctacctgtt ggtgtgcacc
 301 gtgggactga gtggaaatac actggtcatt tatgtggtc tgcggcacgc caagatgaag
 361 acagttacta acgtgtacat cctgaacctg gccgtggcgt acgtattatt tatgttggga
 421 cttccttttcc tggccacgca gaacgacgtc gtcctactact ggcccttcgg ctccttcttg
 481 tgccgcctgg tcatgacact ggatggcatc aaccagttca ccagtatctt ctgcctgatg
 541 gtcatgagtg ttgaccgcta cctggccgtg gtccaccctc tccgctcagc ccgtggggcgt
 601 cgcccacggg tagccaagat ggccagcgcg gccgtctggg tcttttcgct gctcatgtct
```

TABLE 5-continued

```
 661 ctgccgctct tggtcttcgc ggatgtccag gagggctggg gcacctgcaa cctgagatgg
 721 ccagagcctg tggggctgtg gggtgcagcc ttcatcacct acacgtctgt gttgggcttc
 781 tttgggcccc tgctggtcat ctgcttgtgc tacctgctca ttgtggtcaa ggtgaaggct
 841 gcaggcatgc gagtaggctc ctcaaggcgg aggcgctcgg agccgaaggt gactcgcatg
 901 gtggtggtcg tggtgctggt gtttgtgggc tgctggctgc cttcttcat tgtcaacatc
 961 gtcaacctgg ccttcacact gcccgaggaa cccacatatg ccggcctcta tttctttgtg
1021 gtggtcctat cttatgccaa tagctgtgcc aaccccctgc tctacggctt tctctcggac
1081 aacttccgcc agagcttccg gaaggttctg tgcctacgta gaggatacgg tatggaggat
1141 gcggacgcca tagagccacg gccagacaag agtgggcggc tcaggccac actgcccaca
1201 cgcagctgcg aggccaatgg gctcatgcag accagcagga tttgaatgcc cctgtaacac
1261 cctgggggtc ctccaggcct ccacggtgtt gtcttctggg atctgagagt ttgatgagat
1321 gcattcaccc ccaggcctac aagttggact cctctcggtg gcagtgtgaa gacaggacct
1381 gcag
```

TABLE 6

List of Disclosed Peptide Based Somatostatin Receptor Antagonists and Structures

| Peptide No. | Peptide code | Other Names | Ref. |
|---|---|---|---|
| 27 | AC 178, 335 | | 49, 51, 52 |
| 28 | BIM-23458 | DC-41-33, PRL-2903 | 27, 28, 51, 54, 55, 56 |
| 29 | BIM-23627 | | 49, 52, 56 |
| 30 | CYN 154806 | D-Tyr8 | 49, 57, 59 |
| 31 | CYN 154806 | L-Tyr8 | 49, 57, 59 |
| 32 | PRL-2915 | | 53, 60 |
| 33 | PRL-2970 | | 49, 53, 60 |
| 34 | BIM-23454 | | 51, 56, 61, 62 |
| 35 | cyclo-somatostatin | | 51, 58, 68 |
| 36 | DC-38-48 | | 53 |
| 37 | PRL-2876 | | 53 |
| 38 | PRL-2874 | | 53 |
| 39 | PRL-2877 | | 53 |
| 40 | PRL-2879 | | 53 |
| 41 | PRL-2875 | | 53 |
| 42 | PRL-2889 | | 53 |
| 43 | PRL-2900 | | 53 |
| 44 | PRL-2891 | | 53 |
| 45 | PRL-2908 | | 53 |
| 46 | PRL-2882 | | 53 |
| 47 | PRL-2904 | | 53 |
| 48 | PRL-2910 | | 53 |
| 49 | PRL-3020 | | 53 |
| 50 | PRL-3052 | | 53 |
| 51 | PRL-3023 | | 53 |
| 52 | PRL-3024 | | 53 |
| 53 | PRL-2972 | | 53 |
| 54 | PRL-2894 | SB-710411 | 51, 53 |
| 55 | PRL-2859 | | 53 |
| 56 | PRL-2872 | | 53 |
| 57 | PRL-2888 | | 53 |
| 58 | PRL-2858 | | 53 |
| 59 | PRL-2869 | | 53 |
| 60 | PRL-2857 | | 53 |
| 61 | PRL-2868 | | 53 |
| 62 | PRL-2917 | | 53 |
| 63 | PRL-2918 | | 53 |
| 64 | PRL-2905 | | 53 |
| 65 | PRL-2907 | | 53 |
| 66 | PRL-2856 | | 53 |
| 67 | PRL-2862 | | 53 |
| 68 | PRL-3064 | | 53 |
| 69 | PRL-2855 | | 53 |
| 70 | PRL-2870 | | 53 |
| 71 | PRL-2902 | | 53 |
| 72 | PRL-2896 | | 53 |
| 73 | PRL-2878 | | 53 |
| 74 | PRL-2897 | | 53 |
| 75 | PRL-2898 | | 53 |
| 76 | PRL-2883 | | 53 |
| 77 | RJ-01-48 | | 60 |
| 78 | NC-11-31 | | 60 |
| 79 | DC-38-28 | | 60 |
| 80 | DC-38-25 | | 60 |
| 81 | DC-38-45 | | 60 |
| 82 | DC-8-42 | | 60 |
| 83 | DC-32-15 | | 60 |
| 84 | DC-38-73 | | 60 |
| 85 | DC-38-76 | | 60 |
| 86 | DC-38-58 | | 60 |
| 87 | BIM-23246 | | 60 |
| 88 | DC-38-61 | | 60 |
| 89 | DC-38-55 | | 60 |
| 90 | BIM-23255 | | 60 |
| 91 | JF-04-31 | | 60 |
| 92 | DC-13-187 | | 60 |
| 93 | DC-13-209 | | 60 |
| 94 | DC-38-19 | | 60 |
| 95 | DC-38-22 | | 60 |
| 96 | DC-38-15 | | 60 |
| 97 | DC-38-39 | | 60 |
| 98 | DC-38-35 | | 60 |
| 99 | DC-32-57 | | 60 |
| 100 | DC-38-67 | | 60 |
| 101 | DC-38-64 | | 60 |
| 102 | NC-8-61 | | 60 |
| 103 | DC-32-53 | | 60 |
| 104 | DC-38-70 | | 60 |
| 105 | JF-04-47 | | 60 |
| 106 | RJ-01-14 | | 60 |
| 107 | RJ-01-20 | | 60 |
| 108 | JF-04-27 | | 60 |
| 109 | DC-38-51 | | 60 |
| 110 | RJ-01-28 | | 60 |
| 111 | RJ-01-44 | | 60 |
| 112 | RJ-01-76 | | 60 |
| 113 | RJ-01-31 | | 60 |
| 114 | RJ-01-36 | | 60 |
| 115 | RJ-01-40 | | 60 |
| 116 | RJ-01-80 | | 60 |
| 117 | DC-37-57 | | 60 |
| 118 | DC-37-83 | | 60 |
| 119 | JF-04-33 | | 60 |
| 120 | DC-41-85 | | 63 |
| 121-136 | | | 64 |
| 137-151 | | | 65 |
| 152-173 | | | 66 |
| 174-436 | | | 67 |

* or a pharmaceutically accepted salt thereof.

TABLE 7

Subset of SSTR Peptide Antagonists*

| Action | Receptor | Ligand Name | Affinity (nM) | Units | References |
|---|---|---|---|---|---|
| Antagonist | SSTR-2 | AC-178, 335 | 6.8 | pKi7 | 49, 51, 52 |
| Antagonist | SSTR-2 | BIM 23, 458 | 27.4 | pIC50 | 27, 28, 51, 54, 55, 56 |
| Antagonist | SSTR-2 | BIM 23, 627 | 6.4 | pIC50 | 49, 52, 56 |
| Antagonist | SSTR-2 | BIM 23, 454 | 31.6 | pIC50 | 49, 57, 59 |
| Antagonist | SSTR-2 | D-Tyr8-CYN 154806 | 8.4-8.9 | pKi81 | 49, 57, 59 |
| Antagonist | SSTR-2 | L-Tyr8-CYN 154806 | 8.1-8.4 | pKi81 | 53, 60 |
| Antagonist | SSTR-2 | PRL-2915 | 7.9 | pKi52 | 49, 53, 60 |
| Antagonist | SSTR-2 | PRL-2970 | 7.8 | pKi52 | 51, 56, 61, 62 |

| Action | Structure | Seq. ID No. |
|---|---|---|
| Antagonist | AC-His-Phe-Ile-Arg-Trp-Phe-NH2 | 27 |
| Antagonist | H-Fpa-cyclo[DCys-Pal-DTrp-Lys-Tle-Cys]-Nal-NH2 | 28 |
| Antagonist | H-p-Chloro-DPhe-cyclo[DCys-Pal-Trp-Lys-Val-Cys]-2-Nal-NH2 | 29 |
| Antagonist | H-Cpa-Cys-Pal-Trp-Lys-Val-Cys-Nal-NH2 | 30 |
| Antagonist | Ac-4-NO2-Phe-cyclo[D-Cys-Tyr-DTrp-Lys-Thr-Cys]-DTyr-NH2 | 31 |
| Antagonist | Ac-4-NO2-Phe-cyclo[DCys-Tyr-DTrp-Lys-Thr-Cys]-LTyr-NH2 | 32 |
| Antagonist | H-Cpa-cyclo[DCys-Pal-DTrp-Lys-Tle-Cys]-Nal-NH2 | 33 |
| Antagonist | H-Cpa-cyclo[DCys-Tyr-DTrp-Lys-thr-Cys]-Nal-NH2 | 34 |

*and pharmaceutically accepted salts thereof.

TABLE 8

List of Abbreviations* Used

| | |
|---|---|
| 2,4-dichloro-Phe | β-[2,4-dichlorophenyl]-alanine |
| 1-Nal | 3-(1-naphthyl)alanine |
| 2Fpa | 2-fluorophenylalanine |
| 2-Nal | 3-(2-naphthyl)alanine |
| 2Pal | 2-pyridylalanine |
| 2-Pal | [2-pyridyl]-alanine or 3-(2-pyridyl)alanine |
| 3Fpa | 3-fluorophenylalanine |
| 3-I-Tyr | 3-iodotyrosine |
| 3-Pal | 3-(3-pyridyl)alanine |
| 4-Pal | 3-(4-pyridyl)alanine |
| Abu | 2-aminobutyric acid or α-aminobutyric acid |
| Ahp | 7-aminoheptanoic acid |
| Aib | 2-aminoisobutyric acid or α-aminoisobutyric acid |
| Amp | 4-amino-phenylalanine |
| Ava | 5-aminovaleric acid |
| β-Ala | β-alanine or 3-aminopropionic acid |
| β-1-Nal | β-[1-naphthyl]-alanine |
| β-Nal | β-[2-napthyl]-alanine |
| Bip | biphenylalanine or 4,4'-biphenylalanine |
| Bpa | 4-bromophenylalanine |
| Bta | benzothienylalanine or 3-benzothienylalanine |
| Cha | cyclohexylalanine or β-(cyclohexyl)-alanine |
| Cpa | 3-(4-chlorophenyl)alanine |
| Dab | 2,4-diaminobutyric acid |
| Dap | 2,3-diaminopropionic acid |
| Dip | 3,3'-diphenylalanine |
| F5-Phe | 2,3,4,5,6-pentafluorophenyl]-alanine |
| Fpa | 4-fluorophenylalanine |
| Gaba | γ-aminobutyric acid or 4-aminobutyric acid |
| HSer | homoserine |
| Igl | 2-indanylglycine |
| Iph | 4-iodophenylalanine |
| Nal | 3-(2-naphthyl)alanine |
| Nle | norleucine |
| Npa | 4-nitrophenylalanine, or p-NO2-phenylalanine |
| Nva | norvaline |
| Pal | 3-pyridylalanine or β-[3-pyridyl]-alanine |
| Pen | peniciliamine |
| Pfp | pentaflurophenylalanine |
| Tba | tert-butylalanine |
| Tfm | Trifluoromethyl |
| TfmA | 4-trifluoromethylphenyl-alanine |
| Thr(Bzl) | O-benzyl-threonine |
| Tic | 1,2,3,4-tetrahydroisoquinoline-3-carboxylic acid |
| Tle | tert-leucine or α-[t-butyl]-glycine |
| Tyr(Bzl) | O-benzyl-tyrosine |
| Tyr(I) | An iodinated tyrosine residue (e.g., 3-1-Tyr, 5-1-Tyr, 3,5-1-Tyr) wherein the iodine may be a radioactive isotope, e.g., I125, I127, or I131 |
| Ypa | 4-cyanophenylalanine |

*Abbreviations of the common amino acids are in accordance with the recommendations of IUPAC-IUB
*With the exception of the N-terminal amino acid, all abbreviations (e.g., Ala or A2) of amino acids in this disclosure stand for the structure of —NH—CH(R)—CO—, wherein R is a side chain of an amino acid (e.g., CH3 for Ala). For the N-terminal amino acid, the abbreviation stands for the structure of =N—CH(R)—CO—, wherein R is a side chain of an amino acid.

REFERENCES

1. Shi, Z, Rastogi, K, Lekas, M, Efendic, S, Drucker, D, and Vranic, M: Glucagon response to hypoglycemia is improved by insulin-independent restoration of normoglycemia in diabetic rats. *Endocrinology* 137:3193-3199, 1996
2. Miles, P, Yamatani, K, Lickley, H, and Vranic, M: Mechanism of glucoregulatory responses to stress and their deficiency in diabetes. *Proceedings of the National Academy of Sciences U.S.A* 88:1296-1300, 1991
3. Yue, J T Y, Goche Montes, D, Bates, H E, Kiraly, M A, Matthews, S G, and Vranic, M: Effects of recurrent stress on counterregulation to hypoglycemia and restraint in normal and diabetic rats (in preparation). 2007.
4. Purdon, C, Brousson, M, Nyveen, S, Miles, P, Halter, J, Vranic, M, and Marliss, E: The roles of insulin and catecholamines in the glucoregulatory response during intense exercise and early recovery in insulin-dependent diabetic and control subjects. *J. Clin. Endocrinol. Metab.* 76:566-573, 1993
5. Sigal, R, Purdon, C, Fisher, S, Halter, J, Vranic, M, Marliss, E: Hyperinsulinemia prevents prolonged hyperglycemia after intense exercise in insulin-dependent diabetic subjects. *J. Clin. Endocrinol. Metab.* 79:1049-1057, 1994
6. Kahn, S, Porte Jr. D: Hypoglycemia in type 1 diabetes mellitus: Interplay of insulin excess and compromised glucose counterregulation. In Ellenberg & Rifkin's Diabetes Mellitus. Porte Jr D, Sherwin R, Baron A, Eds. New York, McGraw-Hill, 2003, p. 331-365
7. Wasserman, D, Shi, Z, Vranic. M: Metabolic implications of exercise and physical fitness in physiology and diabetes. In Ellenberg & Rifkin's Diabetes Mellitus, Porte Jr D, Sherwin R, Baron A, Eds. New York, McGraw-Hill, 2003, p. 453-480
8. Amatruda, J, and Livingston, J: Glucagon. In Ellenberg and Rifkin's Diabetes Mellitus. Porte Jr D, Sherwin R, Baron A, Eds. New York, McGraw-Hill, 2003, p. 97-115
9. Dong, H, Kumar, H, Zhang, Y, Gyulkhandanyan, A, Xiang, Y, Ye, B, Perrella, J, Hyder, A, Zhang, N, Wheeler, M, Lu, W, Wang, Q: Gamma-aminobutyric acid up- and downregulates insulin secretion from beta cells in concert with changes in glucose concentration. *Diabetologia* 2006
10. Xu, E, Kumar, M, Ju, W, Obata, T, Zhang, N, Deng, S, Ebina, Y, Braun, M, Wang, Q: Intra-islet insulin suppresses glucagon release via GABA-GABAA receptor system. *Cell Metabolism* 3:47-58, 2006
11. Rastogi, K, Lickley, L, Jokay, M, Efendic, S, and Vranic, M: Paradoxical reduction in pancreatic glucagon with normalization of somatostatin and decrease in insulin in normoglycemic alloxan diabetic dogs: A putative mechanism of glucagon irresponsiveness to hypoglycemia. *Endocrinology* 126:1096-1104, 1990
12. Rastogi, K, Brubaker, P, Kawasaki, A, Efendic, S, and Vranic, M: Increase in somatostatin to glucagon ratio in islets of alloxan-diabetic dogs: effect of insulin-induced euglycemia. *Canadian Journal of Physiology and Pharmacology* 71:512-517, 1993
13. Orci, L, Baetens, D, Rufener, C, Amherdt, M, Ravazzola, M, Studer, P, Malaisse-Lagae, F, and Unger, R: Hypertrophy and hyperplasia of somatostatin-containing D-cells in diabetes. *Proceedings of the National Academy of Sciences U.S.A* 73:1338-1342, 1976
14. Brubaker, P, So, D, and Drucker, D: Tissue-specific differences in the levels of proglucagon-derived peptides in streptozotocin-induced diabetes. *Endocrinology* 124:3003-3009, 1989
*15. Inouye, K, Shum, K, Chan, O, Mathoo, J, Matthews, S, and Vranic, M: Effects of recurrent hyperinsulinemia with and without hypoglycemia on counterregulation in diabetic rats. *American Journal of Physiology Endocrinology and Metabolism* 282:E1369-E1379, 2002
16. Rossowski, W, and Coy, D: Specific inhibition of rat pancreatic insulin or glucagon release by receptor-selective somatostatin analogs. *Biochemical and Biophysical Research Communications* 205:341-346, 1994
17. Strowski, M, Parmar, R, Blakde, A, and Schaeffer, J: Somatostatin inhibits insulin and glucagon secretion via two receptor subtypes: an in vitro study of pancreatic islets from somatostatin receptor 2 knockout mice. *Endocrinology* 141:111-117, 2000
18. Kumar, U, Sasi, R, Suresh, S, Patel, A, Thangaraju, M, Metrakos, P, Patel, S, and Patel, Y: Subtype-selective expression of the five somatostatin receptors (hSSTR1-5) in human pancreatic islet cells: a quantitative double-label immunohistochemical analysis. *Diabetes* 48:77-85, 1999
19. Reubi, J, Kappeler, A, Waser, B, Schonbrunn, A, and Laissue, J: Immunohistochemical localization of somatostatin receptor sst2A in human pancreatic islets. *J. Clin. Endocrinol. Metab.* 83:3746-3749, 1998
20. Kimura, N, Schindler, M, Kasai, N, and Kimura, I: Immunohistochemical localization of somatostatin receptor type 2A in rat and human tissues. *Endocrine Journal* 48:95-102, 2001
21. Maurer, R, and Reubi, J: Somatostatin receptors in the adrenal. *Molecular and Cellular Endocrinology* 45:81-90, 1986
22. Role, L, Leeman, S, and Perlman, R: Somatostatin and substance P inhibit catecholamine secretion from isolated cells of guinea-pig adrenal medulla. *Neuroscience* 6:1813-1821, 1981
23. Mizobe, F, Kozousek, V, Dean, D, and Livett, B: Pharmacological characterization of adrenal paraneurons: substance P and somatostatin as inhibitory modulators of the nicotinic response. *Brain Research* 178:555-566, 1979
24. Havel P, and Taborsky G J: Stress-induced activation of the neuroendocrine system and its effects on carbohydrate metabolism. In Ellenberg and Rifkin's Diabetes Mellitus. Porte Jr D, Sherwin R, Baron A, Eds. New York, McGraw-Hill, 2003, p. 127-149
25. Fehlmann D, Langenegger D, Schuepbach E, Siehler S, Feuerbach D, and Hoyer D: Distribution and characterisation of somatostatin receptor mRNA and binding sites in the brain and periphery. *Journal of Physiology (Paris)* 94:265-281, 2000
26. Lanneau C, Viollet C, Faivre-Bauman A, Loudes C, Kordon C, Epelbaum J, and Gardette R: Somatostatin receptor subtypes sst1 and sst2 elicit opposite effects on the response to glutamate of mouse hypothalamic neurones: an electrophysiological and single cell RT-PCR study. *European Journal of Neuroscience* 10:204-212, 1998
27. Cejvan, K, Coy, D, Holst, J, Cerasi, E, and Efendic, S: Gliclazide directly inhibits arginine-induced glucagon release. *Diabetes* 51 Suppl 3:S381-S384, 2002
28. Cejvan, K, Coy, D, and Efendic, S: Intra-islet somatostatin regulates glucagon release via type 2 somatostatin receptors in rats. Diabetes 52:1176-1181, 2003
29. Rossowski, W, Cheng, B, Jiang, N, and Coy, D: Examination of somatostatin involvement in the inhibitory action of GIP, GLP-1, amylin and adrenomedullin on gastric acid release using a new SRIF antagonist analogue. *British Journal of Pharmacology* 125:1081-1087, 1998
30. Patel, Y: Somatostatin and its receptor family. *Frontiers in Neuroendocrinology* 20:157-198, 1999
31. Miles, P, Yamatani, K, Brown, M, Lickley, L, and Vranic, M: Intracerebroventricular administration of somatostatin octapeptide counteracts the hormonal and metabolic responses to stress in normal and diabetic dogs. *Metabolism* 43:1134-1143, 1994
32. Kimura, N, Schindler, M, Kasai, N, and Kimura, I: Immunohistochemical localization of somatostatin receptor type 2A in rat and human tissues. *Endocrine Journal* 48:95-102, 2001
33. O'Carroll, A: Localization of messenger ribonucleic acids for somatostain receptor subtypes (sstr1-5) in the rat adrenal gland. *The Journal of Histochemistry and Cytochemistry* 51:55-60, 2003
34. Maurer, R, and Reubi, J: Somatostatin receptors in the adrenal. *Molecular and Cellular Endocrinology* 45:81-90, 1986

35. Morel, G, Leroux, P, Garcia Caballero, T, Beiras, A, and Gossard, F: Ultrastructural distribution of somatostatin-14 and -28 in rat adrenal cells. *Cell and Tissue Research* 261: 517-524, 1990
36. Diagnosis and Classification of Diabetes Mellitus, American Diabetes Association Diabetes Care 2006 29: S43-48
37. Kohler, G and Miltsein. C: Continuous cultures of fused cells secreting antibody of predefined specificity. *Nature* 256:495-497, 1975
38. Kozbor, D, and Roder, J: The production of monoclonal antibodies from human lymphocytes. *Immunology Today* 4:3 72-79, 1983
39. Cole et al. Monoclonal Antibodies in Cancer Therapy (1985) Allen R. Bliss, Inc., pages 77-96
40. Huse, W, Sastry, L, Iverson, S, Kang, A, Alting-Mees, M, Burton, D, Benkovic, S, and Lerner, R: Generation of a large combinatorial library of the immunoglobulin repertoire in phage lambda. *Science* 246:4935 1275-1282, 1989
41. Morrison, S, Johnson, M, Herzenberg, L, and Oi, V: Chimeric Human Antibody Molecules Mouse Antigen-Binding Domains with Human Constant Region Domains. *PNAS* 81:21 6851-6855, 1984
42. Takeda, S-I, Naito, T, Hama, K, Noma, T, and Honjo, T: Construction of chimaeric processed immunoglobulin genes containing mouse variable and human constant region sequences. *Nature* 314:452-454
43. Teng, N, Lam, K, Riera, F, and Kaplan, H: Construction and Testing of Mouse—Human Heteromyelomas for Human Monoclonal Antibody Production. *PNAS* 80:12 7308-7312, 1983
44. Olsson et al., *Methods in Enzymol,* 92:3-16 1982
45. Ward, E, Güssow, D, Griffiths, A, Jones, P, and Winter, G: Binding activities of a repertoire of single immunoglobulin variable domains secreted from *Escherichia coli*. *Nature* 348:544-546, 1989
46. McCafferty, J, Griffiths, A, Winter, G, and Chiswell, D: Phage antibodies: filamentous phage displaying antibody variable domains. *Nature* 348:552-555, 1989
47. Raynor, K, Murphy, W, Coy, D, Taylor, J, Moreau, J-P, Yasuda, K, Bell, G, and Reisine, T: Cloned Somatostatin Receptors: Identification of Subtype Selective Peptides and demonstration of high affinity binding linear peptides. Molecular Pharmacology, 43:838-844, 1993
48. Patel, Y and Srikant, C: Subtype selectivity of peptide analogs for all five cloned human samatostatin receptors (hsstr 1-5). Endocrinology, 136:6 2814-2817, 1994.
49. Weckbecker, G, Lewis, I, Albert, R, Schmid, H, Hoyer, D, and Bruns, C: (2003), Opportunities in samatostatin research: Biological, chemical and therapeutic aspects. Nature Reviews: Drug Discovery, 2, 999-1017, 2003
50. Simon, R, Kania, R, Zuckermann, R, Huebner, V, Jewell, D, Banville, S, Ng, S, Wang, L, Rosenberg, S, Marlowe, C, Spellmeyer, D, Tan, R, Frankel, A, Santi, D, Cohen, F, and Bartlett, P: Peptoids: A Modular Approach to Drug Discovery. *PNAS* 89:9367-9371, 1992
51. Traitement de resistance a l'insuline par modulation de somatostatine au moyen d'antagonistes du recepteur de la somatostatine 2006 WO/2006/063465
52. Baumbach, W, Carrick, T, Pausch, M, Bingham, B, Carmignac, D, Robinson, I, Houghten, R, Eppler, C, Price, L, and Zysk, J: A linear hexapeptide somatostatin antagonist blocks somatostatin activity in vitro and influences growth hormone release in rats. *Mol Pharmacol,* 54:864-873, 1998
53. Hocart, S, Jain, R, Murphy, W, Taylor, J, and Coy, D: Highly potent cyclic disulfide antagonists of somatostatin. *Journal of Medicinal Chemistry* 42:1863-1871, 1999
54. Singh, V, Brendel, M, Zacharias, S, Mergler, S, Jahr, H, Wiedenmann, B, Bretzel, R, Plockinger, U, Strowski, M: Characterization of somatostatin receptor subtype-specific regulation of insulin and glucagon secretion: an in vitro study on isolated human pancreatic islets. *Journal of Clinical Endocrinology and Metabolism* 92:673-680, 2007
55. Rossowski, W, Cheng, B, Jiang, N, Coy, D: Examination of somatostatin involvement in the inhibitory action of GIP, GLP-1, amylin and adrenomedullin on gastric acid release using a new SRIF antagonist analogue. *British Journal of Pharmacology* 125:1081-1087, 1998
56. Tulipano, G, Soldi, D, Bagnasco, M, Culler, M, Taylor, J, Cocchi, D, Giustina, A: Characterization of new selective somatostatin receptor subtype-2 (sst2) antagonists, BIM-23627 and BIM23454. Effects of BIM-23627 on GH release in anesthetized male rats after short-term high-dose dexamethasone treatment. *Endocrinology* 143:1218-1224, 2002
57. Bass, R, Buckwalter, R, Patel, B, Pausch, M, Price, L, Strnad, J, and Hadcock, J: Identification and characterization of novel somatostatin antagonists. Molecular Pharmacology 50:709-715 and Bass R, Buckwalter R, Patel B, Pausch M, Price L, Strnad J, Hadcock J 1997 Identification and characterization of novel somatostatin antagonists, erratum. *Molecular Pharmacology* 51:170, 1996
58. Fries, J, Murphy, W, Sueiras-Diaz, J, Coy, D: Somatostatin antagonist analogue increases GH, insulin and glucagon release in the rat. *Peptides* 3:811-814, 1982
59. Nunn, C, Schoeffter, P, Langenegger, D, and Hoyer, D: Functional characterisation of the putative somatostatin sst2 receptor antagonist CYN 154806. *Naunyn Schmiedebergs Arch Pharmacol,* 367:1-9, 2003
60. Hocart, S, Jain, R, Murphy, W, Taylor, J, Morgan, B, and Coy, D: Potent antagonists of somatostatin: synthesis and biology. *Journal of Medicinal Chemistry* 41:1146-1154, 1998
61. Morgan, B, Anderson, W, Coy, D, Culler, M, MacArthur, M, Mierke, D, Pellegrini, M, Piserchio, A, Sadat Allee, D, and Taylor, J: Identification and exploitation of structural foci that influence conformational mobility in somatostatin agonists and antagonists. Peptides for the New Millenium. Springer Netherlands, vol 6:245-247, 2002
62. Ren, S-G, Taylor, J, Dong, J, Yu, R, Culler, M, and Melmed, S: Functional association of somatostatin receptor subtypes 2 and 5 in inhibiting human growth hormone secretion. *Journal of Clinical Endocrinology and Metabolism* 88:4239-4245, 2003
63. Cardelli, P, Fiori, A, Corleto, V, Savi, M, Granata, F, Ceci, F, Ferraguti, G, Potenza, R, Fave, G, Jensen, R, Strom, R: Inhibitory effect of somatostatin on neutral amino acid transport in isolated brain microvessels. *Journal of Neurochemistry* 78:349-357, 2001
64. Patent Application Numbers: WO02072602A2; US24181032A1 and US28020970A1
65. U.S. Pat. No. 6,262,229
66. U.S. Pat. No. 6,703,481
67. Patent Application Number: US24097418A1
68. Heppelmann, B, and Pawlak, M: Peripheral application of cyclo-somatostatin, a somatostatin antagonist, increases the mechanosensitivity of rat knee joint afferents. *Neurosciences Letters* 259:62-64, 1999

The invention claimed is:

1. A method of controlling tight blood glucose levels comprising administering an effective amount of a somatostatin receptor (SSTR) antagonist to a subject in need thereof, wherein the subject has idiopathic hypoglycemia or an insulinoma tumor or the subject is a diabetic subject with insulin-induced hypoglycemia.

2. The method of claim 1 for treating hypoglycemia.

3. The method of claim 1, wherein the subject is an insulin-dependent diabetic.

4. The method of claim 3, wherein the subject has Type I diabetes.

5. The method of claim 3, wherein the subject has Type II diabetes.

6. The method of claim 1, wherein the subject suffers from idiopathic hypoglycemia.

7. The method of claim 1, wherein the subject has an insulinoma tumor.

8. The method of claim 1, wherein the somatostatin receptor antagonist is a peptide antagonist of SSTR or a pharmaceutically acceptable salt thereof.

9. The method of claim 1, wherein the somatostatin receptor antagonist is a peptide antagonist of SSTR2 or a pharmaceutically acceptable salt thereof.

10. The method of claim 1, wherein the somatostatin receptor antagonist is an antagonist of SSTR having a peptide as listed in any one of peptide no.s:27-436 of Table 6 or a pharmaceutically acceptable salt thereof.

11. The method of claim 1, wherein the somatostatin receptor antagonist is an antagonist of SSTR having a peptide as listed in any one of peptide no.s:27-120 of Table 6 or a pharmaceutically acceptable salt thereof.

12. The method of claim 1, wherein the somatostatin receptor antagonist is an antagonist of SSTR having a peptide sequence as shown in SEQ ID NOs:27-34 or a pharmaceutically acceptable salt thereof.

13. The method of claim 1, wherein the antagonist of SSTR is the cyclic-octapeptide as shown in SEQ ID NO:28 or a pharmaceutically acceptable salt thereof.

14. The method of claim 1, wherein the somatostatin receptor antagonist is an antibody against a somatostatin receptor.

15. The method of claim 14, wherein the antibody against the somatostatin receptor binds to a somatostatin receptor having the amino acid sequence as shown in any one of SEQ ID NOs:5-14.

16. The method of claim 14, wherein the antibody against the somatostatin receptor binds to a somatostatin receptor 2 having the amino acid sequence as shown in SEQ ID NO:7 or SEQ ID NO:8.

17. The method of claim 1, wherein the subject is a mammal.

18. The method of claim 17, wherein the mammal is human.

19. The method of claim 1, wherein the subject has a blood glucose level of less than 4.0 mM.

* * * * *